US009663805B2

(12) United States Patent
Raemakers-Franken et al.

(10) Patent No.: US 9,663,805 B2
(45) Date of Patent: May 30, 2017

(54) PREPARATION OF 6-AMINOCAPROIC ACID FROM 5-FORMYL VALERI C ACID

(71) Applicant: Genomatica, Inc, San Diego, CA (US)

(72) Inventors: Petronella Catharina Raemakers-Franken, Budel (NL); Martin Schurmann, Julich (DE); Axel Christoph Trefzer, Leidschendam (NL); Stefaan Marie Andre De Wildeman, Maasmechelen (BE)

(73) Assignee: Genomatica, Inc., San Diego, CA (US)

( * ) Notice: Subject to any disclaimer, the term of this patent is extended or adjusted under 35 U.S.C. 154(b) by 167 days.

(21) Appl. No.: 14/105,705

(22) Filed: Dec. 13, 2013

(65) Prior Publication Data

US 2014/0134681 A1   May 15, 2014

Related U.S. Application Data

(63) Continuation of application No. 12/921,733, filed as application No. PCT/NL2009/050117 on Mar. 11, 2009, now Pat. No. 8,673,599.

(30) Foreign Application Priority Data

Mar. 11, 2008  (EP) ..................... 08152584

(51) Int. Cl.
| | | |
|---|---|---|
| *C12P 13/02* | (2006.01) | |
| *C12P 7/40* | (2006.01) | |
| *C12P 7/26* | (2006.01) | |
| *C12P 13/00* | (2006.01) | |
| *C07C 227/06* | (2006.01) | |
| *C07D 223/10* | (2006.01) | |
| *C07D 201/08* | (2006.01) | |

(52) U.S. Cl.
CPC .......... *C12P 13/001* (2013.01); *C07C 227/06* (2013.01); *C07D 201/08* (2013.01); *C07D 223/10* (2013.01); *C12P 13/005* (2013.01); *C12P 13/02* (2013.01)

(58) Field of Classification Search
USPC ...... 435/136, 146, 142, 148, 71.1, 132, 141, 435/145, 155; 528/310, 323; 562/553
See application file for complete search history.

(56) References Cited

U.S. PATENT DOCUMENTS

| | | |
|---|---|---|
| 6,194,572 B1 | 2/2001 | Buijs |
| 2011/0171699 A1 | 7/2011 | Raemakers-Franken et al. |

FOREIGN PATENT DOCUMENTS

| | | |
|---|---|---|
| DE | 4 322 065 | 1/1995 |
| EP | 0628535 | 12/1994 |
| EP | 1586553 | 10/2005 |
| WO | 2005/068643 | 7/2005 |
| WO | WO 2007/050671 | 5/2007 |
| WO | WO 2008/000632 | 1/2008 |

OTHER PUBLICATIONS

International Search Report for PCT/NL2009/050117, mailed Oct. 26, 2009.
Reddy et al., "Expression, Purification, and Crystallization of Meso-Diaminopimelate Dehydrogenase from Corynebacterium Glutamicum", Proteins: Structure, Function and Genetics, vol. 25, No. 4, Jan. 1, 1996, pp. 514-516, XP001063203.
Ohshima et al., "Thermostable Amino Acid Dehydrogenases: Applications and Gene Cloning", Trends in Biotechnology, Elsevier Publications, Cambridge, GB, vol. 7, No. 8, Aug. 1, 1989, pp. 210-214, XP000037533.
Ayorinde et al., "Syntheses of 12-Aminododecanoic and 11-Aminoundecanoic Acids from Vernolic Acid," J. Am. Oil Chem. Soc., 74:531-538 (1997).
Gietz et al., "Transformation of yeast by the Liac/SS carrier DNA/PEG method," Methods Enzymology, 350:87-96 (2002).
Hiskey et al., "Azomethine Chemistry. I. Formation of Optically Active α-Amino Acids by Asymmetric Induction," J. Am. Chem. Soc., 83: 4798 (1961).
Jager et al., "Die Alanatreduktion von B-Carbonyl-oxalylsaure-estern," Chem. Ber., 92: 2492-2499 (1959).
Ogo et al., "pH-Dependent Chemoselective Synthesis of α-Amino Acids. Reductive Amination of α-Keto Acids with Ammonia Catalyzed by Acid-Stable Iridium Hydride Complexes in Water," J. Am. Chem. Soc., 126:3020-3021 (2004).
Stamos, "Aldehyde-Enamines From α-Oxocarboxylic Acids. A Facile and General Route to Aldehydes Via Decarboxylation of α-Oxocarboxylic Acids Carrying β-Hydrogens," Tetrahedron Lett., 23(4):459-462 (1982).
Virtanen and Berg "A New alpha-Aminodicarboxylic Acid, alpha-Aminopimelic Acid, in Green Plants," Acta Chemica Scandinavica., 6:1085-1086 (1954).

*Primary Examiner* — Kagnew H Gebreyesus
(74) *Attorney, Agent, or Firm* — Jones Day

(57) ABSTRACT

The invention relates to a method for preparing 6-aminocaproic acid (hereinafter also referred to as '6-ACA') using a biocatalyst. The invention further relates to a method for preparing e-caprolactam (hereafter referred to as 'caprolactam') by cyclising such 6-ACA. The invention further relates to a host cell, a micro-organism, or a polynucleotide which may be used in the preparation of 6-ACA or caprolactam.

15 Claims, No Drawings

SEQUENCE LISTING

```
<160> NUMBER OF SEQ ID NOS: 83

<210> SEQ ID NO 1
<211> LENGTH: 1362
<212> TYPE: DNA
<213> ORGANISM: Vibrio fluvialis
<220> FEATURE:
<221> NAME/KEY: CDS
<222> LOCATION: (1)..(1362)

<400> SEQUENCE: 1 atg aac aaa ccg caa agc tgg gaa gcc cgg gcc gag acc tat tcg ctc     48
Met Asn Lys Pro Gln Ser Trp Glu Ala Arg Ala Glu Thr Tyr Ser Leu
1               5                   10                  15 tat ggt ttc acc gac atg cct tcg ctg cat cag cgc ggc acg gtc gtc     96
Tyr Gly Phe Thr Asp Met Pro Ser Leu His Gln Arg Gly Thr Val Val
                20                  25                  30 gtg acc cat ggc gag gga ccc tat atc gtc gat gtg aat ggc cgg cgt    144
Val Thr His Gly Glu Gly Pro Tyr Ile Val Asp Val Asn Gly Arg Arg
            35                  40                  45 tat ctg gac gcc aac tcg ggc ctg tgg aac atg gtc gcg ggc ttt gac    192
Tyr Leu Asp Ala Asn Ser Gly Leu Trp Asn Met Val Ala Gly Phe Asp
        50                  55                  60 cac aag ggg ctg atc gac gcc gcc aag gcc caa tac gag cgt ttt ccc    240
His Lys Gly Leu Ile Asp Ala Ala Lys Ala Gln Tyr Glu Arg Phe Pro
65                  70                  75                  80 ggt tat cac gcc ttt ttc ggc cgc atg tcc gat cag acg gta atg ctg    288
Gly Tyr His Ala Phe Phe Gly Arg Met Ser Asp Gln Thr Val Met Leu
                85                  90                  95 tcg gaa aag ctg gtc gag gtg tcg ccc ttt gat tcg ggc cgg gtg ttc    336
Ser Glu Lys Leu Val Glu Val Ser Pro Phe Asp Ser Gly Arg Val Phe
                100                 105                 110 tat aca aac tcg ggg tcc gag gcg aat gac acc atg gtc aag atg cta    384
```

```
Tyr Thr Asn Ser Gly Ser Glu Ala Asn Asp Thr Met Val Lys Met Leu
            115                 120                 125 tgg ttc ctg cat gca gcc gag ggc aaa ccg caa aag cgc aag atc ctg       432
Trp Phe Leu His Ala Ala Glu Gly Lys Pro Gln Lys Arg Lys Ile Leu
130                 135                 140 acc cgc tgg aac gcc tat cac ggc gtg acc gcc gtt tcg gcc agc atg       480
Thr Arg Trp Asn Ala Tyr His Gly Val Thr Ala Val Ser Ala Ser Met
145                 150                 155                 160 acc ggc aag ccc tat aat tcg gtc ttt ggc ctg ccg ctg ccg ggc ttt       528
Thr Gly Lys Pro Tyr Asn Ser Val Phe Gly Leu Pro Leu Pro Gly Phe
                165                 170                 175 gtg cat ctg acc tgc ccg cat tac tgg cgc tat ggc gaa gag ggc gaa       576
Val His Leu Thr Cys Pro His Tyr Trp Arg Tyr Gly Glu Glu Gly Glu
            180                 185                 190 acc gaa gag cag ttc gtc gcc cgc ctc gcc cgc gag ctg gag gaa acg       624
Thr Glu Glu Gln Phe Val Ala Arg Leu Ala Arg Glu Leu Glu Glu Thr
        195                 200                 205 atc cag cgc gag ggc gcc gac acc atc gcc ggt ttc ttt gcc gaa ccg       672
Ile Gln Arg Glu Gly Ala Asp Thr Ile Ala Gly Phe Phe Ala Glu Pro
210                 215                 220 gtg atg ggc gcg ggc ggc gtg att ccc ccg gcc aag ggc tat ttc cag       720
Val Met Gly Ala Gly Gly Val Ile Pro Pro Ala Lys Gly Tyr Phe Gln
225                 230                 235                 240 gcg atc ctg cca atc ctg cgc aaa tat gac atc ccg gtc atc tcg gac       768
Ala Ile Leu Pro Ile Leu Arg Lys Tyr Asp Ile Pro Val Ile Ser Asp
                245                 250                 255 gag gtg atc tgc ggt ttc gga cgc acc ggt aac acc tgg ggc tgc gtg       816
Glu Val Ile Cys Gly Phe Gly Arg Thr Gly Asn Thr Trp Gly Cys Val
            260                 265                 270 acc tat gac ttt aca ccc gat gca atc atc tcg tcc aag aat ctt aca       864
Thr Tyr Asp Phe Thr Pro Asp Ala Ile Ile Ser Ser Lys Asn Leu Thr
        275                 280                 285 gcg ggc ttt ttc ccc atg ggg gcg gtg atc ctt ggc ccg gaa ctt tcc       912
Ala Gly Phe Phe Pro Met Gly Ala Val Ile Leu Gly Pro Glu Leu Ser
290                 295                 300 aaa cgg ctg gaa acc gca atc gag gcg atc gag gaa ttc ccc cat ggc       960
Lys Arg Leu Glu Thr Ala Ile Glu Ala Ile Glu Glu Phe Pro His Gly
305                 310                 315                 320 ttt acc gcc tcg ggc cat ccg gtc ggc tgt gct att gcg ctg aaa gca      1008
Phe Thr Ala Ser Gly His Pro Val Gly Cys Ala Ile Ala Leu Lys Ala
                325                 330                 335 atc gac gtg gtg atg aat gaa ggg ctg gct gag aac gtc cgc cgc ctt      1056
Ile Asp Val Val Met Asn Glu Gly Leu Ala Glu Asn Val Arg Arg Leu
            340                 345                 350 gcc ccc cgt ttc gag gaa agg ctg aaa cat atc gcc gag cgc ccg aac      1104
Ala Pro Arg Phe Glu Glu Arg Leu Lys His Ile Ala Glu Arg Pro Asn
        355                 360                 365 atc ggt gaa tat cgc ggc atc ggc ttc atg tgg gcg ctg gag gct gtc      1152
Ile Gly Glu Tyr Arg Gly Ile Gly Phe Met Trp Ala Leu Glu Ala Val
370                 375                 380 aag gac aag gca agc aag acg ccg ttc gac ggc aac ctg tcg gtc agc      1200
Lys Asp Lys Ala Ser Lys Thr Pro Phe Asp Gly Asn Leu Ser Val Ser
385                 390                 395                 400 gag cgt atc gcc aat acc tgc acc gat ctg ggg ctg att tgc cgg ccg      1248
Glu Arg Ile Ala Asn Thr Cys Thr Asp Leu Gly Leu Ile Cys Arg Pro
                405                 410                 415 ctt ggt cag tcc gtc gtc ctt tgt ccg ccc ttt atc ctg acc gag gcg      1296
Leu Gly Gln Ser Val Val Leu Cys Pro Pro Phe Ile Leu Thr Glu Ala
            420                 425                 430
```

```
cag atg gat gag atg ttc gat aaa ctc gaa aaa gcc ctt gat aag gtc      1344
Gln Met Asp Glu Met Phe Asp Lys Leu Glu Lys Ala Leu Asp Lys Val
        435                 440                 445 ttt gcc gag gtt gcc tga                                              1362
Phe Ala Glu Val Ala
    450

<210> SEQ ID NO 2
<211> LENGTH: 453
<212> TYPE: PRT
<213> ORGANISM: Vibrio fluvialis

<400> SEQUENCE: 2

Met Asn Lys Pro Gln Ser Trp Glu Ala Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Thr His Gly Glu Gly Pro Tyr Ile Val Asp Val Asn Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Phe Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Val Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Val His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Arg Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Met Gly Ala Val Ile Leu Gly Pro Glu Leu Ser
    290                 295                 300

Lys Arg Leu Glu Thr Ala Ile Glu Ala Ile Glu Glu Phe Pro His Gly
305                 310                 315                 320

Phe Thr Ala Ser Gly His Pro Val Gly Cys Ala Ile Ala Leu Lys Ala
                325                 330                 335
```

```
Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ala Val
    370                 375                 380

Lys Asp Lys Ala Ser Lys Thr Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450

<210> SEQ ID NO 3
<211> LENGTH: 1362
<212> TYPE: DNA
<213> ORGANISM: Artificial
<220> FEATURE:
<223> OTHER INFORMATION: Vibrio fluvialis JS17 omega-aminotransferase
      codon optimised gene

<400> SEQUENCE: 3
atgaataaac cacagtcttg ggaagctcgt gctgaaacct atagcctgta cggctttacc     60
gatatgccgt ctctgcacca gcgtggtact gtagtggtaa cgcacggtga gggcccgtac    120
atcgtggacg ttaatggccg ccgttacctg gatgcaaaca gcggcctgtg gaacatggtt    180
gcgggcttcg accacaaagg cctgatcgat gccgcaaaag cgcagtacga acgcttcccg    240
ggttatcacg cgttctttgg ccgtatgagc gaccagactg tgatgctgag cgaaaaactg    300
gttgaagtgt ccccgttcga tagcggtcgt gtctttttaca ctaactctgg cagcgaggct    360
aacgatacca tggttaagat gctgtggttc ctgcacgcag cggaaggcaa acctcagaaa    420
cgtaaaattc tgacccgttg gaacgcttat acggtgtga ctgctgtttc cgcatctatg    480
accggtaaac cgtataacag cgtgttcggt ctgccgctgc ctggcttcgt gcatctgacc    540
tgcccgcact actggcgtta tggtgaggaa ggcgaaactg aggaacagtt cgtggcgcgt    600
ctggctcgtg aactggaaga aaccattcaa cgcgaaggtg cagatactat cgcgggcttc    660
tttgcggagc ctgttatggg tgccggcggt gtgattccgc cggcgaaggg ctatttccag    720
gcaatcctgc cgatcctgcg caagtacgac attccggtta tttctgacga agtgatctgc    780
ggcttcggcc gcaccggtaa cacctggggc tgcgtgacgt atgacttcac tccggacgca    840
atcattagct ctaaaaacct gactgcgggt ttcttcccta tgggcgccgt aatcctgggc    900
ccagaactgt ctaagcgcct ggaaaccgcc atcgaggcaa tcgaagagtt cccgcacggt    960
ttcactgcta gcggccatcc ggtaggctgc gcaatcgcgc tgaaggcgat cgatgttgtc   1020
atgaacgagg gcctggcgga aaacgtgcgc gcgcctggcg cgcgttttga gaacgtctg   1080 aaacacattg ctgagcgccc gaacattggc gaatatcgcg gcatcggttt catgtgggcc   1140
ctggaagcag ttaaagataa agctagcaag accccgttcg acggcaacct gtccgtgagc   1200
gaacgtatcg ctaatacctg tacggacctg ggtctgatct gcgtccgct gggtcagtcc   1260 gtagttctgt gcccaccatt tatcctgacc gaagcgcaga tggatgaaat gttcgataaa   1320
```

```
ctggagaaag ctctggataa agtgttcgct gaagtcgcgt aa                         1362

<210> SEQ ID NO 4
<211> LENGTH: 1350
<212> TYPE: DNA
<213> ORGANISM: Bacillus weihenstephanensis
<220> FEATURE:
<221> NAME/KEY: CDS
<222> LOCATION: (1)..(1350)

<400> SEQUENCE: 4 gtg caa gcg acg gag caa aca caa agt ttg aaa aaa aca gat gaa aag      48
Val Gln Ala Thr Glu Gln Thr Gln Ser Leu Lys Lys Thr Asp Glu Lys
1               5                   10                  15 tac ctt tgg cat gcg atg aga gga gca gcc cct agt cca acg aat tta      96
Tyr Leu Trp His Ala Met Arg Gly Ala Ala Pro Ser Pro Thr Asn Leu
            20                  25                  30 att atc aca aaa gca gaa ggg gca tgg gtg acg gat att gat gga aac     144
Ile Ile Thr Lys Ala Glu Gly Ala Trp Val Thr Asp Ile Asp Gly Asn
        35                  40                  45 cgt tat tta gac ggt atg tcc ggt ctt tgg tgc gtg aat gtt ggg tat     192
Arg Tyr Leu Asp Gly Met Ser Gly Leu Trp Cys Val Asn Val Gly Tyr
    50                  55                  60 ggt cga aaa gaa ctt gca aga gcg gcg ttt gaa cag ctt gaa gaa atg     240
Gly Arg Lys Glu Leu Ala Arg Ala Ala Phe Glu Gln Leu Glu Glu Met
65                  70                  75                  80 ccg tat ttc cct ctg act caa agt cat gtt cct gct att aaa tta gca     288
Pro Tyr Phe Pro Leu Thr Gln Ser His Val Pro Ala Ile Lys Leu Ala
                85                  90                  95 gaa aaa ttg aat gaa tgg ctt gat gat gaa tac gtc att ttc ttt tct     336
Glu Lys Leu Asn Glu Trp Leu Asp Asp Glu Tyr Val Ile Phe Phe Ser
            100                 105                 110 aac agt gga tcg gaa gcg aat gaa aca gca ttt aaa att gct cgt caa     384
Asn Ser Gly Ser Glu Ala Asn Glu Thr Ala Phe Lys Ile Ala Arg Gln
        115                 120                 125 tat cat caa caa aaa ggt gat cat gga cgc tat aag ttt att tcc cgc     432
Tyr His Gln Gln Lys Gly Asp His Gly Arg Tyr Lys Phe Ile Ser Arg
    130                 135                 140 tac cgc gct tat cac ggt aac tca atg gga gct ctt gca gca aca ggt     480
Tyr Arg Ala Tyr His Gly Asn Ser Met Gly Ala Leu Ala Ala Thr Gly
145                 150                 155                 160 caa gca cag cga aag tat aaa tat gaa cca ctc ggg caa gga ttc ctg     528
Gln Ala Gln Arg Lys Tyr Lys Tyr Glu Pro Leu Gly Gln Gly Phe Leu
                165                 170                 175 cat gta gca ccg cct gat acg tat cga aat cca gag gat gtt cat aca     576
His Val Ala Pro Pro Asp Thr Tyr Arg Asn Pro Glu Asp Val His Thr
            180                 185                 190 ctg gca agt gct gag gaa atc gat cgt gtc atg aca tgg gag tta agc     624
Leu Ala Ser Ala Glu Glu Ile Asp Arg Val Met Thr Trp Glu Leu Ser
        195                 200                 205 caa aca gta gcc ggt gtg att atg gag cca atc att act ggg ggc gga     672
Gln Thr Val Ala Gly Val Ile Met Glu Pro Ile Ile Thr Gly Gly Gly
    210                 215                 220 att tta atg cct cct gat gga tat atg gga aaa gta aaa gaa att tgc     720
Ile Leu Met Pro Pro Asp Gly Tyr Met Gly Lys Val Lys Glu Ile Cys
225                 230                 235                 240 gag aag cac ggt gcg ttg ctc att tgt gat gaa gtt ata tgt gga ttt     768
Glu Lys His Gly Ala Leu Leu Ile Cys Asp Glu Val Ile Cys Gly Phe
                245                 250                 255 ggc cgg aca ggg aag cca ttt gga ttt atg aat tat ggc gtc aaa cca     816
Gly Arg Thr Gly Lys Pro Phe Gly Phe Met Asn Tyr Gly Val Lys Pro
```

-continued

```
                            260                 265                 270
gat atc att aca atg gca aaa ggt att aca agt gcg tat ctt cct ttg      864
Asp Ile Ile Thr Met Ala Lys Gly Ile Thr Ser Ala Tyr Leu Pro Leu
            275                 280                 285 tca gca aca gca gtt aga cga gag gtt tat gag gca ttc gta ggt agt      912
Ser Ala Thr Ala Val Arg Arg Glu Val Tyr Glu Ala Phe Val Gly Ser
290                 295                 300 gat gat tat gat cgc ttc cgc cat gta aat acg ttc gga ggg aat cct      960
Asp Asp Tyr Asp Arg Phe Arg His Val Asn Thr Phe Gly Gly Asn Pro
305                 310                 315                 320 gct gct tgc gct tta gct ttg aag aat tta gaa att atg gag aat gag     1008
Ala Ala Cys Ala Leu Ala Leu Lys Asn Leu Glu Ile Met Glu Asn Glu
                325                 330                 335 aaa ctc att gaa cgt tcc aaa gaa ttg ggt gaa cga ctg tta tat gag     1056
Lys Leu Ile Glu Arg Ser Lys Glu Leu Gly Glu Arg Leu Leu Tyr Glu
            340                 345                 350 cta gag gat gta aaa gag cat cca aac gta ggg gat gtt cgc gga aag     1104
Leu Glu Asp Val Lys Glu His Pro Asn Val Gly Asp Val Arg Gly Lys
        355                 360                 365 ggc ctt ctt tta ggc att gaa cta gtg gaa gat aag caa aca aaa gaa     1152
Gly Leu Leu Leu Gly Ile Glu Leu Val Glu Asp Lys Gln Thr Lys Glu
370                 375                 380 ccg gct tcc att gaa aag atg aac aaa gtc atc aat gct tgt aaa gaa     1200
Pro Ala Ser Ile Glu Lys Met Asn Lys Val Ile Asn Ala Cys Lys Glu
385                 390                 395                 400 aaa ggt cta att att ggt aaa aat ggt gac act gtc gca ggt tac aat     1248
Lys Gly Leu Ile Ile Gly Lys Asn Gly Asp Thr Val Ala Gly Tyr Asn
                405                 410                 415 aat att ttg cag ctt gca cct cca tta agc atc aca gag gaa gac ttt     1296
Asn Ile Leu Gln Leu Ala Pro Pro Leu Ser Ile Thr Glu Glu Asp Phe
            420                 425                 430 act ttt atc gtt aaa aca atg aaa gaa tgt tta tcc cgc att aac ggg     1344
Thr Phe Ile Val Lys Thr Met Lys Glu Cys Leu Ser Arg Ile Asn Gly
        435                 440                 445 cag taa                                                              1350
Gln
```

<210> SEQ ID NO 5
<211> LENGTH: 449
<212> TYPE: PRT
<213> ORGANISM: Bacillus weihenstephanensis

<400> SEQUENCE: 5

```
Val Gln Ala Thr Glu Gln Thr Gln Ser Leu Lys Lys Thr Asp Glu Lys
1               5                   10                  15

Tyr Leu Trp His Ala Met Arg Gly Ala Ala Pro Ser Pro Thr Asn Leu
            20                  25                  30

Ile Ile Thr Lys Ala Glu Gly Ala Trp Val Thr Asp Ile Asp Gly Asn
        35                  40                  45

Arg Tyr Leu Asp Gly Met Ser Gly Leu Trp Cys Val Asn Val Gly Tyr
    50                  55                  60

Gly Arg Lys Glu Leu Ala Arg Ala Ala Phe Glu Gln Leu Glu Glu Met
65                  70                  75                  80

Pro Tyr Phe Pro Leu Thr Gln Ser His Val Pro Ala Ile Lys Leu Ala
                85                  90                  95

Glu Lys Leu Asn Glu Trp Leu Asp Asp Glu Tyr Val Ile Phe Phe Ser
            100                 105                 110

Asn Ser Gly Ser Glu Ala Asn Glu Thr Ala Phe Lys Ile Ala Arg Gln
```

```
            115                 120                 125
Tyr His Gln Gln Lys Gly Asp His Gly Arg Tyr Lys Phe Ile Ser Arg
    130                 135                 140

Tyr Arg Ala Tyr His Gly Asn Ser Met Gly Ala Leu Ala Ala Thr Gly
145                 150                 155                 160

Gln Ala Gln Arg Lys Tyr Lys Tyr Glu Pro Leu Gly Gln Gly Phe Leu
                165                 170                 175

His Val Ala Pro Pro Asp Thr Tyr Arg Asn Pro Glu Asp Val His Thr
            180                 185                 190

Leu Ala Ser Ala Glu Glu Ile Asp Arg Val Met Thr Trp Glu Leu Ser
        195                 200                 205

Gln Thr Val Ala Gly Val Ile Met Glu Pro Ile Ile Thr Gly Gly Gly
    210                 215                 220

Ile Leu Met Pro Pro Asp Gly Tyr Met Gly Lys Val Lys Glu Ile Cys
225                 230                 235                 240

Glu Lys His Gly Ala Leu Leu Ile Cys Asp Glu Val Ile Cys Gly Phe
                245                 250                 255

Gly Arg Thr Gly Lys Pro Phe Gly Phe Met Asn Tyr Gly Val Lys Pro
            260                 265                 270

Asp Ile Ile Thr Met Ala Lys Gly Ile Thr Ser Ala Tyr Leu Pro Leu
        275                 280                 285

Ser Ala Thr Ala Val Arg Arg Glu Val Tyr Glu Ala Phe Val Gly Ser
    290                 295                 300

Asp Asp Tyr Asp Arg Phe Arg His Val Asn Thr Phe Gly Gly Asn Pro
305                 310                 315                 320

Ala Ala Cys Ala Leu Ala Leu Lys Asn Leu Glu Ile Met Glu Asn Glu
                325                 330                 335

Lys Leu Ile Glu Arg Ser Lys Glu Leu Gly Glu Arg Leu Leu Tyr Glu
            340                 345                 350

Leu Glu Asp Val Lys Glu His Pro Asn Val Gly Asp Val Arg Gly Lys
        355                 360                 365

Gly Leu Leu Leu Gly Ile Glu Leu Val Glu Asp Lys Gln Thr Lys Glu
    370                 375                 380

Pro Ala Ser Ile Glu Lys Met Asn Lys Val Ile Asn Ala Cys Lys Glu
385                 390                 395                 400

Lys Gly Leu Ile Ile Gly Lys Asn Gly Asp Thr Val Ala Gly Tyr Asn
                405                 410                 415

Asn Ile Leu Gln Leu Ala Pro Pro Leu Ser Ile Thr Glu Glu Asp Phe
            420                 425                 430

Thr Phe Ile Val Lys Thr Met Lys Glu Cys Leu Ser Arg Ile Asn Gly
        435                 440                 445

Gln
```

<210> SEQ ID NO 6
<211> LENGTH: 1350
<212> TYPE: DNA
<213> ORGANISM: Artificial
<220> FEATURE:
<223> OTHER INFORMATION: B. weihenstephanensis KBAB4 aminotransferase
      codon-optimised gene

<400> SEQUENCE: 6
atgcaggcta ccgaacaaac ccaatctctg aaaaagactg acgaaaaata tctgtggcac      60
gcgatgcgcg gtgcagctcc gtctccgacc aacctgatta ttaccaaagc tgaaggcgcg     120

-continued

```
tgggtgaccg acattgacgg taaccgttat ctggatggca tgagcggcct gtggtgtgtt    180
aatgtcggtt atggccgtaa ggagctggcg cgcgcggcat ttgaacaact ggaagaaatg    240
ccgtacttcc cgctgactca aagccatgtg ccggctatca aactggcgga aaaactgaac    300
gaatggctgg acgacgaata cgtgattttc ttctctaatt ctggctccga agcaaacgaa    360
accgcattca aaatcgcccg tcaatatcac cagcagaaag gtgaccacgg ccgctataaa    420
ttcatcagcc gttatcgtgc ataccatggt aattctatgg gtgcgctggc tgctaccggt    480
caggctcagc gcaaatacaa gtacgaaccg ctgggtcagg gttttctgca cgttgcacca    540
ccggatacct accgtaaccc ggaagacgtc cacaccctgg cttctgccga agaaatcgat    600
cgtgttatga cctgggagct gtcccagact gttgcgggtg ttatcatgga acctattatt    660
accggtggtg gcattctgat gccgccggac ggttatatgg gtaaagtcaa ggaaatctgc    720
gaaaaacacg gcgcgctgct gatctgcgat gaagttatct gtggcttcgg tcgcaccggc    780
aaaccatttg gcttcatgaa ttatggcgta aaacctgaca ttattaccat ggctaaaggc    840
attacttccg cttatctgcc gctgagcgcg accgcagttc gccgcgaagt ttatgaagcg    900
tttgttggtt ctgatgatta cgaccgtttc cgtcatgtaa acacgtttgg cggtaaccca    960
gcggcatgtg cgctggcgct gaaaaacctg gaaatcatgg aaaacgaaaa gctgatcgaa   1020
cgtagcaaag aactgggtga acgtctgctg tacgaactgg aagatgtcaa gaacacccg    1080
aacgtgggcg atgttcgcgg taaaggcctg ctgctgggta ttgaactggt tgaagacaaa   1140
cagaccaagg aaccggcttc cattgaaaag atgaacaaag tgattaacgc gtgcaaagag   1200
aaaggcctga tcattggtaa gaacggtgat accgtggcag ttataacaa cattctgcag   1260
ctggcgccgc tctctgagca tcactgaagaa gatttcacct tcatcgtcaa aactatgaag   1320
gagtgcctga ccgcatcaa tggtcagtaa                                     1350
```

<210> SEQ ID NO 7
<211> LENGTH: 1371
<212> TYPE: DNA
<213> ORGANISM: Pseudomonas aeruginosa
<220> FEATURE:
<221> NAME/KEY: CDS
<222> LOCATION: (1)..(1371)

<400> SEQUENCE: 7

```
atg aac agc caa atc acc aac gcc aag acc cgt gag tgg cag gcg ttg    48
Met Asn Ser Gln Ile Thr Asn Ala Lys Thr Arg Glu Trp Gln Ala Leu
1               5                   10                  15 agc cgc gac cac cat ctg ccg ccg ttc acc gac tac aag cag ttg aac    96
Ser Arg Asp His His Leu Pro Pro Phe Thr Asp Tyr Lys Gln Leu Asn
            20                  25                  30 gag aag ggc gcg cgg atc atc acc aag gcc gaa ggc gtc tat atc tgg   144
Glu Lys Gly Ala Arg Ile Ile Thr Lys Ala Glu Gly Val Tyr Ile Trp
        35                  40                  45 gac agc gag ggc aac aag atc ctc gat gcg atg gcc ggc ctc tgg tgc   192
Asp Ser Glu Gly Asn Lys Ile Leu Asp Ala Met Ala Gly Leu Trp Cys
    50                  55                  60 gtc aac gtc ggc tac ggc cgc gag gag ctg gtc cag gcc gcc acc cgg   240
Val Asn Val Gly Tyr Gly Arg Glu Glu Leu Val Gln Ala Ala Thr Arg
65                  70                  75                  80 cag atg cgc gag ttg ccg ttc tac aac ctg ttc ttc cag acc gcc cac   288
Gln Met Arg Glu Leu Pro Phe Tyr Asn Leu Phe Phe Gln Thr Ala His
                85                  90                  95 ccg ccg gtg gtc gag ctg gcc aag gcg atc gcc gac gtc gct ccg gaa   336
Pro Pro Val Val Glu Leu Ala Lys Ala Ile Ala Asp Val Ala Pro Glu
```

-continued

|     |     | 100 |     |     |     | 105 |     |     |     | 110 |     |     |      |
|-----|-----|-----|-----|-----|-----|-----|-----|-----|-----|-----|-----|-----|------|
| ggc | atg | aac | cac | gtg | ttc | ttc | acc | ggc | tcc | ggc | tcc | gag | gcc | aac | gac | 384  |
| Gly | Met | Asn | His | Val | Phe | Phe | Thr | Gly | Ser | Gly | Ser | Glu | Ala | Asn | Asp |      |
|     | 115 |     |     |     |     | 120 |     |     |     |     | 125 |     |     |     |     |      |

```
acc gtg ctg cgt atg gtc cgc cac tat tgg gcg acc aag ggc cag ccg       432
Thr Val Leu Arg Met Val Arg His Tyr Trp Ala Thr Lys Gly Gln Pro
    130                 135                 140 cag aag aaa gtg gtg atc ggc cgc tgg aac ggc tac cac ggc tcc acc       480
Gln Lys Lys Val Val Ile Gly Arg Trp Asn Gly Tyr His Gly Ser Thr
145                 150                 155                 160 gtc gcc ggc gtc agc ctg ggc ggc atg aag gcg ttg cat gag cag ggt       528
Val Ala Gly Val Ser Leu Gly Gly Met Lys Ala Leu His Glu Gln Gly
                165                 170                 175 gat ttc ccc atc ccg ggc atc gtc cac atc gcc cag ccc tac tgg tac       576
Asp Phe Pro Ile Pro Gly Ile Val His Ile Ala Gln Pro Tyr Trp Tyr
            180                 185                 190 ggc gag ggc ggc gac atg tcg ccg gac gag ttc ggc gtc tgg gcc gcc       624
Gly Glu Gly Gly Asp Met Ser Pro Asp Glu Phe Gly Val Trp Ala Ala
        195                 200                 205 gag cag ttg gag aag aag att ctc gaa gtg ggc gag gaa aac gtc gcc       672
Glu Gln Leu Glu Lys Lys Ile Leu Glu Val Gly Glu Glu Asn Val Ala
    210                 215                 220 gcc ttc atc gcc gag ccg atc cag ggc gcc ggc ggc gtg atc gtc ccg       720
Ala Phe Ile Ala Glu Pro Ile Gln Gly Ala Gly Gly Val Ile Val Pro
225                 230                 235                 240 ccg gac acc tac tgg ccg aag atc cgc gag atc ctc gcc aag tac gac       768
Pro Asp Thr Tyr Trp Pro Lys Ile Arg Glu Ile Leu Ala Lys Tyr Asp
                245                 250                 255 atc ctg ttc atc gcc gac gaa gtg atc tgc ggc ttc ggc cgt acc ggc       816
Ile Leu Phe Ile Ala Asp Glu Val Ile Cys Gly Phe Gly Arg Thr Gly
            260                 265                 270 gag tgg ttc ggc agc cag tac tac ggc aac gcc ccg gac ctg atg ccg       864
Glu Trp Phe Gly Ser Gln Tyr Tyr Gly Asn Ala Pro Asp Leu Met Pro
        275                 280                 285 atc gcc aag ggc ctc acc tcc ggc tac atc ccc atg ggc ggg gtg gtg       912
Ile Ala Lys Gly Leu Thr Ser Gly Tyr Ile Pro Met Gly Gly Val Val
    290                 295                 300 gtg cgc gac gag atc gtc gaa gtg ctc aac cag ggc ggc gag ttc tac       960
Val Arg Asp Glu Ile Val Glu Val Leu Asn Gln Gly Gly Glu Phe Tyr
305                 310                 315                 320 cac ggc ttc acc tat tcc ggt cac ccg gtg gcg gcc gcc gtg gcc ctg      1008
His Gly Phe Thr Tyr Ser Gly His Pro Val Ala Ala Ala Val Ala Leu
                325                 330                 335 gag aac atc cgc atc ctg cgc gaa gag aag atc atc gag aag gtg aag      1056
Glu Asn Ile Arg Ile Leu Arg Glu Glu Lys Ile Ile Glu Lys Val Lys
            340                 345                 350 gcg gaa acg gca ccg tat ttg cag aaa cgc tgg cag gag ctg gcc gac      1104
Ala Glu Thr Ala Pro Tyr Leu Gln Lys Arg Trp Gln Glu Leu Ala Asp
        355                 360                 365 cac ccg ttg gtg ggc gaa gcg cgc ggg gtc ggc atg gtc gcc gcc ctg      1152
His Pro Leu Val Gly Glu Ala Arg Gly Val Gly Met Val Ala Ala Leu
    370                 375                 380 gag ctg gtc aag aac aag aag acc cgc gag cgt ttc acc gac aag ggc      1200
Glu Leu Val Lys Asn Lys Lys Thr Arg Glu Arg Phe Thr Asp Lys Gly
385                 390                 395                 400 gtc ggg atg ctg tgc cgg gaa cat tgt ttc cgc aac ggt ttg atc atg      1248
Val Gly Met Leu Cys Arg Glu His Cys Phe Arg Asn Gly Leu Ile Met
                405                 410                 415 cgc gcg gtg ggc gac act atg att atc tcg ccg ccg ctg gtg atc gat      1296
```

```
Arg Ala Val Gly Asp Thr Met Ile Ile Ser Pro Pro Leu Val Ile Asp
                420                 425                 430 ccg tcg cag atc gat gag ttg atc acc ctg gcg cgc aag tgc ctc gat        1344
Pro Ser Gln Ile Asp Glu Leu Ile Thr Leu Ala Arg Lys Cys Leu Asp
        435                 440                 445 cag acc gcc gcc gcc gtc ctg gct tga                                    1371
Gln Thr Ala Ala Ala Val Leu Ala
    450                 455

<210> SEQ ID NO 8
<211> LENGTH: 456
<212> TYPE: PRT
<213> ORGANISM: Pseudomonas aeruginosa

<400> SEQUENCE: 8

Met Asn Ser Gln Ile Thr Asn Ala Lys Thr Arg Glu Trp Gln Ala Leu
1               5                   10                  15

Ser Arg Asp His His Leu Pro Pro Phe Thr Asp Tyr Lys Gln Leu Asn
                20                  25                  30

Glu Lys Gly Ala Arg Ile Ile Thr Lys Ala Glu Gly Val Tyr Ile Trp
            35                  40                  45

Asp Ser Glu Gly Asn Lys Ile Leu Asp Ala Met Ala Gly Leu Trp Cys
        50                  55                  60

Val Asn Val Gly Tyr Gly Arg Glu Glu Leu Val Gln Ala Ala Thr Arg
65                  70                  75                  80

Gln Met Arg Glu Leu Pro Phe Tyr Asn Leu Phe Gln Thr Ala His
                85                  90                  95

Pro Pro Val Val Glu Leu Ala Lys Ala Ile Ala Asp Val Ala Pro Glu
                100                 105                 110

Gly Met Asn His Val Phe Phe Thr Gly Ser Gly Ser Glu Ala Asn Asp
            115                 120                 125

Thr Val Leu Arg Met Val Arg His Tyr Trp Ala Thr Lys Gly Gln Pro
        130                 135                 140

Gln Lys Lys Val Val Ile Gly Arg Trp Asn Gly Tyr His Gly Ser Thr
145                 150                 155                 160

Val Ala Gly Val Ser Leu Gly Gly Met Lys Ala Leu His Glu Gln Gly
                165                 170                 175

Asp Phe Pro Ile Pro Gly Ile Val His Ile Ala Gln Pro Tyr Trp Tyr
            180                 185                 190

Gly Glu Gly Gly Asp Met Ser Pro Asp Glu Phe Gly Val Trp Ala Ala
        195                 200                 205

Glu Gln Leu Glu Lys Lys Ile Leu Glu Val Gly Glu Asn Val Ala
    210                 215                 220

Ala Phe Ile Ala Glu Pro Ile Gln Gly Ala Gly Gly Val Ile Val Pro
225                 230                 235                 240

Pro Asp Thr Tyr Trp Pro Lys Ile Arg Glu Ile Leu Ala Lys Tyr Asp
                245                 250                 255

Ile Leu Phe Ile Ala Asp Glu Val Ile Cys Gly Phe Gly Arg Thr Gly
            260                 265                 270

Glu Trp Phe Gly Ser Gln Tyr Tyr Gly Asn Ala Pro Asp Leu Met Pro
        275                 280                 285

Ile Ala Lys Gly Leu Thr Ser Gly Tyr Ile Pro Met Gly Gly Val Val
    290                 295                 300

Val Arg Asp Glu Ile Val Glu Val Leu Asn Gln Gly Gly Glu Phe Tyr
305                 310                 315                 320
```

-continued

```
            His Gly Phe Thr Tyr Ser Gly His Pro Val Ala Ala Val Ala Leu
                            325                 330                 335

Glu Asn Ile Arg Ile Leu Arg Glu Glu Lys Ile Ile Glu Lys Val Lys
                340                 345                 350

Ala Glu Thr Ala Pro Tyr Leu Gln Lys Arg Trp Gln Glu Leu Ala Asp
                    355                 360                 365

His Pro Leu Val Gly Glu Ala Arg Gly Val Gly Met Val Ala Ala Leu
                370                 375                 380

Glu Leu Val Lys Asn Lys Lys Thr Arg Glu Arg Phe Thr Asp Lys Gly
            385                 390                 395                 400

Val Gly Met Leu Cys Arg Glu His Cys Phe Arg Asn Gly Leu Ile Met
                            405                 410                 415

Arg Ala Val Gly Asp Thr Met Ile Ile Ser Pro Pro Leu Val Ile Asp
                        420                 425                 430

Pro Ser Gln Ile Asp Glu Leu Ile Thr Leu Ala Arg Lys Cys Leu Asp
                    435                 440                 445

Gln Thr Ala Ala Ala Val Leu Ala
                450                 455

<210> SEQ ID NO 9
<211> LENGTH: 70
<212> TYPE: DNA
<213> ORGANISM: Artificial
<220> FEATURE:
<223> OTHER INFORMATION: primer

<400> SEQUENCE: 9
ggggacaagt ttgtacaaaa aagcaggcta ggaggaatta accatgaaca gccaaatcac      60
caacgccaag                                                             70

<210> SEQ ID NO 10
<211> LENGTH: 49
<212> TYPE: DNA
<213> ORGANISM: Artificial
<220> FEATURE:
<223> OTHER INFORMATION: primer

<400> SEQUENCE: 10
ggggaccact ttgtacaaga aagctgggtt caagccagga cggcggcgg                  49

<210> SEQ ID NO 11
<211> LENGTH: 1365
<212> TYPE: DNA
<213> ORGANISM: Pseudomonas syringae
<220> FEATURE:
<221> NAME/KEY: CDS
<222> LOCATION: (1)..(1365)

<400> SEQUENCE: 11 atg agt gcc aac aac ccg caa acc ctc gaa tgg cag gcc ctg agc agc        48
Met Ser Ala Asn Asn Pro Gln Thr Leu Glu Trp Gln Ala Leu Ser Ser
1               5                   10                  15 gag cat cac ctg gca ccg ttc agc gac tac aaa caa ctg aaa gag aaa        96
Glu His His Leu Ala Pro Phe Ser Asp Tyr Lys Gln Leu Lys Glu Lys
                20                  25                  30 ggc ccg cgc atc atc acc cgt gcc gag ggc gtt tat ctg tgg gac agc       144
Gly Pro Arg Ile Ile Thr Arg Ala Glu Gly Val Tyr Leu Trp Asp Ser
            35                  40                  45 gag ggc aac aag atc ctc gat ggc atg tcc ggc ctg tgg tgc gtg gcc       192
Glu Gly Asn Lys Ile Leu Asp Gly Met Ser Gly Leu Trp Cys Val Ala
        50                  55                  60
```

```
atc ggt tat ggc cgc gaa gaa ctg gcc gac gca gcc agc aaa cag atg         240
Ile Gly Tyr Gly Arg Glu Glu Leu Ala Asp Ala Ala Ser Lys Gln Met
 65                  70                  75                  80 cgc gag ctg ccg tac tac aac ctg ttc ttc cag acc gcc cac ccg ccg         288
Arg Glu Leu Pro Tyr Tyr Asn Leu Phe Phe Gln Thr Ala His Pro Pro
                 85                  90                  95 gtg ctg gaa ctg gcc aag gcc atc tcc gac atc gct ccc gag ggc atg         336
Val Leu Glu Leu Ala Lys Ala Ile Ser Asp Ile Ala Pro Glu Gly Met
            100                 105                 110 aac cat gtg ttc ttc acc ggt tca ggc tct gaa ggc aat gac acg atg         384
Asn His Val Phe Phe Thr Gly Ser Gly Ser Glu Gly Asn Asp Thr Met
        115                 120                 125 ctg cgc atg gtt cgt cat tac tgg gcg ctg aaa ggc cag ccg aac aag         432
Leu Arg Met Val Arg His Tyr Trp Ala Leu Lys Gly Gln Pro Asn Lys
    130                 135                 140 aaa acc atc atc agc cgc gtc aat ggc tac cac ggc tcc acc gtc gcc         480
Lys Thr Ile Ile Ser Arg Val Asn Gly Tyr His Gly Ser Thr Val Ala
145                 150                 155                 160 ggt gcc agc ctg ggt ggc atg acc tac atg cac gaa cag ggc gac ctg         528
Gly Ala Ser Leu Gly Gly Met Thr Tyr Met His Glu Gln Gly Asp Leu
                165                 170                 175 ccg atc ccg ggg gtg gtg cac att cca cag cct tac tgg ttc ggc gaa         576
Pro Ile Pro Gly Val Val His Ile Pro Gln Pro Tyr Trp Phe Gly Glu
            180                 185                 190 ggc ggc gac atg acg ccg gac gag ttc ggc atc tgg gcg gcc gag caa         624
Gly Gly Asp Met Thr Pro Asp Glu Phe Gly Ile Trp Ala Ala Glu Gln
        195                 200                 205 ctg gaa aag aaa att ctc gag ctg ggc gtc gag aac gtc ggt gcg ttc         672
Leu Glu Lys Lys Ile Leu Glu Leu Gly Val Glu Asn Val Gly Ala Phe
    210                 215                 220 att gcc gag cca atc cag ggc gcg ggc ggt gtg att gtc ccg cct gat         720
Ile Ala Glu Pro Ile Gln Gly Ala Gly Gly Val Ile Val Pro Pro Asp
225                 230                 235                 240 tcc tac tgg ccg aag atc aag gaa atc ctt tcc cgc tac gac atc ctg         768
Ser Tyr Trp Pro Lys Ile Lys Glu Ile Leu Ser Arg Tyr Asp Ile Leu
                245                 250                 255 ttc gcc gcc gat gag gtg att tgt ggc ttc ggg cgt acc agt gag tgg         816
Phe Ala Ala Asp Glu Val Ile Cys Gly Phe Gly Arg Thr Ser Glu Trp
            260                 265                 270 ttc ggt agc gat ttc tat ggc ctc agg ccg gac atg atg acc atc gcc         864
Phe Gly Ser Asp Phe Tyr Gly Leu Arg Pro Asp Met Met Thr Ile Ala
        275                 280                 285 aaa ggc ctg acc tcc ggt tac gta ccg atg ggc ggc ctg atc gtg cgc         912
Lys Gly Leu Thr Ser Gly Tyr Val Pro Met Gly Gly Leu Ile Val Arg
    290                 295                 300 gat gaa atc gtt gcg gtg ctc aat gag ggt ggc gat ttc aat cac ggc         960
Asp Glu Ile Val Ala Val Leu Asn Glu Gly Gly Asp Phe Asn His Gly
305                 310                 315                 320 ttt acc tac tcc ggg cac ccg gtg gcg gcc gcg gtt gcg ctg gag aac        1008
Phe Thr Tyr Ser Gly His Pro Val Ala Ala Ala Val Ala Leu Glu Asn
                325                 330                 335 atc cgt atc ctg cgc gaa gaa aag atc gtc gaa cgg gtc agg tcg gaa        1056
Ile Arg Ile Leu Arg Glu Glu Lys Ile Val Glu Arg Val Arg Ser Glu
            340                 345                 350 acg gca ccg tat ttg caa aag cgt ttg cgt gag ttg agc gat cat ccg        1104
Thr Ala Pro Tyr Leu Gln Lys Arg Leu Arg Glu Leu Ser Asp His Pro
        355                 360                 365 ctg gtg ggc gaa gtc cgg ggt gtc ggg ctg ctc ggg gcc att gag ctg        1152
Leu Val Gly Glu Val Arg Gly Val Gly Leu Leu Gly Ala Ile Glu Leu
```

```
                370             375             380
gtg aag gac aag acc acc cgc gag cgc tat acc gac aag ggc gcg gga    1200
Val Lys Asp Lys Thr Thr Arg Glu Arg Tyr Thr Asp Lys Gly Ala Gly
385                 390                 395                 400 atg atc tgt cga acc ttc tgc ttc gac aat ggc ctg atc atg cgg gct    1248
Met Ile Cys Arg Thr Phe Cys Phe Asp Asn Gly Leu Ile Met Arg Ala
                405                 410                 415 gtg ggc gat acc atg atc att gcg ccg cca ctg gtg atc agt ttt gcg    1296
Val Gly Asp Thr Met Ile Ile Ala Pro Pro Leu Val Ile Ser Phe Ala
            420                 425                 430 caa atc gat gag ctg gta gag aag gcg cgc acg tgt ctg gat ctg acg    1344
Gln Ile Asp Glu Leu Val Glu Lys Ala Arg Thr Cys Leu Asp Leu Thr
        435                 440             445 ctg gcg gtg ttg cag ggc tga                                        1365
Leu Ala Val Leu Gln Gly
    450
```

<210> SEQ ID NO 12
<211> LENGTH: 454
<212> TYPE: PRT
<213> ORGANISM: Pseudomonas syringae

<400> SEQUENCE: 12

```
Met Ser Ala Asn Asn Pro Gln Thr Leu Glu Trp Gln Ala Leu Ser Ser
1               5                   10                  15

Glu His His Leu Ala Pro Phe Ser Asp Tyr Lys Gln Leu Lys Glu Lys
            20                  25                  30

Gly Pro Arg Ile Ile Thr Arg Ala Glu Gly Val Tyr Leu Trp Asp Ser
        35                  40                  45

Glu Gly Asn Lys Ile Leu Asp Gly Met Ser Gly Leu Trp Cys Val Ala
    50                  55                  60

Ile Gly Tyr Gly Arg Glu Glu Leu Ala Asp Ala Ala Ser Lys Gln Met
65                  70                  75                  80

Arg Glu Leu Pro Tyr Tyr Asn Leu Phe Phe Gln Thr Ala His Pro Pro
                85                  90                  95

Val Leu Glu Leu Ala Lys Ala Ile Ser Asp Ile Ala Pro Glu Gly Met
            100                 105                 110

Asn His Val Phe Phe Thr Gly Ser Gly Ser Glu Gly Asn Asp Thr Met
        115                 120                 125

Leu Arg Met Val Arg His Tyr Trp Ala Leu Lys Gly Gln Pro Asn Lys
    130                 135                 140

Lys Thr Ile Ile Ser Arg Val Asn Gly Tyr His Gly Ser Thr Val Ala
145                 150                 155                 160

Gly Ala Ser Leu Gly Gly Met Thr Tyr Met His Glu Gln Gly Asp Leu
                165                 170                 175

Pro Ile Pro Gly Val Val His Ile Pro Gln Pro Tyr Trp Phe Gly Glu
            180                 185                 190

Gly Gly Asp Met Thr Pro Asp Glu Phe Gly Ile Trp Ala Ala Glu Gln
        195                 200                 205

Leu Glu Lys Lys Ile Leu Glu Leu Gly Val Glu Asn Val Gly Ala Phe
    210                 215                 220

Ile Ala Glu Pro Ile Gln Gly Ala Gly Gly Val Ile Val Pro Pro Asp
225                 230                 235                 240

Ser Tyr Trp Pro Lys Ile Lys Glu Ile Leu Ser Arg Tyr Asp Ile Leu
                245                 250                 255

Phe Ala Ala Asp Glu Val Ile Cys Gly Phe Gly Arg Thr Ser Glu Trp
```

```
            260                 265                 270
Phe Gly Ser Asp Phe Tyr Gly Leu Arg Pro Asp Met Met Thr Ile Ala
        275                 280                 285
Lys Gly Leu Thr Ser Gly Tyr Val Pro Met Gly Gly Leu Ile Val Arg
        290                 295                 300
Asp Glu Ile Val Ala Val Leu Asn Glu Gly Gly Asp Phe Asn His Gly
305                 310                 315                 320
Phe Thr Tyr Ser Gly His Pro Val Ala Ala Val Ala Leu Glu Asn
                325                 330                 335
Ile Arg Ile Leu Arg Glu Glu Lys Ile Val Glu Arg Val Arg Ser Glu
            340                 345                 350
Thr Ala Pro Tyr Leu Gln Lys Arg Leu Arg Glu Leu Ser Asp His Pro
        355                 360                 365
Leu Val Gly Glu Val Arg Gly Val Gly Leu Leu Gly Ala Ile Glu Leu
        370                 375                 380
Val Lys Asp Lys Thr Thr Arg Glu Arg Tyr Thr Asp Lys Gly Ala Gly
385                 390                 395                 400
Met Ile Cys Arg Thr Phe Cys Phe Asp Asn Gly Leu Ile Met Arg Ala
                405                 410                 415
Val Gly Asp Thr Met Ile Ile Ala Pro Pro Leu Val Ile Ser Phe Ala
            420                 425                 430
Gln Ile Asp Glu Leu Val Glu Lys Ala Arg Thr Cys Leu Asp Leu Thr
        435                 440                 445
Leu Ala Val Leu Gln Gly
    450

<210> SEQ ID NO 13
<211> LENGTH: 1365
<212> TYPE: DNA
<213> ORGANISM: Artificial
<220> FEATURE:
<223> OTHER INFORMATION: Pseudomonas syringae codon optimised
      aminotransferase gene

<400> SEQUENCE: 13
atgtctgcta caatccaca aactctggaa tggcaggcac tgagctccga acatcacctg        60
gctccgttct ccgactacaa acaactgaaa gagaaaggcc gcgtatcat acccgcgct       120 gaaggtgtgt acctgtggga ttctgaaggc aacaaaattc tggacggtat gagcggcctg      180
tggtgcgtag caatcggtta tggccgtgaa gaactggctg acgcggcgag caaacagatg      240
cgtgaactgc gtattataa cctgttcttc caaaccgcac accgccggt ctggaactg        300 gctaaagcta tcagcgatat cgcaccggag ggcatgaatc acgtcttctt cactggttcc      360
ggtagcgaag caacgacac gatgctgcgc atggtacgtc actattgggc gctgaagggc       420
cagccgaaca agaaaacgat tatcagccgt gtaaacggtt atcacggcag caccgttgcg      480
ggtgcgagcc tggcggtat gacctacatg cacgaacagg gtgacctgcc gatcccgggt      540
gtagtgcaca ttccgcagcc gtattggttc ggtgaaggcg gtgacatgac gccggacgaa      600
ttcggcatct gggcggcaga gcagctggaa aagaaaatcc tggaactggg cgtggaaaac      660
gtcggcgcgt tcatcgcgga accgattcag ggcgcgggcg cgtaattgt tccgccggac      720 agctactggc caaaaatcaa agagatcctg tctcgttacg acatcctgtt cgccgcagac      780
gaagtgatct gcggttttgg ccgcacctct gaatggttcg ctccgactt ctacggtctg       840 cgtccggaca tgatgaccat cgccaaaggc ctgacctccg ttatgttcc tatgggtggc       900
```

```
ctgatcgtgc gcgacgaaat tgttgcggtt ctgaacgaag gcggcgattt caaccacggc      960
ttcacctatt ccggtcaccc agttgctgct gctgtagcac tggaaaacat ccgcatcctg     1020
cgtgaagaaa agatcgtaga acgcgtacgt tccgaaaccg caccttacct gcagaagcgc     1080
ctgcgcgaac tgagcgacca ccctctggta ggtgaagttc gcggcgtggg cctgctgggc     1140
gcgatcgagc tggtgaaaga caaaactacc cgtgaacgtt acaccgacaa aggcgcaggc     1200
atgatctgcc gtaccttttg cttcgataac ggtctgatca tgcgcgcagt cggtgatacc     1260
atgatcattg ctccgcctct ggttatttct tttgcccaga ttgatgagct ggtcgaaaaa     1320
gcgcgcactt gtctggatct gactctggct gttctgcagg gttaa                     1365
```

<210> SEQ ID NO 14
<211> LENGTH: 849
<212> TYPE: DNA
<213> ORGANISM: Bacillus subtilis
<220> FEATURE:
<221> NAME/KEY: CDS
<222> LOCATION: (1)..(849)

<400> SEQUENCE: 14

```
atg aag gtt tta gtc aat ggc cgg ctg att ggg cgc agt gaa gca tca        48
Met Lys Val Leu Val Asn Gly Arg Leu Ile Gly Arg Ser Glu Ala Ser
1               5                   10                  15 atc gat ttg gaa gat cgc ggt tat cag ttt ggt gac ggc atc tat gaa        96
Ile Asp Leu Glu Asp Arg Gly Tyr Gln Phe Gly Asp Gly Ile Tyr Glu
            20                  25                  30 gtg atc agg gtg tac aaa gga gta ttg ttc ggc tta cgt gag cat gca       144
Val Ile Arg Val Tyr Lys Gly Val Leu Phe Gly Leu Arg Glu His Ala
        35                  40                  45 gag cgt ttt ttc aga agt gct gct gaa atc gga att tca ctg cca ttc       192
Glu Arg Phe Phe Arg Ser Ala Ala Glu Ile Gly Ile Ser Leu Pro Phe
    50                  55                  60 agt ata gaa gat ctc gag tgg gac ctg caa aag ctt gta cag gaa aat       240
Ser Ile Glu Asp Leu Glu Trp Asp Leu Gln Lys Leu Val Gln Glu Asn
65                  70                  75                  80 gcg gtc agt gag gga gcg gta tac att cag aca aca aga ggt gtg gcc       288
Ala Val Ser Glu Gly Ala Val Tyr Ile Gln Thr Thr Arg Gly Val Ala
                85                  90                  95 ccg cga aaa cac cag tat gaa gcc ggc ctc gag ccg cag act act gcc       336
Pro Arg Lys His Gln Tyr Glu Ala Gly Leu Glu Pro Gln Thr Thr Ala
            100                 105                 110 tat acg ttt acg gtg aaa aaa ccg gag caa gag cag gca tac gga gtg       384
Tyr Thr Phe Thr Val Lys Lys Pro Glu Gln Glu Gln Ala Tyr Gly Val
        115                 120                 125 gcg gcc att aca gat gag gat ctt cgc tgg tta aga tgt gat atc aaa       432
Ala Ala Ile Thr Asp Glu Asp Leu Arg Trp Leu Arg Cys Asp Ile Lys
    130                 135                 140 agt ctg aat tta ctg tat aat gtc atg acg aag caa agg gcc tat gaa       480
Ser Leu Asn Leu Leu Tyr Asn Val Met Thr Lys Gln Arg Ala Tyr Glu
145                 150                 155                 160 gcc gga gca ttt gaa gcc att tta ctt agg gac ggc gtt gtt acg gag       528
Ala Gly Ala Phe Glu Ala Ile Leu Leu Arg Asp Gly Val Val Thr Glu
                165                 170                 175 ggt aca tcc tct aac gtt tat gcc gtt atc aac ggc aca gtg cga aca       576
Gly Thr Ser Ser Asn Val Tyr Ala Val Ile Asn Gly Thr Val Arg Thr
            180                 185                 190 cat ccg gct aat cgg ctc att ctc aat gga att aca cgg atg aat att       624
His Pro Ala Asn Arg Leu Ile Leu Asn Gly Ile Thr Arg Met Asn Ile
        195                 200                 205
```

```
tta gga ctg att gag aag aat ggg atc aaa ctg gat gag act cct gtc      672
Leu Gly Leu Ile Glu Lys Asn Gly Ile Lys Leu Asp Glu Thr Pro Val
    210                 215                 220 agt gaa gaa gag ttg aaa cag gcg gaa gag atc ttt att tcg tca acg      720
Ser Glu Glu Glu Leu Lys Gln Ala Glu Glu Ile Phe Ile Ser Ser Thr
225                 230                 235                 240 acg gca gaa att att ccg gtc gtg acg ctc gat gga caa tcg atc gga      768
Thr Ala Glu Ile Ile Pro Val Val Thr Leu Asp Gly Gln Ser Ile Gly
                245                 250                 255 agc ggg aaa ccc gga ccg gtg acc aaa cag ctt cag gct gct ttt caa      816
Ser Gly Lys Pro Gly Pro Val Thr Lys Gln Leu Gln Ala Ala Phe Gln
            260                 265                 270 gaa agc att caa cag gct gct agc att tca taa                          849
Glu Ser Ile Gln Gln Ala Ala Ser Ile Ser
        275                 280
```

<210> SEQ ID NO 15
<211> LENGTH: 282
<212> TYPE: PRT
<213> ORGANISM: Bacillus subtilis

<400> SEQUENCE: 15

```
Met Lys Val Leu Val Asn Gly Arg Leu Ile Gly Arg Ser Glu Ala Ser
1               5                   10                  15

Ile Asp Leu Glu Asp Arg Gly Tyr Gln Phe Gly Asp Gly Ile Tyr Glu
            20                  25                  30

Val Ile Arg Val Tyr Lys Gly Val Leu Phe Gly Leu Arg Glu His Ala
        35                  40                  45

Glu Arg Phe Phe Arg Ser Ala Ala Glu Ile Gly Ile Ser Leu Pro Phe
    50                  55                  60

Ser Ile Glu Asp Leu Glu Trp Asp Leu Gln Lys Leu Val Gln Glu Asn
65                  70                  75                  80

Ala Val Ser Glu Gly Ala Val Tyr Ile Gln Thr Thr Arg Gly Val Ala
                85                  90                  95

Pro Arg Lys His Gln Tyr Glu Ala Gly Leu Glu Pro Gln Thr Thr Ala
            100                 105                 110

Tyr Thr Phe Thr Val Lys Lys Pro Glu Gln Glu Gln Ala Tyr Gly Val
        115                 120                 125

Ala Ala Ile Thr Asp Glu Asp Leu Arg Trp Leu Arg Cys Asp Ile Lys
    130                 135                 140

Ser Leu Asn Leu Leu Tyr Asn Val Met Thr Lys Gln Arg Ala Tyr Glu
145                 150                 155                 160

Ala Gly Ala Phe Glu Ala Ile Leu Leu Arg Asp Gly Val Val Thr Glu
                165                 170                 175

Gly Thr Ser Ser Asn Val Tyr Ala Val Ile Asn Gly Thr Val Arg Thr
            180                 185                 190

His Pro Ala Asn Arg Leu Ile Leu Asn Gly Ile Thr Arg Met Asn Ile
        195                 200                 205

Leu Gly Leu Ile Glu Lys Asn Gly Ile Lys Leu Asp Glu Thr Pro Val
    210                 215                 220

Ser Glu Glu Glu Leu Lys Gln Ala Glu Glu Ile Phe Ile Ser Ser Thr
225                 230                 235                 240

Thr Ala Glu Ile Ile Pro Val Val Thr Leu Asp Gly Gln Ser Ile Gly
                245                 250                 255

Ser Gly Lys Pro Gly Pro Val Thr Lys Gln Leu Gln Ala Ala Phe Gln
            260                 265                 270
```

```
Glu Ser Ile Gln Gln Ala Ala Ser Ile Ser
            275                 280

<210> SEQ ID NO 16
<211> LENGTH: 1347
<212> TYPE: DNA
<213> ORGANISM: Bacillus subtilis
<220> FEATURE:
<221> NAME/KEY: CDS
<222> LOCATION: (1)..(1347)

<400> SEQUENCE: 16 atg act cat gat ttg ata gaa aaa agt aaa aag cac ctc tgg ctg cca       48
Met Thr His Asp Leu Ile Glu Lys Ser Lys Lys His Leu Trp Leu Pro
1               5                   10                  15 ttt acc caa atg aaa gat tat gat gaa aac ccc tta atc atc gaa agc       96
Phe Thr Gln Met Lys Asp Tyr Asp Glu Asn Pro Leu Ile Ile Glu Ser
                20                  25                  30 ggg act gga atc aaa gtc aaa gac ata aac ggc aag gaa tac tat gac      144
Gly Thr Gly Ile Lys Val Lys Asp Ile Asn Gly Lys Glu Tyr Tyr Asp
            35                  40                  45 ggt ttt tca tcg gtt tgg ctt aat gtc cac gga cac cgc aaa aaa gaa      192
Gly Phe Ser Ser Val Trp Leu Asn Val His Gly His Arg Lys Lys Glu
        50                  55                  60 cta gat gac gcc ata aaa aaa cag ctc gga aaa att gcg cac tcc acg      240
Leu Asp Asp Ala Ile Lys Lys Gln Leu Gly Lys Ile Ala His Ser Thr
65                  70                  75                  80 tta ttg ggc atg acc aat gtt cca gca acc cag ctt gcc gaa aca tta      288
Leu Leu Gly Met Thr Asn Val Pro Ala Thr Gln Leu Ala Glu Thr Leu
                85                  90                  95 atc gac atc agc cca aaa aag ctc acg cgg gtc ttt tat tca gac agc      336
Ile Asp Ile Ser Pro Lys Lys Leu Thr Arg Val Phe Tyr Ser Asp Ser
            100                 105                 110 ggc gca gag gcg atg gaa ata gcc cta aaa atg gcg ttt cag tat tgg      384
Gly Ala Glu Ala Met Glu Ile Ala Leu Lys Met Ala Phe Gln Tyr Trp
        115                 120                 125 aag aac atc ggg aag ccc gag aaa caa aaa ttc atc gca atg aaa aac      432
Lys Asn Ile Gly Lys Pro Glu Lys Gln Lys Phe Ile Ala Met Lys Asn
    130                 135                 140 ggg tat cac ggt gat acg att ggc gcc gtc agt gtc ggt tca att gag      480
Gly Tyr His Gly Asp Thr Ile Gly Ala Val Ser Val Gly Ser Ile Glu
145                 150                 155                 160 ctt ttt cac cac gta tac ggc ccg ttg atg ttc gag agt tac aag gcc      528
Leu Phe His His Val Tyr Gly Pro Leu Met Phe Glu Ser Tyr Lys Ala
                165                 170                 175 ccg att cct tat gtg tat cgt tct gaa agc ggt gat cct gat gag tgc      576
Pro Ile Pro Tyr Val Tyr Arg Ser Glu Ser Gly Asp Pro Asp Glu Cys
            180                 185                 190 cgt gat cag tgc ctc cga gag ctt gca cag ctg ctt gag gaa cat cat      624
Arg Asp Gln Cys Leu Arg Glu Leu Ala Gln Leu Leu Glu Glu His His
        195                 200                 205 gag gaa att gcc gcg ctt tcc att gaa tca atg gta caa ggc gcg tcc      672
Glu Glu Ile Ala Ala Leu Ser Ile Glu Ser Met Val Gln Gly Ala Ser
    210                 215                 220 ggt atg atc gtg atg ccg gaa gga tat ttg gca ggc gtg cgc gag cta      720
Gly Met Ile Val Met Pro Glu Gly Tyr Leu Ala Gly Val Arg Glu Leu
225                 230                 235                 240 tgt aca aca tac gat gtc tta atg atc gtt gat gaa gtc gct aca ggc      768
Cys Thr Thr Tyr Asp Val Leu Met Ile Val Asp Glu Val Ala Thr Gly
                245                 250                 255 ttt ggc cgt aca gga aaa atg ttt gcg tgc gag cac gag aat gtc cag      816
Phe Gly Arg Thr Gly Lys Met Phe Ala Cys Glu His Glu Asn Val Gln
```

```
            Phe Gly Arg Thr Gly Lys Met Phe Ala Cys Glu His Glu Asn Val Gln
                        260                 265                 270 cct gat ctg atg gct gcc ggt aaa ggc att aca gga ggc tat ttg cca        864
Pro Asp Leu Met Ala Ala Gly Lys Gly Ile Thr Gly Gly Tyr Leu Pro
            275                 280                 285 att gcc gtt acg ttt gcc act gaa gac atc tat aag gca ttc tat gat        912
Ile Ala Val Thr Phe Ala Thr Glu Asp Ile Tyr Lys Ala Phe Tyr Asp
        290                 295                 300 gat tat gaa aac cta aaa acc ttt ttc cat ggc cat tcc tat aca ggc        960
Asp Tyr Glu Asn Leu Lys Thr Phe Phe His Gly His Ser Tyr Thr Gly
305                 310                 315                 320 aat cag ctt ggc tgt gcg gtt gcg ctt gaa aat ctg gca tta ttt gaa       1008
Asn Gln Leu Gly Cys Ala Val Ala Leu Glu Asn Leu Ala Leu Phe Glu
                325                 330                 335 tct gaa aac att gtg gaa caa gta gcg gaa aaa agt aaa aag ctc cat       1056
Ser Glu Asn Ile Val Glu Gln Val Ala Glu Lys Ser Lys Lys Leu His
            340                 345                 350 ttt ctt ctt caa gat ctg cac gct ctt cct cat gtt ggg gat att cgg       1104
Phe Leu Leu Gln Asp Leu His Ala Leu Pro His Val Gly Asp Ile Arg
        355                 360                 365 cag ctt ggc ttt atg tgc ggt gca gag ctt gta cga tca aag gaa act       1152
Gln Leu Gly Phe Met Cys Gly Ala Glu Leu Val Arg Ser Lys Glu Thr
    370                 375                 380 aaa gaa cct tac ccg gct gat cgg cgg att gga tac aaa gtt tcc tta       1200
Lys Glu Pro Tyr Pro Ala Asp Arg Arg Ile Gly Tyr Lys Val Ser Leu
385                 390                 395                 400 aaa atg aga gag tta gga atg ctg aca aga ccg ctt ggg gac gtg att       1248
Lys Met Arg Glu Leu Gly Met Leu Thr Arg Pro Leu Gly Asp Val Ile
                405                 410                 415 gca ttt ctt cct cct ctt gcc agc aca gct gaa gag ctc tcg gaa atg       1296
Ala Phe Leu Pro Pro Leu Ala Ser Thr Ala Glu Glu Leu Ser Glu Met
            420                 425                 430 gtt gcc att atg aaa caa gcg atc cac gag gtt acg agc ctt gaa gat       1344
Val Ala Ile Met Lys Gln Ala Ile His Glu Val Thr Ser Leu Glu Asp
        435                 440                 445 tga                                                                    1347

<210> SEQ ID NO 17
<211> LENGTH: 448
<212> TYPE: PRT
<213> ORGANISM: Bacillus subtilis

<400> SEQUENCE: 17

Met Thr His Asp Leu Ile Glu Lys Ser Lys Lys His Leu Trp Leu Pro
1               5                   10                  15

Phe Thr Gln Met Lys Asp Tyr Asp Glu Asn Pro Leu Ile Ile Glu Ser
            20                  25                  30

Gly Thr Gly Ile Lys Val Lys Asp Ile Asn Gly Lys Glu Tyr Tyr Asp
        35                  40                  45

Gly Phe Ser Ser Val Trp Leu Asn Val His Gly His Arg Lys Lys Glu
    50                  55                  60

Leu Asp Asp Ala Ile Lys Lys Gln Leu Gly Lys Ile Ala His Ser Thr
65                  70                  75                  80

Leu Leu Gly Met Thr Asn Val Pro Ala Thr Gln Leu Ala Glu Thr Leu
                85                  90                  95

Ile Asp Ile Ser Pro Lys Lys Leu Thr Arg Val Phe Tyr Ser Asp Ser
            100                 105                 110

Gly Ala Glu Ala Met Glu Ile Ala Leu Lys Met Ala Phe Gln Tyr Trp
```

```
                115                 120                 125
Lys Asn Ile Gly Lys Pro Glu Lys Gln Lys Phe Ile Ala Met Lys Asn
    130                 135                 140

Gly Tyr His Gly Asp Thr Ile Gly Ala Val Ser Val Gly Ser Ile Glu
145                 150                 155                 160

Leu Phe His His Val Tyr Gly Pro Leu Met Phe Glu Ser Tyr Lys Ala
                165                 170                 175

Pro Ile Pro Tyr Val Tyr Arg Ser Glu Ser Gly Asp Pro Asp Glu Cys
            180                 185                 190

Arg Asp Gln Cys Leu Arg Glu Leu Ala Gln Leu Leu Glu Glu His His
        195                 200                 205

Glu Glu Ile Ala Ala Leu Ser Ile Glu Ser Met Val Gln Gly Ala Ser
    210                 215                 220

Gly Met Ile Val Met Pro Glu Gly Tyr Leu Ala Gly Val Arg Glu Leu
225                 230                 235                 240

Cys Thr Thr Tyr Asp Val Leu Met Ile Val Asp Glu Val Ala Thr Gly
                245                 250                 255

Phe Gly Arg Thr Gly Lys Met Phe Ala Cys Glu His Glu Asn Val Gln
            260                 265                 270

Pro Asp Leu Met Ala Ala Gly Lys Gly Ile Thr Gly Gly Tyr Leu Pro
        275                 280                 285

Ile Ala Val Thr Phe Ala Thr Glu Asp Ile Tyr Lys Ala Phe Tyr Asp
    290                 295                 300

Asp Tyr Glu Asn Leu Lys Thr Phe Phe His Gly His Ser Tyr Thr Gly
305                 310                 315                 320

Asn Gln Leu Gly Cys Ala Val Ala Leu Glu Asn Leu Ala Leu Phe Glu
                325                 330                 335

Ser Glu Asn Ile Val Glu Gln Val Ala Glu Lys Ser Lys Lys Leu His
            340                 345                 350

Phe Leu Leu Gln Asp Leu His Ala Leu Pro His Val Gly Asp Ile Arg
        355                 360                 365

Gln Leu Gly Phe Met Cys Gly Ala Glu Leu Val Arg Ser Lys Glu Thr
    370                 375                 380

Lys Glu Pro Tyr Pro Ala Asp Arg Arg Ile Gly Tyr Lys Val Ser Leu
385                 390                 395                 400

Lys Met Arg Glu Leu Gly Met Leu Thr Arg Pro Leu Gly Asp Val Ile
                405                 410                 415

Ala Phe Leu Pro Pro Leu Ala Ser Thr Ala Glu Glu Leu Ser Glu Met
            420                 425                 430

Val Ala Ile Met Lys Gln Ala Ile His Glu Val Thr Ser Leu Glu Asp
        435                 440                 445

<210> SEQ ID NO 18
<211> LENGTH: 1467
<212> TYPE: DNA
<213> ORGANISM: Rhodobacter sphaeroides
<220> FEATURE:
<221> NAME/KEY: CDS
<222> LOCATION: (1)..(1467)

<400> SEQUENCE: 18 atg ccc ggt tgc ggg ggc ttg ccc ggg aat gaa ccg aaa tgc gga cga      48
Met Pro Gly Cys Gly Gly Leu Pro Gly Asn Glu Pro Lys Cys Gly Arg
1               5                   10                  15 gag ggg agg tcg gcg atg acg cgg aat gac gcg acg aat gct gcc gga      96
Glu Gly Arg Ser Ala Met Thr Arg Asn Asp Ala Thr Asn Ala Ala Gly
```

|  |  |  |  |  |  |  |  |  |  |  |  |  |  |  |  |
|---|---|---|---|---|---|---|---|---|---|---|---|---|---|---|---|
|  |  |  | 20 |  |  |  | 25 |  |  |  | 30 |  |  |  |  |

```
gcg gtg ggc gcg gcg atg cgg gat cac atc ctc ttg cct gca cag gaa      144
Ala Val Gly Ala Ala Met Arg Asp His Ile Leu Leu Pro Ala Gln Glu
         35                  40                  45 atg gcg aag ctc ggc aag tcc gcg cag ccg gtg ctg act cat gcc gag      192
Met Ala Lys Leu Gly Lys Ser Ala Gln Pro Val Leu Thr His Ala Glu
 50                  55                  60 ggc atc tat gtc cat acc gag gac ggc cgc ctg atc gac ggg ccg          240
Gly Ile Tyr Val His Thr Glu Asp Gly Arg Arg Leu Ile Asp Gly Pro
 65                  70                  75                  80 gcg ggc atg tgg tgc gcg cag gtg ggc tac ggc cgc cgc gag atc gtc      288
Ala Gly Met Trp Cys Ala Gln Val Gly Tyr Gly Arg Arg Glu Ile Val
                     85                  90                  95 gat gcc atg gcg cat cag gcg atg gtg ctg ccc tat gcc tcg ccc tgg      336
Asp Ala Met Ala His Gln Ala Met Val Leu Pro Tyr Ala Ser Pro Trp
            100                 105                 110 tat atg gcc acg agc ccc gcg gcg cgg ctg gcg gag aag atc gcc acg      384
Tyr Met Ala Thr Ser Pro Ala Ala Arg Leu Ala Glu Lys Ile Ala Thr
        115                 120                 125 ctg acg ccg ggc gat ctc aac cgg atc ttt ttc acc acg ggc ggg tcg      432
Leu Thr Pro Gly Asp Leu Asn Arg Ile Phe Phe Thr Thr Gly Gly Ser
    130                 135                 140 acc gcg gtg gac agc gcg ctg cgc ttc tcg gaa ttc tac aac aac gtg      480
Thr Ala Val Asp Ser Ala Leu Arg Phe Ser Glu Phe Tyr Asn Asn Val
145                 150                 155                 160 ctg ggc cgg ccg cag aag aag cgc atc atc gtg cgc tac gac ggc tat      528
Leu Gly Arg Pro Gln Lys Lys Arg Ile Ile Val Arg Tyr Asp Gly Tyr
                165                 170                 175 cac ggc tcg acg gcg ctc acc gcc gcc tgc acc ggc cgc acc ggc aac      576
His Gly Ser Thr Ala Leu Thr Ala Ala Cys Thr Gly Arg Thr Gly Asn
            180                 185                 190 tgg ccg aac ttc gac atc gcg cag gac cgg atc tcg ttc ctc tcg agc      624
Trp Pro Asn Phe Asp Ile Ala Gln Asp Arg Ile Ser Phe Leu Ser Ser
        195                 200                 205 ccc aat ccg cgc cac gcc ggc aac cgc agc cag gag gcg ttc ctc gac      672
Pro Asn Pro Arg His Ala Gly Asn Arg Ser Gln Glu Ala Phe Leu Asp
    210                 215                 220 gat ctg gtg cag gaa ttc gag gac cgg atc gag agc ctc ggc ccc gac      720
Asp Leu Val Gln Glu Phe Glu Asp Arg Ile Glu Ser Leu Gly Pro Asp
225                 230                 235                 240 acg atc gcg gcc ttc ctg gcc gag ccg atc ctc gcc tcg ggc ggc gtc      768
Thr Ile Ala Ala Phe Leu Ala Glu Pro Ile Leu Ala Ser Gly Gly Val
                245                 250                 255 att att ccg ccc gca ggc tat cat gcg cgc ttc aag gcg atc tgc gag      816
Ile Ile Pro Pro Ala Gly Tyr His Ala Arg Phe Lys Ala Ile Cys Glu
            260                 265                 270 aag cac gac atc ctc tat atc tcg gac gag gtg gtg acg ggc ttc ggc      864
Lys His Asp Ile Leu Tyr Ile Ser Asp Glu Val Val Thr Gly Phe Gly
        275                 280                 285 cgt tgc ggc gag tgg ttc gcc tcg gag aag gtg ttc ggg gtg gtg ccg      912
Arg Cys Gly Glu Trp Phe Ala Ser Glu Lys Val Phe Gly Val Val Pro
    290                 295                 300 gac atc atc acc ttc gcc aag ggc gtg acc tcg ggc tat gtg ccg ctc      960
Asp Ile Ile Thr Phe Ala Lys Gly Val Thr Ser Gly Tyr Val Pro Leu
305                 310                 315                 320 ggc ggc ctt gcg atc tcc gag gcg gtg ctg gcg cgg atc tcg ggc gag     1008
Gly Gly Leu Ala Ile Ser Glu Ala Val Leu Ala Arg Ile Ser Gly Glu
                325                 330                 335 aat gcc aag gga agc tgg ttc acc aac ggc tat acc tac agc aat cag     1056
```

```
                Asn Ala Lys Gly Ser Trp Phe Thr Asn Gly Tyr Thr Tyr Ser Asn Gln
                            340                 345                 350 ccg gtg gcc tgc gcc gcg gcg ctt gcc aac atc gag ctg atg gag cgc          1104
Pro Val Ala Cys Ala Ala Ala Leu Ala Asn Ile Glu Leu Met Glu Arg
            355                 360                 365 gag ggc atc gtc gat cag gcg cgc gag atg gcg gac tat ttc gcc gcg          1152
Glu Gly Ile Val Asp Gln Ala Arg Glu Met Ala Asp Tyr Phe Ala Ala
370                 375                 380 gcg ctg gct tcg ctg cgc gat ctg ccg ggc gtg gcg gaa acc cgg tcg          1200
Ala Leu Ala Ser Leu Arg Asp Leu Pro Gly Val Ala Glu Thr Arg Ser
385                 390                 395                 400 gtg ggc ctc gtg ggt tgc gtg caa tgc ctg ctc gac ccg acc cgg gcg          1248
Val Gly Leu Val Gly Cys Val Gln Cys Leu Leu Asp Pro Thr Arg Ala
                405                 410                 415 gac ggc acg gcc gag gac aag gcc ttc acc ctg aag atc gac gag cgc          1296
Asp Gly Thr Ala Glu Asp Lys Ala Phe Thr Leu Lys Ile Asp Glu Arg
            420                 425                 430 tgc ttc gag ctc ggg ctg atc gtg cgc ccg ctg ggc gat ctc tgc gtg          1344
Cys Phe Glu Leu Gly Leu Ile Val Arg Pro Leu Gly Asp Leu Cys Val
        435                 440                 445 atc tcg ccg ccg ctc atc atc tcg cgc gcg cag atc gac gag atg gtc          1392
Ile Ser Pro Pro Leu Ile Ile Ser Arg Ala Gln Ile Asp Glu Met Val
450                 455                 460 gcg atc atg cgg cag gcc atc acc gaa gtg agc gcc gcc cac ggt ctg          1440
Ala Ile Met Arg Gln Ala Ile Thr Glu Val Ser Ala Ala His Gly Leu
465                 470                 475                 480 acc gcg aaa gaa ccg gcc gcc gtc tga                                      1467
Thr Ala Lys Glu Pro Ala Ala Val
                485

<210> SEQ ID NO 19
<211> LENGTH: 488
<212> TYPE: PRT
<213> ORGANISM: Rhodobacter sphaeroides

<400> SEQUENCE: 19

Met Pro Gly Cys Gly Gly Leu Pro Gly Asn Glu Pro Lys Cys Gly Arg
1               5                   10                  15

Glu Gly Arg Ser Ala Met Thr Arg Asn Asp Ala Thr Asn Ala Ala Gly
            20                  25                  30

Ala Val Gly Ala Ala Met Arg Asp His Ile Leu Leu Pro Ala Gln Glu
        35                  40                  45

Met Ala Lys Leu Gly Lys Ser Ala Gln Pro Val Leu Thr His Ala Glu
    50                  55                  60

Gly Ile Tyr Val His Thr Glu Asp Gly Arg Arg Leu Ile Asp Gly Pro
65                  70                  75                  80

Ala Gly Met Trp Cys Ala Gln Val Gly Tyr Gly Arg Arg Glu Ile Val
                85                  90                  95

Asp Ala Met Ala His Gln Ala Met Val Leu Pro Tyr Ala Ser Pro Trp
            100                 105                 110

Tyr Met Ala Thr Ser Pro Ala Ala Arg Leu Ala Glu Lys Ile Ala Thr
        115                 120                 125

Leu Thr Pro Gly Asp Leu Asn Arg Ile Phe Phe Thr Thr Gly Gly Ser
    130                 135                 140

Thr Ala Val Asp Ser Ala Leu Arg Phe Ser Glu Phe Tyr Asn Asn Val
145                 150                 155                 160

Leu Gly Arg Pro Gln Lys Lys Arg Ile Ile Val Arg Tyr Asp Gly Tyr
                165                 170                 175
```

-continued

```
His Gly Ser Thr Ala Leu Thr Ala Ala Cys Thr Gly Arg Thr Gly Asn
            180                 185                 190

Trp Pro Asn Phe Asp Ile Ala Gln Asp Arg Ile Ser Phe Leu Ser Ser
        195                 200                 205

Pro Asn Pro Arg His Ala Gly Asn Arg Ser Gln Glu Ala Phe Leu Asp
    210                 215                 220

Asp Leu Val Gln Glu Phe Glu Asp Arg Ile Glu Ser Leu Gly Pro Asp
225                 230                 235                 240

Thr Ile Ala Ala Phe Leu Ala Glu Pro Ile Leu Ala Ser Gly Gly Val
                245                 250                 255

Ile Ile Pro Pro Ala Gly Tyr His Ala Arg Phe Lys Ala Ile Cys Glu
            260                 265                 270

Lys His Asp Ile Leu Tyr Ile Ser Asp Glu Val Val Thr Gly Phe Gly
        275                 280                 285

Arg Cys Gly Glu Trp Phe Ala Ser Glu Lys Val Phe Gly Val Val Pro
    290                 295                 300

Asp Ile Ile Thr Phe Ala Lys Gly Val Thr Ser Gly Tyr Val Pro Leu
305                 310                 315                 320

Gly Gly Leu Ala Ile Ser Glu Ala Val Leu Ala Arg Ile Ser Gly Glu
                325                 330                 335

Asn Ala Lys Gly Ser Trp Phe Thr Asn Gly Tyr Thr Tyr Ser Asn Gln
            340                 345                 350

Pro Val Ala Cys Ala Ala Ala Leu Ala Asn Ile Glu Leu Met Glu Arg
        355                 360                 365

Glu Gly Ile Val Asp Gln Ala Arg Glu Met Ala Asp Tyr Phe Ala Ala
    370                 375                 380

Ala Leu Ala Ser Leu Arg Asp Leu Pro Gly Val Ala Glu Thr Arg Ser
385                 390                 395                 400

Val Gly Leu Val Gly Cys Val Gln Cys Leu Leu Asp Pro Thr Arg Ala
                405                 410                 415

Asp Gly Thr Ala Glu Asp Lys Ala Phe Thr Leu Lys Ile Asp Glu Arg
            420                 425                 430

Cys Phe Glu Leu Gly Leu Ile Val Arg Pro Leu Gly Asp Leu Cys Val
        435                 440                 445

Ile Ser Pro Pro Leu Ile Ile Ser Arg Ala Gln Ile Asp Glu Met Val
    450                 455                 460

Ala Ile Met Arg Gln Ala Ile Thr Glu Val Ser Ala Ala His Gly Leu
465                 470                 475                 480

Thr Ala Lys Glu Pro Ala Ala Val
                485

<210> SEQ ID NO 20
<211> LENGTH: 837
<212> TYPE: DNA
<213> ORGANISM: Legionella pneumophila
<220> FEATURE:
<221> NAME/KEY: CDS
<222> LOCATION: (1)..(837)

<400> SEQUENCE: 20 atg agt atc gca ttt gtt aac ggc aag tat tgt tgt caa tct gaa gca       48
Met Ser Ile Ala Phe Val Asn Gly Lys Tyr Cys Cys Gln Ser Glu Ala
1               5                   10                  15 aaa att tca ata ttt gat cga ggg ttt ctt ttt ggt gac tcg gtt tat       96
Lys Ile Ser Ile Phe Asp Arg Gly Phe Leu Phe Gly Asp Ser Val Tyr
            20                  25                  30
```

-continued

```
gaa gtg ctg cct gtt tac cat ggg cag cct tac ttt gta gac caa cat      144
Glu Val Leu Pro Val Tyr His Gly Gln Pro Tyr Phe Val Asp Gln His
        35                  40                  45 ctt gac cga tta ttc tca aat atg aaa aaa att aag atg att ata cca      192
Leu Asp Arg Leu Phe Ser Asn Met Lys Lys Ile Lys Met Ile Ile Pro
    50                  55                  60 aat tat gat tgg cat ggt tta att cat aga cta ata tca gaa aat aat      240
Asn Tyr Asp Trp His Gly Leu Ile His Arg Leu Ile Ser Glu Asn Asn
65                  70                  75                  80 ggc ggt aat tta caa gta tat atc caa gtc aca cga ggg aat caa ggg      288
Gly Gly Asn Leu Gln Val Tyr Ile Gln Val Thr Arg Gly Asn Gln Gly
                85                  90                  95 gtg cgc aag cat gat atc cct act tcc atc aca cct tct gtt atc gca      336
Val Arg Lys His Asp Ile Pro Thr Ser Ile Thr Pro Ser Val Ile Ala
            100                 105                 110 ttc act atg cat aat cca ttt ccc acc ctc gaa gat aag gaa cag gga      384
Phe Thr Met His Asn Pro Phe Pro Thr Leu Glu Asp Lys Glu Gln Gly
        115                 120                 125 atg tca gca aaa ctg gtt gaa gat ttt cgg tgg atg aga tgt gat ata      432
Met Ser Ala Lys Leu Val Glu Asp Phe Arg Trp Met Arg Cys Asp Ile
    130                 135                 140 aaa act act tct tta att gcc aat ata tta ctg aat gat gag gct gta      480
Lys Thr Thr Ser Leu Ile Ala Asn Ile Leu Leu Asn Asp Glu Ala Val
145                 150                 155                 160 tct gca gga ttc cac act gca att ctt gcc cgg aac ggt cta att aca      528
Ser Ala Gly Phe His Thr Ala Ile Leu Ala Arg Asn Gly Leu Ile Thr
                165                 170                 175 gag gga agt agt acc aac gta ttt att gtc gca cag gat ggt gtt att      576
Glu Gly Ser Ser Thr Asn Val Phe Ile Val Ala Gln Asp Gly Val Ile
            180                 185                 190 aag aca cca ccc atg aat aat ttc tgt tta cca gga att act cgg caa      624
Lys Thr Pro Pro Met Asn Asn Phe Cys Leu Pro Gly Ile Thr Arg Gln
        195                 200                 205 gtt gtt att gaa ata att aaa aaa tta gat tta aag ttc aga gaa ata      672
Val Val Ile Glu Ile Ile Lys Lys Leu Asp Leu Lys Phe Arg Glu Ile
    210                 215                 220 gaa att agc att tca gag ctt ttt tct gct cag gaa gtt tgg ata aca      720
Glu Ile Ser Ile Ser Glu Leu Phe Ser Ala Gln Glu Val Trp Ile Thr
225                 230                 235                 240 agt acg aca aaa gaa gta ttc cct att aca aag att aat gac tct ttg      768
Ser Thr Thr Lys Glu Val Phe Pro Ile Thr Lys Ile Asn Asp Ser Leu
                245                 250                 255 att aat ggc gga aaa gtt ggc gaa tat tgg cgg ata att aat gat tcc      816
Ile Asn Gly Gly Lys Val Gly Glu Tyr Trp Arg Ile Ile Asn Asp Ser
            260                 265                 270 tac caa caa cta gta aac taa                                          837
Tyr Gln Gln Leu Val Asn
        275

<210> SEQ ID NO 21
<211> LENGTH: 278
<212> TYPE: PRT
<213> ORGANISM: Legionella pneumophila

<400> SEQUENCE: 21

Met Ser Ile Ala Phe Val Asn Gly Lys Tyr Cys Cys Gln Ser Glu Ala
1               5                   10                  15

Lys Ile Ser Ile Phe Asp Arg Gly Phe Leu Phe Gly Asp Ser Val Tyr
            20                  25                  30
```

```
Glu Val Leu Pro Val Tyr His Gly Gln Pro Tyr Phe Val Asp Gln His
        35                  40                  45

Leu Asp Arg Leu Phe Ser Asn Met Lys Lys Ile Lys Met Ile Ile Pro
 50                  55                  60

Asn Tyr Asp Trp His Gly Leu Ile His Arg Leu Ile Ser Glu Asn Asn
 65                  70                  75                  80

Gly Gly Asn Leu Gln Val Tyr Ile Gln Val Thr Arg Gly Asn Gln Gly
                 85                  90                  95

Val Arg Lys His Asp Ile Pro Thr Ser Ile Thr Pro Ser Val Ile Ala
            100                 105                 110

Phe Thr Met His Asn Pro Phe Pro Thr Leu Glu Asp Lys Glu Gln Gly
            115                 120                 125

Met Ser Ala Lys Leu Val Glu Asp Phe Arg Trp Met Arg Cys Asp Ile
130                 135                 140

Lys Thr Thr Ser Leu Ile Ala Asn Ile Leu Leu Asn Asp Glu Ala Val
145                 150                 155                 160

Ser Ala Gly Phe His Thr Ala Ile Leu Ala Arg Asn Gly Leu Ile Thr
                165                 170                 175

Glu Gly Ser Ser Thr Asn Val Phe Ile Val Ala Gln Asp Gly Val Ile
            180                 185                 190

Lys Thr Pro Pro Met Asn Asn Phe Cys Leu Pro Gly Ile Thr Arg Gln
            195                 200                 205

Val Val Ile Glu Ile Ile Lys Lys Leu Asp Leu Lys Phe Arg Glu Ile
        210                 215                 220

Glu Ile Ser Ile Ser Glu Leu Phe Ser Ala Gln Glu Val Trp Ile Thr
225                 230                 235                 240

Ser Thr Thr Lys Glu Val Phe Pro Ile Thr Lys Ile Asn Asp Ser Leu
                245                 250                 255

Ile Asn Gly Gly Lys Val Gly Glu Tyr Trp Arg Ile Ile Asn Asp Ser
            260                 265                 270

Tyr Gln Gln Leu Val Asn
        275

<210> SEQ ID NO 22
<211> LENGTH: 861
<212> TYPE: DNA
<213> ORGANISM: Nitrosomonas europaea
<220> FEATURE:
<221> NAME/KEY: CDS
<222> LOCATION: (1)..(861)

<400> SEQUENCE: 22 atg att tac ctc aat ggc aaa ttt ctg ccg atg gaa cag gct acc gtt      48
Met Ile Tyr Leu Asn Gly Lys Phe Leu Pro Met Glu Gln Ala Thr Val
 1               5                  10                  15 cca gtg ctg gat aga ggc ttc atc ttc ggt gat ggt gtc tat gaa gtc      96
Pro Val Leu Asp Arg Gly Phe Ile Phe Gly Asp Gly Val Tyr Glu Val
             20                  25                  30 ata ccg gtt tat tca cgt aaa ccg ttc cgg ctg ggc gaa cat ctt tcc     144
Ile Pro Val Tyr Ser Arg Lys Pro Phe Arg Leu Gly Glu His Leu Ser
         35                  40                  45 cgg ctg cag cac agt ctg gat ggc ata cgt ctc cag aat ccg cac act     192
Arg Leu Gln His Ser Leu Asp Gly Ile Arg Leu Gln Asn Pro His Thr
     50                  55                  60 gaa gaa caa tgg gct ggt ctg atc gaa cgc atc atc gag ctg aat gaa     240
Glu Glu Gln Trp Ala Gly Leu Ile Glu Arg Ile Ile Glu Leu Asn Glu
 65                  70                  75                  80
```

| | | | | | | | | | | | | | | | | |
|---|---|---|---|---|---|---|---|---|---|---|---|---|---|---|---|---|
| ggt | gat | gat | cag | tac | ctt | tac | ctg | cac | att | aca | cgc | ggg | gtg | gca | aaa | 288 |
| Gly | Asp | Asp | Gln | Tyr | Leu | Tyr | Leu | His | Ile | Thr | Arg | Gly | Val | Ala | Lys | |
| | | | 85 | | | | | 90 | | | | | 95 | | | |
| cgt | gac | cat | gcc | ttt | cct | cgc | gaa | gta | acg | ccc | act | gtc | ttc | atc | atg | 336 |
| Arg | Asp | His | Ala | Phe | Pro | Arg | Glu | Val | Thr | Pro | Thr | Val | Phe | Ile | Met | |
| | | | 100 | | | | | 105 | | | | | 110 | | | |
| agc | aac | ccg | ctt | ccg | gct | cca | cct | gca | aaa | ttg | ctc | gtt | tcc | gga | gtt | 384 |
| Ser | Asn | Pro | Leu | Pro | Ala | Pro | Pro | Ala | Lys | Leu | Leu | Val | Ser | Gly | Val | |
| | | | 115 | | | | | 120 | | | | | 125 | | | |
| tca | gcg | att | acc | gcc | agg | gat | aat | cgc | tgg | ggg | cgc | tgt | gat | atc | aaa | 432 |
| Ser | Ala | Ile | Thr | Ala | Arg | Asp | Asn | Arg | Trp | Gly | Arg | Cys | Asp | Ile | Lys | |
| | 130 | | | | | 135 | | | | | 140 | | | | | |
| gcc | att | tca | ctg | ttg | cca | aat | atc | tta | ttg | cgc | cag | ctt | gcc | gtg | gac | 480 |
| Ala | Ile | Ser | Leu | Leu | Pro | Asn | Ile | Leu | Leu | Arg | Gln | Leu | Ala | Val | Asp | |
| 145 | | | | | 150 | | | | | 155 | | | | | 160 | |
| gca | caa | gcc | atg | gaa | acg | atc | ctg | tta | cgc | gat | ggt | ctg | ttg | acc | gaa | 528 |
| Ala | Gln | Ala | Met | Glu | Thr | Ile | Leu | Leu | Arg | Asp | Gly | Leu | Leu | Thr | Glu | |
| | | | 165 | | | | | 170 | | | | | 175 | | | |
| ggg | gcc | gcc | agc | aat | att | ttc | atc | gta | aaa | gac | gac | ctg | ctg | ctg | acc | 576 |
| Gly | Ala | Ala | Ser | Asn | Ile | Phe | Ile | Val | Lys | Asp | Asp | Leu | Leu | Leu | Thr | |
| | | | 180 | | | | | 185 | | | | | 190 | | | |
| ccc | ccc | aaa | gat | cac | cgt | ata | ttg | cct | ggc | att | act | tat | gat | gta | gta | 624 |
| Pro | Pro | Lys | Asp | His | Arg | Ile | Leu | Pro | Gly | Ile | Thr | Tyr | Asp | Val | Val | |
| | | | 195 | | | | | 200 | | | | | 205 | | | |
| ctg | gaa | ctg | gct | gaa | aca | cat | ggt | gtt | cca | cat | gcg | aca | aga | gaa | ata | 672 |
| Leu | Glu | Leu | Ala | Glu | Thr | His | Gly | Val | Pro | His | Ala | Thr | Arg | Glu | Ile | |
| | | | 210 | | | | | 215 | | | | | 220 | | | |
| tca | gag | ctt | gag | tta | cgt | act | gca | cgg | gaa | atc | atg | ctg | act | tct | tcc | 720 |
| Ser | Glu | Leu | Glu | Leu | Arg | Thr | Ala | Arg | Glu | Ile | Met | Leu | Thr | Ser | Ser | |
| 225 | | | | | 230 | | | | | 235 | | | | | 240 | |
| acc | aaa | gaa | att | ctc | ccg | atc | aca | cag | ctg | gat | gga | caa | ccg | atc | ggt | 768 |
| Thr | Lys | Glu | Ile | Leu | Pro | Ile | Thr | Gln | Leu | Asp | Gly | Gln | Pro | Ile | Gly | |
| | | | 245 | | | | | 250 | | | | | 255 | | | |
| aat | ggc | acc | cca | ggg | cca | gta | ttt | cag | caa | ctg | gat | cgg | ctc | tat | cag | 816 |
| Asn | Gly | Thr | Pro | Gly | Pro | Val | Phe | Gln | Gln | Leu | Asp | Arg | Leu | Tyr | Gln | |
| | | | 260 | | | | | 265 | | | | | 270 | | | |
| gca | tat | aag | ctg | gaa | gtc | atg | cgc | ggg | cat | gct | cca | cgc | cag | taa | | 861 |
| Ala | Tyr | Lys | Leu | Glu | Val | Met | Arg | Gly | His | Ala | Pro | Arg | Gln | | | |
| | | 275 | | | | | 280 | | | | | 285 | | | | |

<210> SEQ ID NO 23
<211> LENGTH: 286
<212> TYPE: PRT
<213> ORGANISM: Nitrosomonas europaea

<400> SEQUENCE: 23

Met Ile Tyr Leu Asn Gly Lys Phe Leu Pro Met Glu Gln Ala Thr Val
1               5                   10                  15

Pro Val Leu Asp Arg Gly Phe Ile Phe Gly Asp Gly Val Tyr Glu Val
            20                  25                  30

Ile Pro Val Tyr Ser Arg Lys Pro Phe Arg Leu Gly Glu His Leu Ser
        35                  40                  45

Arg Leu Gln His Ser Leu Asp Gly Ile Arg Leu Gln Asn Pro His Thr
    50                  55                  60

Glu Glu Gln Trp Ala Gly Leu Ile Glu Arg Ile Glu Leu Asn Glu
65                  70                  75                  80

Gly Asp Asp Gln Tyr Leu Tyr Leu His Ile Thr Arg Gly Val Ala Lys
                85                  90                  95

Arg Asp His Ala Phe Pro Arg Glu Val Thr Pro Thr Val Phe Ile Met

```
                100              105              110
Ser Asn Pro Leu Pro Ala Pro Ala Lys Leu Leu Val Ser Gly Val
        115              120              125
Ser Ala Ile Thr Ala Arg Asp Asn Arg Trp Gly Arg Cys Asp Ile Lys
130              135              140
Ala Ile Ser Leu Leu Pro Asn Ile Leu Leu Arg Gln Leu Ala Val Asp
145              150              155              160
Ala Gln Ala Met Glu Thr Ile Leu Leu Arg Asp Gly Leu Leu Thr Glu
                165              170              175
Gly Ala Ala Ser Asn Ile Phe Ile Val Lys Asp Asp Leu Leu Leu Thr
            180              185              190
Pro Pro Lys Asp His Arg Ile Leu Pro Gly Ile Thr Tyr Asp Val Val
        195              200              205
Leu Glu Leu Ala Glu Thr His Gly Val Pro His Ala Thr Arg Glu Ile
        210              215              220
Ser Glu Leu Glu Leu Arg Thr Ala Arg Glu Ile Met Leu Thr Ser Ser
225              230              235              240
Thr Lys Glu Ile Leu Pro Ile Thr Gln Leu Asp Gly Gln Pro Ile Gly
                245              250              255
Asn Gly Thr Pro Gly Pro Val Phe Gln Gln Leu Asp Arg Leu Tyr Gln
            260              265              270
Ala Tyr Lys Leu Glu Val Met Arg Gly His Ala Pro Arg Gln
        275              280              285

<210> SEQ ID NO 24
<211> LENGTH: 1293
<212> TYPE: DNA
<213> ORGANISM: Neisseria gonorrhoeae
<220> FEATURE:
<221> NAME/KEY: CDS
<222> LOCATION: (1)..(1293)

<400> SEQUENCE: 24 atg agg ata aat atg aac cgt aac gaa att tta ttc gac cgc gcc aag     48
Met Arg Ile Asn Met Asn Arg Asn Glu Ile Leu Phe Asp Arg Ala Lys
1               5                   10                  15 gcc atc atc ccc ggc ggc gtg aat tcg ccc gtg cgc gca ttc ggc agc     96
Ala Ile Ile Pro Gly Gly Val Asn Ser Pro Val Arg Ala Phe Gly Ser
            20                  25                  30 gtc ggc ggc gtg ccg cgc ttc atc aaa aaa gcc gaa ggc gcg tat gtt    144
Val Gly Gly Val Pro Arg Phe Ile Lys Lys Ala Glu Gly Ala Tyr Val
        35                  40                  45 tgg gac gaa aac ggc acg cgc tac acc gat tat gtc ggc tct tgg ggg    192
Trp Asp Glu Asn Gly Thr Arg Tyr Thr Asp Tyr Val Gly Ser Trp Gly
    50                  55                  60 cct gcg att gtc gga cac gcg cat ccc gaa gtc gtc gaa gcc gtg cgc    240
Pro Ala Ile Val Gly His Ala His Pro Glu Val Val Glu Ala Val Arg
65                  70                  75                  80 gaa gct gcg ttg ggc ggt ttg tcg ttc ggc gcg ccc acc gaa ggc gaa    288
Glu Ala Ala Leu Gly Gly Leu Ser Phe Gly Ala Pro Thr Glu Gly Glu
                85                  90                  95 atc gcc att gcc gaa caa att gcc gaa att atg ccg tct gtc gaa cgg    336
Ile Ala Ile Ala Glu Gln Ile Ala Glu Ile Met Pro Ser Val Glu Arg
            100                 105                 110 ctg cgc ctc gtc agc tcc ggc acg gaa gcg acg atg act gcc atc cgt    384
Leu Arg Leu Val Ser Ser Gly Thr Glu Ala Thr Met Thr Ala Ile Arg
        115                 120                 125 ctg gca cgc ggt ttt acc ggc cgc gac aaa atc atc aaa ttt gaa ggc    432
Leu Ala Arg Gly Phe Thr Gly Arg Asp Lys Ile Ile Lys Phe Glu Gly
```

```
                Leu Ala Arg Gly Phe Thr Gly Arg Asp Lys Ile Ile Lys Phe Glu Gly
                    130                 135                 140 tgc tac cac ggc cat tcc gac agc ctg ttg gtg aaa gca ggc agc ggt       480
Cys Tyr His Gly His Ser Asp Ser Leu Leu Val Lys Ala Gly Ser Gly
145                 150                 155                 160 ctg ctt acc ttc ggc aat cct tct tcc gcc ggt gtg cct gcc gac ttt       528
Leu Leu Thr Phe Gly Asn Pro Ser Ser Ala Gly Val Pro Ala Asp Phe
                165                 170                 175 acc aaa cat act ttg gta ctc gaa tac aac aac atc gcc caa ctc gaa       576
Thr Lys His Thr Leu Val Leu Glu Tyr Asn Asn Ile Ala Gln Leu Glu
            180                 185                 190 gaa gcc ttt gcc caa agc ggc gac gaa atc gcc tgc gtg att gtc gaa       624
Glu Ala Phe Ala Gln Ser Gly Asp Glu Ile Ala Cys Val Ile Val Glu
        195                 200                 205 ccc ttc gtc ggc aat atg aac ctc gtc cgc ccg acc gaa gcc ttt gtc       672
Pro Phe Val Gly Asn Met Asn Leu Val Arg Pro Thr Glu Ala Phe Val
    210                 215                 220 aaa gcc ttg cgc gga ttg acc gaa aaa cac ggc gcg gtg ttg att tac       720
Lys Ala Leu Arg Gly Leu Thr Glu Lys His Gly Ala Val Leu Ile Tyr
225                 230                 235                 240 gac gaa gtg atg acc ggt ttc cgc gtc gcg ctc ggc ggc gcg cag tcg       768
Asp Glu Val Met Thr Gly Phe Arg Val Ala Leu Gly Gly Ala Gln Ser
                245                 250                 255 ctg cac ggc atc acg ccc gac ctg acc acg atg ggc aaa gtc atc ggc       816
Leu His Gly Ile Thr Pro Asp Leu Thr Thr Met Gly Lys Val Ile Gly
                260                 265                 270 ggc ggt atg ccg ctt gcc gcg ttc ggc gga cgc aaa gac atc atg gaa       864
Gly Gly Met Pro Leu Ala Ala Phe Gly Gly Arg Lys Asp Ile Met Glu
            275                 280                 285 tgt att tcc ccg ttg ggc ggc gtg tat cag gca ggt aca tta tca ggc       912
Cys Ile Ser Pro Leu Gly Gly Val Tyr Gln Ala Gly Thr Leu Ser Gly
        290                 295                 300 aac ccg att gcc gtc gcc gcc ggc ttg aaa acg ctg gaa atc atc cag       960
Asn Pro Ile Ala Val Ala Ala Gly Leu Lys Thr Leu Glu Ile Ile Gln
305                 310                 315                 320 cgc gaa ggc ttc tat gaa aac ctg acc gcc ttg aca caa cgc ctt gcc      1008
Arg Glu Gly Phe Tyr Glu Asn Leu Thr Ala Leu Thr Gln Arg Leu Ala
                325                 330                 335 aac ggt att gcc gcc gcc aaa gcg cac ggt atc gag ttt gcc gcc gac      1056
Asn Gly Ile Ala Ala Ala Lys Ala His Gly Ile Glu Phe Ala Ala Asp
                340                 345                 350 agc gtg ggc ggt atg ttc ggt ctg tat ttc gcc gca cac gtg ccg cga      1104
Ser Val Gly Gly Met Phe Gly Leu Tyr Phe Ala Ala His Val Pro Arg
            355                 360                 365 aac tat gcc gat atg gcg cgc tcc aat atc gac gct ttc aaa cgc ttc      1152
Asn Tyr Ala Asp Met Ala Arg Ser Asn Ile Asp Ala Phe Lys Arg Phe
        370                 375                 380 ttc cac ggc atg ctc gac cgc ggc att gcc ttc ggc ccg tcc gct tat      1200
Phe His Gly Met Leu Asp Arg Gly Ile Ala Phe Gly Pro Ser Ala Tyr
385                 390                 395                 400 gaa gcg ggt ttc gtt tcc gcc gcg cat acg ccc gag ctg att gac gaa      1248
Glu Ala Gly Phe Val Ser Ala Ala His Thr Pro Glu Leu Ile Asp Glu
                405                 410                 415 acg gtt gcg gtt gcg gtt gaa gtg ttc aag gcg atg gct gca tga          1293
Thr Val Ala Val Ala Val Glu Val Phe Lys Ala Met Ala Ala
                420                 425                 430

<210> SEQ ID NO 25
<211> LENGTH: 430
<212> TYPE: PRT
```

<213> ORGANISM: Neisseria gonorrhoeae

<400> SEQUENCE: 25

Met Arg Ile Asn Met Asn Arg Asn Glu Ile Leu Phe Asp Arg Ala Lys
1               5                   10                  15

Ala Ile Ile Pro Gly Gly Val Asn Ser Pro Val Arg Ala Phe Gly Ser
            20                  25                  30

Val Gly Gly Val Pro Arg Phe Ile Lys Lys Ala Glu Gly Ala Tyr Val
        35                  40                  45

Trp Asp Glu Asn Gly Thr Arg Tyr Thr Asp Tyr Val Gly Ser Trp Gly
50                  55                  60

Pro Ala Ile Val Gly His Ala His Pro Glu Val Val Glu Ala Val Arg
65                  70                  75                  80

Glu Ala Ala Leu Gly Gly Leu Ser Phe Gly Ala Pro Thr Glu Gly Glu
                85                  90                  95

Ile Ala Ile Ala Glu Gln Ile Ala Glu Ile Met Pro Ser Val Glu Arg
            100                 105                 110

Leu Arg Leu Val Ser Ser Gly Thr Glu Ala Thr Met Thr Ala Ile Arg
        115                 120                 125

Leu Ala Arg Gly Phe Thr Gly Arg Asp Lys Ile Ile Lys Phe Glu Gly
130                 135                 140

Cys Tyr His Gly His Ser Asp Ser Leu Leu Val Lys Ala Gly Ser Gly
145                 150                 155                 160

Leu Leu Thr Phe Gly Asn Pro Ser Ser Ala Gly Val Pro Ala Asp Phe
                165                 170                 175

Thr Lys His Thr Leu Val Leu Glu Tyr Asn Asn Ile Ala Gln Leu Glu
            180                 185                 190

Glu Ala Phe Ala Gln Ser Gly Asp Glu Ile Ala Cys Val Ile Val Glu
        195                 200                 205

Pro Phe Val Gly Asn Met Asn Leu Val Arg Pro Thr Glu Ala Phe Val
210                 215                 220

Lys Ala Leu Arg Gly Leu Thr Glu Lys His Gly Ala Val Leu Ile Tyr
225                 230                 235                 240

Asp Glu Val Met Thr Gly Phe Arg Val Ala Leu Gly Gly Ala Gln Ser
                245                 250                 255

Leu His Gly Ile Thr Pro Asp Leu Thr Thr Met Gly Lys Val Ile Gly
            260                 265                 270

Gly Gly Met Pro Leu Ala Ala Phe Gly Gly Arg Lys Asp Ile Met Glu
        275                 280                 285

Cys Ile Ser Pro Leu Gly Gly Val Tyr Gln Ala Gly Thr Leu Ser Gly
290                 295                 300

Asn Pro Ile Ala Val Ala Ala Gly Leu Lys Thr Leu Glu Ile Ile Gln
305                 310                 315                 320

Arg Glu Gly Phe Tyr Glu Asn Leu Thr Ala Leu Thr Gln Arg Leu Ala
                325                 330                 335

Asn Gly Ile Ala Ala Ala Lys Ala His Gly Ile Glu Phe Ala Ala Asp
            340                 345                 350

Ser Val Gly Gly Met Phe Gly Leu Tyr Phe Ala Ala His Val Pro Arg
        355                 360                 365

Asn Tyr Ala Asp Met Ala Arg Ser Asn Ile Asp Ala Phe Lys Arg Phe
370                 375                 380

Phe His Gly Met Leu Asp Arg Gly Ile Ala Phe Gly Pro Ser Ala Tyr
385                 390                 395                 400

```
Glu Ala Gly Phe Val Ser Ala His Thr Pro Glu Leu Ile Asp Glu
                405                 410                 415

Thr Val Ala Val Ala Val Glu Val Phe Lys Ala Met Ala Ala
            420                 425                 430

<210> SEQ ID NO 26
<211> LENGTH: 924
<212> TYPE: DNA
<213> ORGANISM: Pseudomonas aeruginosa
<220> FEATURE:
<221> NAME/KEY: CDS
<222> LOCATION: (1)..(924)

<400> SEQUENCE: 26 atg tcg atg gcc gat cgt gat ggc gtg atc tgg tat gac ggt gaa ctg        48
Met Ser Met Ala Asp Arg Asp Gly Val Ile Trp Tyr Asp Gly Glu Leu
1               5                   10                  15 gtg cag tgg cgc gac gcg acc acg cac gtg ctg acc cat acc ctg cac        96
Val Gln Trp Arg Asp Ala Thr Thr His Val Leu Thr His Thr Leu His
            20                  25                  30 tat gga atg ggc gtg ttc gag ggc gtg cgc gcc tac gac acc ccg cag       144
Tyr Gly Met Gly Val Phe Glu Gly Val Arg Ala Tyr Asp Thr Pro Gln
        35                  40                  45 ggc acg gcg atc ttc cgc ctg cag gcg cat acc gac cgg ctg ttc gac       192
Gly Thr Ala Ile Phe Arg Leu Gln Ala His Thr Asp Arg Leu Phe Asp
    50                  55                  60 tcc gcg cac atc atg aac atg cag atc ccg tac agc cgc gac gag atc       240
Ser Ala His Ile Met Asn Met Gln Ile Pro Tyr Ser Arg Asp Glu Ile
65                  70                  75                  80 aac gag gcg acc cgc gcc gcc gtg cgc gag aac aac ctg gaa agc gcc       288
Asn Glu Ala Thr Arg Ala Ala Val Arg Glu Asn Asn Leu Glu Ser Ala
                85                  90                  95 tat atc cgc ccg atg gtg ttc tac gga agc gaa ggc atg ggc ctg cgc       336
Tyr Ile Arg Pro Met Val Phe Tyr Gly Ser Glu Gly Met Gly Leu Arg
            100                 105                 110 gcc agc ggc ctg aag gtc cat gtg atc atc gcc gcc tgg agc tgg ggc       384
Ala Ser Gly Leu Lys Val His Val Ile Ile Ala Ala Trp Ser Trp Gly
        115                 120                 125 gcc tac atg ggc gag gaa gcc ctg cag caa ggc atc aag gtg cgc acc       432
Ala Tyr Met Gly Glu Glu Ala Leu Gln Gln Gly Ile Lys Val Arg Thr
    130                 135                 140 agt tcc ttc acc cgc cac cac gtc aac atc tcg atg acc cgc gcc aag       480
Ser Ser Phe Thr Arg His His Val Asn Ile Ser Met Thr Arg Ala Lys
145                 150                 155                 160 tcc aac ggc gcc tac atc aac tcg atg ctg gcc ctc cag gaa gcg atc       528
Ser Asn Gly Ala Tyr Ile Asn Ser Met Leu Ala Leu Gln Glu Ala Ile
                165                 170                 175 tcc ggc ggc gcc gac gag gcc atg atg ctc gat ccg gaa ggc tac gtg       576
Ser Gly Gly Ala Asp Glu Ala Met Met Leu Asp Pro Glu Gly Tyr Val
            180                 185                 190 gcc gaa ggc tcc ggc gag aac atc ttc atc atc aag gat ggc gtg atc       624
Ala Glu Gly Ser Gly Glu Asn Ile Phe Ile Ile Lys Asp Gly Val Ile
        195                 200                 205 tac acc ccg gaa gtc acc gcc tgc ctg aac ggc atc act cgt aac act       672
Tyr Thr Pro Glu Val Thr Ala Cys Leu Asn Gly Ile Thr Arg Asn Thr
    210                 215                 220 atc ctg acc ctg gcc gcc gaa cac ggt ttt aaa ctg gtc gag aag cgc       720
Ile Leu Thr Leu Ala Ala Glu His Gly Phe Lys Leu Val Glu Lys Arg
225                 230                 235                 240 atc acc cgc gac gag gtg tac atc gcc gac gag gcc ttc ttc act ggc       768
Ile Thr Arg Asp Glu Val Tyr Ile Ala Asp Glu Ala Phe Phe Thr Gly
```

245                 250                 255
act gcc gcg gaa gtc acg ccg atc cgc gaa gtg gac ggt cgc aag atc         816
Thr Ala Ala Glu Val Thr Pro Ile Arg Glu Val Asp Gly Arg Lys Ile
            260                 265                 270 ggc gcc ggc cgc cgt ggc ccg gtc acc gaa aag ctg cag aaa gcc tat         864
Gly Ala Gly Arg Arg Gly Pro Val Thr Glu Lys Leu Gln Lys Ala Tyr
        275                 280                 285 ttc gac ctg gtc agc ggc aag acc gag gcc cac gcc gag tgg cgt acc         912
Phe Asp Leu Val Ser Gly Lys Thr Glu Ala His Ala Glu Trp Arg Thr
290                 295                 300 ctg gtc aag taa                                                          924
Leu Val Lys
305

<210> SEQ ID NO 27
<211> LENGTH: 307
<212> TYPE: PRT
<213> ORGANISM: Pseudomonas aeruginosa

<400> SEQUENCE: 27

Met Ser Met Ala Asp Arg Asp Gly Val Ile Trp Tyr Asp Gly Glu Leu
1               5                   10                  15

Val Gln Trp Arg Asp Ala Thr Thr His Val Leu Thr His Thr Leu His
            20                  25                  30

Tyr Gly Met Gly Val Phe Glu Gly Val Arg Ala Tyr Asp Thr Pro Gln
        35                  40                  45

Gly Thr Ala Ile Phe Arg Leu Gln Ala His Thr Asp Arg Leu Phe Asp
    50                  55                  60

Ser Ala His Ile Met Asn Met Gln Ile Pro Tyr Ser Arg Asp Glu Ile
65                  70                  75                  80

Asn Glu Ala Thr Arg Ala Ala Val Arg Glu Asn Asn Leu Glu Ser Ala
                85                  90                  95

Tyr Ile Arg Pro Met Val Phe Tyr Gly Ser Glu Gly Met Gly Leu Arg
            100                 105                 110

Ala Ser Gly Leu Lys Val His Val Ile Ala Ala Trp Ser Trp Gly
        115                 120                 125

Ala Tyr Met Gly Glu Glu Ala Leu Gln Gln Gly Ile Lys Val Arg Thr
    130                 135                 140

Ser Ser Phe Thr Arg His His Val Asn Ile Ser Met Thr Arg Ala Lys
145                 150                 155                 160

Ser Asn Gly Ala Tyr Ile Asn Ser Met Leu Ala Leu Gln Glu Ala Ile
                165                 170                 175

Ser Gly Gly Ala Asp Glu Ala Met Met Leu Asp Pro Glu Gly Tyr Val
            180                 185                 190

Ala Glu Gly Ser Gly Glu Asn Ile Phe Ile Ile Lys Asp Gly Val Ile
        195                 200                 205

Tyr Thr Pro Glu Val Thr Ala Cys Leu Asn Gly Ile Thr Arg Asn Thr
    210                 215                 220

Ile Leu Thr Leu Ala Ala Glu His Gly Phe Lys Leu Val Glu Lys Arg
225                 230                 235                 240

Ile Thr Arg Asp Glu Val Tyr Ile Ala Asp Glu Ala Phe Phe Thr Gly
                245                 250                 255

Thr Ala Ala Glu Val Thr Pro Ile Arg Glu Val Asp Gly Arg Lys Ile
            260                 265                 270

Gly Ala Gly Arg Arg Gly Pro Val Thr Glu Lys Leu Gln Lys Ala Tyr
        275                 280                 285

```
Phe Asp Leu Val Ser Gly Lys Thr Glu Ala His Ala Glu Trp Arg Thr
    290                 295                 300

Leu Val Lys
305

<210> SEQ ID NO 28
<211> LENGTH: 1407
<212> TYPE: DNA
<213> ORGANISM: Rhodopseudomonas palustris
<220> FEATURE:
<221> NAME/KEY: CDS
<222> LOCATION: (1)..(1407)

<400> SEQUENCE: 28 atg aag ctg ata ccg tgc cgc gcc ttt cac ccc ccg gcc gcg cag tgc     48
Met Lys Leu Ile Pro Cys Arg Ala Phe His Pro Pro Ala Ala Gln Cys
1               5                   10                  15 atg agg agc gcc atg tta gac aag atc aag ccc acg tcc gcc gtc aac     96
Met Arg Ser Ala Met Leu Asp Lys Ile Lys Pro Thr Ser Ala Val Asn
                20                  25                  30 gcg ccg aac gat ctc aac gcg ttc tgg atg ccg ttc acc gcg aac cgg    144
Ala Pro Asn Asp Leu Asn Ala Phe Trp Met Pro Phe Thr Ala Asn Arg
            35                  40                  45 gcc ttc aag cgc gcg ccg aag atg gtc gtg ggt gcc gaa ggc atg cac    192
Ala Phe Lys Arg Ala Pro Lys Met Val Val Gly Ala Glu Gly Met His
        50                  55                  60 tac atc acc gcc gat ggt cgc aag atc atc gac gcc gcc tcg ggc atg    240
Tyr Ile Thr Ala Asp Gly Arg Lys Ile Ile Asp Ala Ala Ser Gly Met
65                  70                  75                  80 tgg tgc acc aat gcg ggc cat ggc cgc aag gaa atc gcc gag gcg atc    288
Trp Cys Thr Asn Ala Gly His Gly Arg Lys Glu Ile Ala Glu Ala Ile
                85                  90                  95 aag gcg cag gcc gat gaa ctc gac ttc tcg ccg ccg ttc cag ttc ggc    336
Lys Ala Gln Ala Asp Glu Leu Asp Phe Ser Pro Pro Phe Gln Phe Gly
                100                 105                 110 cag ccg aag gcg ttc gaa ctc gcc agc cgg atc gcc gat ctg gcg ccg    384
Gln Pro Lys Ala Phe Glu Leu Ala Ser Arg Ile Ala Asp Leu Ala Pro
        115                 120                 125 gaa ggc ctc gat cac gtg ttc ttc tgc aat tcg ggc tcg gaa gcc ggc    432
Glu Gly Leu Asp His Val Phe Phe Cys Asn Ser Gly Ser Glu Ala Gly
        130                 135                 140 gac acc gcg ctg aag atc gcg gtc gcc tat cag cag atc aag ggc cag    480
Asp Thr Ala Leu Lys Ile Ala Val Ala Tyr Gln Gln Ile Lys Gly Gln
145                 150                 155                 160 ggc tca cgc acc cgc ctg atc ggc cgc gag cgc ggc tat cac ggc gtc    528
Gly Ser Arg Thr Arg Leu Ile Gly Arg Glu Arg Gly Tyr His Gly Val
                165                 170                 175 ggc ttc ggc ggc acc gcg gtc ggc ggc atc ggc aac aac cgc aag atg    576
Gly Phe Gly Gly Thr Ala Val Gly Gly Ile Gly Asn Asn Arg Lys Met
                180                 185                 190 ttc ggt ccg ctg ctc aac ggc gtc gat cat ctg cct gcg act tat gat    624
Phe Gly Pro Leu Leu Asn Gly Val Asp His Leu Pro Ala Thr Tyr Asp
        195                 200                 205 cgc gac aag cag gct ttc acc atc ggc gag ccg gaa tac ggc gcg cac    672
Arg Asp Lys Gln Ala Phe Thr Ile Gly Glu Pro Glu Tyr Gly Ala His
        210                 215                 220 ttc gcc gaa gcg ctt gaa ggc ctc gtc aat ctg cac ggc gcc aac acc    720
Phe Ala Glu Ala Leu Glu Gly Leu Val Asn Leu His Gly Ala Asn Thr
225                 230                 235                 240 atc gcg gcg gtg atc gtc gag ccg atg gcc ggc tcc acc ggc gtg ctg    768
```

```
Ile Ala Ala Val Ile Val Glu Pro Met Ala Gly Ser Thr Gly Val Leu
                245                 250                 255 ccg gcg ccg aag ggc tat ctc aag aag ctg cgc gag atc acc aag aag         816
Pro Ala Pro Lys Gly Tyr Leu Lys Lys Leu Arg Glu Ile Thr Lys Lys
            260                 265                 270 cac ggc atc ctg ctg atc ttc gac gag gtc atc acc ggc tac ggc cgt         864
His Gly Ile Leu Leu Ile Phe Asp Glu Val Ile Thr Gly Tyr Gly Arg
                275                 280                 285 ctc ggc tat gcc ttc gcg tcc gaa cgt tac ggc gtc acc ccg gac atg         912
Leu Gly Tyr Ala Phe Ala Ser Glu Arg Tyr Gly Val Thr Pro Asp Met
            290                 295                 300 atc acc ttc gcc aag ggc gtc acc aat ggt gcg gtg ccg atg ggc ggc         960
Ile Thr Phe Ala Lys Gly Val Thr Asn Gly Ala Val Pro Met Gly Gly
305                 310                 315                 320 gtg atc acc tcg gcg gag atc cac gat gcg ttc atg acc ggc ccc gag        1008
Val Ile Thr Ser Ala Glu Ile His Asp Ala Phe Met Thr Gly Pro Glu
                325                 330                 335 cac gcg gtc gag ctg gcg cac ggc tac acc tat tcg gcg cat ccg ctc        1056
His Ala Val Glu Leu Ala His Gly Tyr Thr Tyr Ser Ala His Pro Leu
            340                 345                 350 gcc tgc gcg gcc ggc atc gcc acc ctc gac atc tac cgc gac gag aag        1104
Ala Cys Ala Ala Gly Ile Ala Thr Leu Asp Ile Tyr Arg Asp Glu Lys
                355                 360                 365 ctg ttc gag cgc gcc aag gcg ctg gag ccg aag ttt gcc gag gcg gtg        1152
Leu Phe Glu Arg Ala Lys Ala Leu Glu Pro Lys Phe Ala Glu Ala Val
370                 375                 380 atg tcg ctg aag tcg gcc ccg aac gtg gtc gac atc cgc acc gtc ggc        1200
Met Ser Leu Lys Ser Ala Pro Asn Val Val Asp Ile Arg Thr Val Gly
385                 390                 395                 400 ctg acg gcg ggt atc gac ctc gct tcg atc gcc gat gcg gtc ggc aag        1248
Leu Thr Ala Gly Ile Asp Leu Ala Ser Ile Ala Asp Ala Val Gly Lys
                405                 410                 415 cgt ggc ttc gaa gcg atg aat gcc ggc ttc cac gac cac gag ctg atg        1296
Arg Gly Phe Glu Ala Met Asn Ala Gly Phe His Asp His Glu Leu Met
            420                 425                 430 ctg cgg atc gcc ggc gac acc ctg gcg ctg acc ccg ccg ctg atc ctc        1344
Leu Arg Ile Ala Gly Asp Thr Leu Ala Leu Thr Pro Pro Leu Ile Leu
435                 440                 445 agc gag gac cac atc ggt gag atc gtc gac aag gtc ggc aag gtg atc        1392
Ser Glu Asp His Ile Gly Glu Ile Val Asp Lys Val Gly Lys Val Ile
450                 455                 460 cgc gcg gtc gcc tga                                                    1407
Arg Ala Val Ala
465

<210> SEQ ID NO 29
<211> LENGTH: 468
<212> TYPE: PRT
<213> ORGANISM: Rhodopseudomonas palustris

<400> SEQUENCE: 29

Met Lys Leu Ile Pro Cys Arg Ala Phe His Pro Ala Ala Gln Cys
1               5                   10                  15

Met Arg Ser Ala Met Leu Asp Lys Ile Lys Pro Thr Ser Ala Val Asn
            20                  25                  30

Ala Pro Asn Asp Leu Asn Ala Phe Trp Met Pro Phe Thr Ala Asn Arg
        35                  40                  45

Ala Phe Lys Arg Ala Pro Lys Met Val Val Gly Ala Glu Gly Met His
    50                  55                  60
```

```
Tyr Ile Thr Ala Asp Gly Arg Lys Ile Ile Asp Ala Ala Ser Gly Met
 65                  70                  75                  80

Trp Cys Thr Asn Ala Gly His Gly Arg Lys Glu Ile Ala Glu Ala Ile
                 85                  90                  95

Lys Ala Gln Ala Asp Glu Leu Asp Phe Ser Pro Pro Phe Gln Phe Gly
            100                 105                 110

Gln Pro Lys Ala Phe Glu Leu Ala Ser Arg Ile Ala Asp Leu Ala Pro
        115                 120                 125

Glu Gly Leu Asp His Val Phe Phe Cys Asn Ser Gly Ser Glu Ala Gly
    130                 135                 140

Asp Thr Ala Leu Lys Ile Ala Val Ala Tyr Gln Gln Ile Lys Gly Gln
145                 150                 155                 160

Gly Ser Arg Thr Arg Leu Ile Gly Arg Glu Arg Gly Tyr His Gly Val
                165                 170                 175

Gly Phe Gly Gly Thr Ala Val Gly Gly Ile Gly Asn Asn Arg Lys Met
            180                 185                 190

Phe Gly Pro Leu Leu Asn Gly Val Asp His Leu Pro Ala Thr Tyr Asp
        195                 200                 205

Arg Asp Lys Gln Ala Phe Thr Ile Gly Glu Pro Glu Tyr Gly Ala His
    210                 215                 220

Phe Ala Glu Ala Leu Glu Gly Leu Val Asn Leu His Gly Ala Asn Thr
225                 230                 235                 240

Ile Ala Ala Val Ile Val Glu Pro Met Ala Gly Ser Thr Gly Val Leu
                245                 250                 255

Pro Ala Pro Lys Gly Tyr Leu Lys Lys Leu Arg Glu Ile Thr Lys Lys
            260                 265                 270

His Gly Ile Leu Leu Ile Phe Asp Glu Val Ile Thr Gly Tyr Gly Arg
        275                 280                 285

Leu Gly Tyr Ala Phe Ala Ser Glu Arg Tyr Gly Val Thr Pro Asp Met
    290                 295                 300

Ile Thr Phe Ala Lys Gly Val Thr Asn Gly Ala Val Pro Met Gly Gly
305                 310                 315                 320

Val Ile Thr Ser Ala Glu Ile His Asp Ala Phe Met Thr Gly Pro Glu
                325                 330                 335

His Ala Val Glu Leu Ala His Gly Tyr Thr Tyr Ser Ala His Pro Leu
            340                 345                 350

Ala Cys Ala Ala Gly Ile Ala Thr Leu Asp Ile Tyr Arg Asp Glu Lys
        355                 360                 365

Leu Phe Glu Arg Ala Lys Ala Leu Glu Pro Lys Phe Ala Glu Ala Val
    370                 375                 380

Met Ser Leu Lys Ser Ala Pro Asn Val Val Asp Ile Arg Thr Val Gly
385                 390                 395                 400

Leu Thr Ala Gly Ile Asp Leu Ala Ser Ile Ala Asp Ala Val Gly Lys
                405                 410                 415

Arg Gly Phe Glu Ala Met Asn Ala Gly Phe His Asp Glu Leu Met
            420                 425                 430

Leu Arg Ile Ala Gly Asp Thr Leu Ala Leu Thr Pro Pro Leu Ile Leu
        435                 440                 445

Ser Glu Asp His Ile Gly Glu Ile Val Asp Lys Val Gly Lys Val Ile
    450                 455                 460

Arg Ala Val Ala
465
```

```
<210> SEQ ID NO 30
<211> LENGTH: 1263
<212> TYPE: DNA
<213> ORGANISM: Escherichia coli
<220> FEATURE:
<221> NAME/KEY: CDS
<222> LOCATION: (1)..(1263)

<400> SEQUENCE: 30
```

| | | | | | | | | | | | | | | | | |
|---|---|---|---|---|---|---|---|---|---|---|---|---|---|---|---|---|
| atg | cca | cat | tca | ctg | ttc | agc | acc | gat | acc | gat | ctc | acc | gcc | gaa | aat | 48 |
| Met | Pro | His | Ser | Leu | Phe | Ser | Thr | Asp | Thr | Asp | Leu | Thr | Ala | Glu | Asn | |
| 1 | | | | 5 | | | | | 10 | | | | | 15 | | |
| ctg | ctg | cgt | ttg | ccc | gct | gaa | ttt | ggc | tgc | ccg | gtg | tgg | gtc | tac | gat | 96 |
| Leu | Leu | Arg | Leu | Pro | Ala | Glu | Phe | Gly | Cys | Pro | Val | Trp | Val | Tyr | Asp | |
| | | | 20 | | | | | 25 | | | | | 30 | | | |
| gcg | caa | att | att | cgt | cgg | cag | att | gca | gcg | ctg | aaa | cag | ttt | gat | gtg | 144 |
| Ala | Gln | Ile | Ile | Arg | Arg | Gln | Ile | Ala | Ala | Leu | Lys | Gln | Phe | Asp | Val | |
| | | 35 | | | | | 40 | | | | | 45 | | | | |
| gtg | cgc | ttt | gca | cag | aaa | gcc | tgt | tcc | aat | att | cat | att | ttg | cgc | tta | 192 |
| Val | Arg | Phe | Ala | Gln | Lys | Ala | Cys | Ser | Asn | Ile | His | Ile | Leu | Arg | Leu | |
| 50 | | | | | 55 | | | | | 60 | | | | | | |
| atg | cgt | gag | cag | ggc | gtg | aaa | gtg | gat | tcc | gtc | tcg | tta | ggc | gaa | ata | 240 |
| Met | Arg | Glu | Gln | Gly | Val | Lys | Val | Asp | Ser | Val | Ser | Leu | Gly | Glu | Ile | |
| 65 | | | | | 70 | | | | | 75 | | | | | 80 | |
| gag | cgt | gcg | ttg | gcg | gcg | ggt | tac | aat | ccg | caa | acg | cac | ccc | gat | gat | 288 |
| Glu | Arg | Ala | Leu | Ala | Ala | Gly | Tyr | Asn | Pro | Gln | Thr | His | Pro | Asp | Asp | |
| | | | | 85 | | | | | 90 | | | | | 95 | | |
| att | gtt | ttt | acg | gca | gat | gtt | atc | gat | cag | gcg | acg | ctt | gaa | cgc | gtc | 336 |
| Ile | Val | Phe | Thr | Ala | Asp | Val | Ile | Asp | Gln | Ala | Thr | Leu | Glu | Arg | Val | |
| | | | 100 | | | | | 105 | | | | | 110 | | | |
| agt | gaa | ttg | caa | att | ccg | gtg | aat | gcg | ggt | tct | gtt | gat | atg | ctc | gac | 384 |
| Ser | Glu | Leu | Gln | Ile | Pro | Val | Asn | Ala | Gly | Ser | Val | Asp | Met | Leu | Asp | |
| | | 115 | | | | | 120 | | | | | 125 | | | | |
| caa | ctg | ggc | cag | gtt | tcg | cca | ggg | cat | cgg | gta | tgg | ctg | cgc | gtt | aat | 432 |
| Gln | Leu | Gly | Gln | Val | Ser | Pro | Gly | His | Arg | Val | Trp | Leu | Arg | Val | Asn | |
| 130 | | | | | 135 | | | | | 140 | | | | | | |
| ccg | ggg | ttt | ggt | cac | gga | cat | agc | caa | aaa | acc | aat | acc | ggt | ggc | gaa | 480 |
| Pro | Gly | Phe | Gly | His | Gly | His | Ser | Gln | Lys | Thr | Asn | Thr | Gly | Gly | Glu | |
| 145 | | | | | 150 | | | | | 155 | | | | | 160 | |
| aac | agc | aag | cac | ggt | atc | tgg | tac | acc | gat | ctg | ccc | gcc | gca | ctg | gac | 528 |
| Asn | Ser | Lys | His | Gly | Ile | Trp | Tyr | Thr | Asp | Leu | Pro | Ala | Ala | Leu | Asp | |
| | | | | 165 | | | | | 170 | | | | | 175 | | |
| gtg | ata | caa | cgt | cat | cat | ctg | cag | ctg | gtc | ggc | att | cac | atg | cac | att | 576 |
| Val | Ile | Gln | Arg | His | His | Leu | Gln | Leu | Val | Gly | Ile | His | Met | His | Ile | |
| | | | 180 | | | | | 185 | | | | | 190 | | | |
| ggt | tct | ggc | gtt | gat | tat | gcc | cat | ctg | gaa | cag | gtg | tgt | ggt | gct | atg | 624 |
| Gly | Ser | Gly | Val | Asp | Tyr | Ala | His | Leu | Glu | Gln | Val | Cys | Gly | Ala | Met | |
| | | 195 | | | | | 200 | | | | | 205 | | | | |
| gtg | cgt | cag | gtc | atc | gaa | ttc | ggt | cag | gat | tta | cag | gct | att | tct | gcg | 672 |
| Val | Arg | Gln | Val | Ile | Glu | Phe | Gly | Gln | Asp | Leu | Gln | Ala | Ile | Ser | Ala | |
| | | 210 | | | | | 215 | | | | | 220 | | | | |
| ggc | ggt | ggg | ctt | tct | gtt | cct | tat | caa | cag | ggt | gaa | gag | gcg | gtt | gat | 720 |
| Gly | Gly | Gly | Leu | Ser | Val | Pro | Tyr | Gln | Gln | Gly | Glu | Glu | Ala | Val | Asp | |
| 225 | | | | | 230 | | | | | 235 | | | | | 240 | |
| acc | gaa | cat | tat | tat | ggt | ctg | tgg | aat | gcc | gcg | cgt | gag | caa | atc | gcc | 768 |
| Thr | Glu | His | Tyr | Tyr | Gly | Leu | Trp | Asn | Ala | Ala | Arg | Glu | Gln | Ile | Ala | |
| | | | | 245 | | | | | 250 | | | | | 255 | | |
| cgc | cat | ttg | ggc | cac | cct | gtg | aaa | ctg | gaa | att | gaa | ccg | ggt | cgc | ttc | 816 |
| Arg | His | Leu | Gly | His | Pro | Val | Lys | Leu | Glu | Ile | Glu | Pro | Gly | Arg | Phe | |
| | | | 260 | | | | | 265 | | | | | 270 | | | |
| ctg | gta | gcg | cag | tct | ggc | gta | tta | att | act | cag | gtg | cgg | agc | gtc | aaa | 864 |

```
Leu Val Ala Gln Ser Gly Val Leu Ile Thr Gln Val Arg Ser Val Lys
            275                 280                 285 caa atg ggg agc cgc cac ttt gtg ctg gtt gat gcc ggg ttc aac gat      912
Gln Met Gly Ser Arg His Phe Val Leu Val Asp Ala Gly Phe Asn Asp
        290                 295                 300 ctg atg cgc ccg gca atg tac ggt agt tac cac cat atc agt gcc ctg      960
Leu Met Arg Pro Ala Met Tyr Gly Ser Tyr His His Ile Ser Ala Leu
305                 310                 315                 320 gca gct gat ggt cgt tct ctg gaa cac gcg cca acg gtg gaa acc gtc     1008
Ala Ala Asp Gly Arg Ser Leu Glu His Ala Pro Thr Val Glu Thr Val
                325                 330                 335 gtc gcc gga ccg tta tgt gaa tcg ggc gat gtc ttt acc cag cag gaa     1056
Val Ala Gly Pro Leu Cys Glu Ser Gly Asp Val Phe Thr Gln Gln Glu
            340                 345                 350 ggg gga aat gtt gaa acc cgc gcc ttg ccg gaa gtg aag gca ggt gat     1104
Gly Gly Asn Val Glu Thr Arg Ala Leu Pro Glu Val Lys Ala Gly Asp
        355                 360                 365 tat ctg gta ctg cat gat aca ggg gca tat ggc gca tca atg tca tcc     1152
Tyr Leu Val Leu His Asp Thr Gly Ala Tyr Gly Ala Ser Met Ser Ser
370                 375                 380 aac tac aat agc cgt ccg ctg tta cca gaa gtt ctg ttt gat aat ggt     1200
Asn Tyr Asn Ser Arg Pro Leu Leu Pro Glu Val Leu Phe Asp Asn Gly
385                 390                 395                 400 cag gcg cgg ttg att cgc cgt cgc cag acc atc gaa gaa tta ctg gcg     1248
Gln Ala Arg Leu Ile Arg Arg Arg Gln Thr Ile Glu Glu Leu Leu Ala
                405                 410                 415 ctg gaa ttg ctt taa                                                  1263
Leu Glu Leu Leu
            420

<210> SEQ ID NO 31
<211> LENGTH: 420
<212> TYPE: PRT
<213> ORGANISM: Escherichia coli

<400> SEQUENCE: 31

Met Pro His Ser Leu Phe Ser Thr Asp Thr Asp Leu Thr Ala Glu Asn
1               5                   10                  15

Leu Leu Arg Leu Pro Ala Glu Phe Gly Cys Pro Val Trp Val Tyr Asp
            20                  25                  30

Ala Gln Ile Ile Arg Arg Gln Ile Ala Ala Leu Lys Gln Phe Asp Val
        35                  40                  45

Val Arg Phe Ala Gln Lys Ala Cys Ser Asn Ile His Ile Leu Arg Leu
    50                  55                  60

Met Arg Glu Gln Gly Val Lys Val Asp Ser Val Ser Leu Gly Glu Ile
65                  70                  75                  80

Glu Arg Ala Leu Ala Ala Gly Tyr Asn Pro Gln Thr His Pro Asp Asp
                85                  90                  95

Ile Val Phe Thr Ala Asp Val Ile Asp Gln Ala Thr Leu Glu Arg Val
            100                 105                 110

Ser Glu Leu Gln Ile Pro Val Asn Ala Gly Ser Val Asp Met Leu Asp
        115                 120                 125

Gln Leu Gly Gln Val Ser Pro Gly His Arg Val Trp Leu Arg Val Asn
    130                 135                 140

Pro Gly Phe Gly His Gly His Ser Gln Lys Thr Asn Thr Gly Gly Glu
145                 150                 155                 160

Asn Ser Lys His Gly Ile Trp Tyr Thr Asp Leu Pro Ala Ala Leu Asp
                165                 170                 175
```

```
Val Ile Gln Arg His His Leu Gln Leu Val Gly Ile His Met His Ile
                180                 185                 190

Gly Ser Gly Val Asp Tyr Ala His Leu Glu Gln Val Cys Gly Ala Met
            195                 200                 205

Val Arg Gln Val Ile Glu Phe Gly Gln Asp Leu Gln Ala Ile Ser Ala
210                 215                 220

Gly Gly Gly Leu Ser Val Pro Tyr Gln Gln Gly Glu Glu Ala Val Asp
225                 230                 235                 240

Thr Glu His Tyr Tyr Gly Leu Trp Asn Ala Ala Arg Glu Gln Ile Ala
                245                 250                 255

Arg His Leu Gly His Pro Val Lys Leu Glu Ile Glu Pro Gly Arg Phe
            260                 265                 270

Leu Val Ala Gln Ser Gly Val Leu Ile Thr Gln Val Arg Ser Val Lys
        275                 280                 285

Gln Met Gly Ser Arg His Phe Val Leu Val Asp Ala Gly Phe Asn Asp
    290                 295                 300

Leu Met Arg Pro Ala Met Tyr Gly Ser Tyr His His Ile Ser Ala Leu
305                 310                 315                 320

Ala Ala Asp Gly Arg Ser Leu Glu His Ala Pro Thr Val Glu Thr Val
                325                 330                 335

Val Ala Gly Pro Leu Cys Glu Ser Gly Asp Val Phe Thr Gln Gln Glu
            340                 345                 350

Gly Gly Asn Val Glu Thr Arg Ala Leu Pro Glu Val Lys Ala Gly Asp
        355                 360                 365

Tyr Leu Val Leu His Asp Thr Gly Ala Tyr Gly Ala Ser Met Ser Ser
    370                 375                 380

Asn Tyr Asn Ser Arg Pro Leu Leu Pro Glu Val Leu Phe Asp Asn Gly
385                 390                 395                 400

Gln Ala Arg Leu Ile Arg Arg Gln Thr Ile Glu Glu Leu Leu Ala
                405                 410                 415

Leu Glu Leu Leu
            420

<210> SEQ ID NO 32
<211> LENGTH: 1265
<212> TYPE: DNA
<213> ORGANISM: Artificial
<220> FEATURE:
<223> OTHER INFORMATION: Escherichia.coli diaminopimelate decarboxylase
      LysA codon optimised gene

<400> SEQUENCE: 32
atatgccaca ctctctgttt tctactgata ctgatctgac tgcggaaaac ctgctgcgtc      60
tgccggctga attcggttgt ccggtatggg tgtacgacgc tcagattatt cgtcgccaga     120
tcgcagcact gaagcagttc gatgtagtgc gttttgcaca gaaggcgtgc tccaacatcc     180
atatcctgcg cctgatgcgt gagcagggcg ttaaagttga ctccgtctct ctgggtgaga     240
ttgagcgcgc cctggcagcc ggctataacc cacagaccca tcctgacgac attgtattta     300
ctgccgacgt gatcgaccag gctactctgg aacgcgtttc tgaactgcag atcccggtta     360
atgctggttc tgtggacatg ctggaccagc tgggccaggt atccccaggt catcgtgtgt     420
ggctgcgtgt caacccaggt ttcggccacg ccactctca gaaaactaac actggtggtg     480
agaactccaa gcatggcatt tggtataccg atctgccggc tgcactggac gtaatccagc     540
gtcaccacct gcagctggtg ggcatccaca tgcacattgg ctccggcgta gactacgccc     600
```

-continued

```
acctggagca agtctgcggt gctatggtac gtcaggtaat cgagttcggc caagatctgc    660
aggcaatcag cgctggtggc ggcctgtctg taccttatca gcagggcgag gaggcggttg    720
acactgagca ctactacggt ctgtggaacg ccgctcgtga gcaaattgca cgtcacctgg    780
gccacccggt gaaactggag atcgagccgg ccgcttcct ggtagcacag tccggcgtac    840
tgattaccca ggtacgctct gttaaacaga tgggctcccg tcactttgtg ctggtagacg    900
caggcttcaa cgacctgatg cgtccggcta tgtatggttc ctatcatcac atctctgcgc    960
tggccgccga cggccgctct ctggaacacg cgccgacggt tgaaacggtg gtggctggtc   1020
cgctgtgcga gtccggcgac gttttcactc agcaggaggg cggcaatgta gagacgcgtg   1080
cgctgccgga agtgaaagcc ggtgattatc tggtgctgca tgataccggc gcctatggtg   1140
cgagcatgag cagcaactac aactctcgcc cgctgctgcc ggaggtcctg ttcgataacg   1200
gccaagcccg cctgatccgt cgtcgtcaga ccatcgagga actgctggca ctggagctgc   1260
tgtaa                                                                1265
```

<210> SEQ ID NO 33
<211> LENGTH: 1692
<212> TYPE: DNA
<213> ORGANISM: Saccharomyces cerevisiae
<220> FEATURE:
<221> NAME/KEY: CDS
<222> LOCATION: (1)..(1692)

<400> SEQUENCE: 33

```
atg tct gaa att act ttg ggt aaa tat ttg ttc gaa aga tta aag caa      48
Met Ser Glu Ile Thr Leu Gly Lys Tyr Leu Phe Glu Arg Leu Lys Gln
1               5                   10                  15 gtc aac gtt aac acc gtt ttc ggt ttg cca ggt gac ttc aac ttg tcc      96
Val Asn Val Asn Thr Val Phe Gly Leu Pro Gly Asp Phe Asn Leu Ser
            20                  25                  30 ttg ttg gac aag atc tac gaa gtt gaa ggt atg aga tgg gct ggt aac     144
Leu Leu Asp Lys Ile Tyr Glu Val Glu Gly Met Arg Trp Ala Gly Asn
        35                  40                  45 gcc aac gaa ttg aac gct gct tac gcc gct gat ggt tac gct cgt atc     192
Ala Asn Glu Leu Asn Ala Ala Tyr Ala Ala Asp Gly Tyr Ala Arg Ile
    50                  55                  60 aag ggt atg tct tgt atc atc acc acc ttc ggt gtc ggt gaa ttg tct     240
Lys Gly Met Ser Cys Ile Ile Thr Thr Phe Gly Val Gly Glu Leu Ser
65                  70                  75                  80 gct ttg aac ggt att gcc ggt tct tac gct gaa cac gtc ggt gtt ttg     288
Ala Leu Asn Gly Ile Ala Gly Ser Tyr Ala Glu His Val Gly Val Leu
                85                  90                  95 cac gtt gtt ggt gtc cca tcc atc tct gct caa gct aag caa ttg ttg     336
His Val Val Gly Val Pro Ser Ile Ser Ala Gln Ala Lys Gln Leu Leu
            100                 105                 110 ttg cac cac acc ttg ggt aac ggt gac ttc act gtt ttc cac aga atg     384
Leu His His Thr Leu Gly Asn Gly Asp Phe Thr Val Phe His Arg Met
        115                 120                 125 tct gcc aac att tct gaa acc act gct atg atc act gac att gct acc     432
Ser Ala Asn Ile Ser Glu Thr Thr Ala Met Ile Thr Asp Ile Ala Thr
    130                 135                 140 gcc cca gct gaa att gac aga tgt atc aga acc act tac gtc acc caa     480
Ala Pro Ala Glu Ile Asp Arg Cys Ile Arg Thr Thr Tyr Val Thr Gln
145                 150                 155                 160 aga cca gtc tac tta ggt ttg cca gct aac ttg gtc gac ttg aac gtc     528
Arg Pro Val Tyr Leu Gly Leu Pro Ala Asn Leu Val Asp Leu Asn Val
                165                 170                 175
```

```
cca gct aag ttg ttg caa act cca att gac atg tct ttg aag cca aac      576
Pro Ala Lys Leu Leu Gln Thr Pro Ile Asp Met Ser Leu Lys Pro Asn
            180                 185                 190 gat gct gaa tcc gaa aag gaa gtc att gac acc atc ttg gct ttg gtc      624
Asp Ala Glu Ser Glu Lys Glu Val Ile Asp Thr Ile Leu Ala Leu Val
        195                 200                 205 aag gat gct aag aac cca gtt atc ttg gct gat gct tgt tgt tcc aga      672
Lys Asp Ala Lys Asn Pro Val Ile Leu Ala Asp Ala Cys Cys Ser Arg
    210                 215                 220 cac gac gtc aag gct gaa act aag aag ttg att gac ttg act caa ttc      720
His Asp Val Lys Ala Glu Thr Lys Lys Leu Ile Asp Leu Thr Gln Phe
225                 230                 235                 240 cca gct ttc gtc acc cca atg ggt aag ggt tcc att gac gaa caa cac      768
Pro Ala Phe Val Thr Pro Met Gly Lys Gly Ser Ile Asp Glu Gln His
                245                 250                 255 cca aga tac ggt ggt gtt tac gtc ggt acc ttg tcc aag cca gaa gtt      816
Pro Arg Tyr Gly Gly Val Tyr Val Gly Thr Leu Ser Lys Pro Glu Val
            260                 265                 270 aag gaa gcc gtt gaa tct gct gac ttg att ttg tct gtc ggt gct ttg      864
Lys Glu Ala Val Glu Ser Ala Asp Leu Ile Leu Ser Val Gly Ala Leu
        275                 280                 285 ttg tct gat ttc aac acc ggt tct ttc tct tac tct tac aag acc aag      912
Leu Ser Asp Phe Asn Thr Gly Ser Phe Ser Tyr Ser Tyr Lys Thr Lys
    290                 295                 300 aac att gtc gaa ttc cac tcc gac cac atg aag atc aga aac gcc act      960
Asn Ile Val Glu Phe His Ser Asp His Met Lys Ile Arg Asn Ala Thr
305                 310                 315                 320 ttc cca ggt gtc caa atg aaa ttc gtt ttg caa aag ttg ttg acc act     1008
Phe Pro Gly Val Gln Met Lys Phe Val Leu Gln Lys Leu Leu Thr Thr
                325                 330                 335 att gct gac gcc gct aag ggt tac aag cca gtt gct gtc cca gct aga     1056
Ile Ala Asp Ala Ala Lys Gly Tyr Lys Pro Val Ala Val Pro Ala Arg
            340                 345                 350 act cca gct aac gct gct gtc cca gct tct acc cca ttg aag caa gaa     1104
Thr Pro Ala Asn Ala Ala Val Pro Ala Ser Thr Pro Leu Lys Gln Glu
        355                 360                 365 tgg atg tgg aac caa ttg ggt aac ttc ttg caa gaa ggt gat gtt gtc     1152
Trp Met Trp Asn Gln Leu Gly Asn Phe Leu Gln Glu Gly Asp Val Val
    370                 375                 380 att gct gaa acc ggt acc tcc gct ttc ggt atc aac caa acc act ttc     1200
Ile Ala Glu Thr Gly Thr Ser Ala Phe Gly Ile Asn Gln Thr Thr Phe
385                 390                 395                 400 cca aac aac acc tac ggt atc tct caa gtc tta tgg ggt tcc att ggt     1248
Pro Asn Asn Thr Tyr Gly Ile Ser Gln Val Leu Trp Gly Ser Ile Gly
                405                 410                 415 ttc acc act ggt gct acc ttg ggt gct gct ttc gct gct gaa gaa att     1296
Phe Thr Thr Gly Ala Thr Leu Gly Ala Ala Phe Ala Ala Glu Glu Ile
            420                 425                 430 gat cca aag aag aga gtt atc tta ttc att ggt gac ggt tct ttg caa     1344
Asp Pro Lys Lys Arg Val Ile Leu Phe Ile Gly Asp Gly Ser Leu Gln
        435                 440                 445 ttg act gtt caa gaa atc tcc acc atg atc aga tgg ggc ttg aag cca     1392
Leu Thr Val Gln Glu Ile Ser Thr Met Ile Arg Trp Gly Leu Lys Pro
    450                 455                 460 tac ttg ttc gtc ttg aac aac gat ggt tac acc att gaa aag ttg att     1440
Tyr Leu Phe Val Leu Asn Asn Asp Gly Tyr Thr Ile Glu Lys Leu Ile
465                 470                 475                 480 cac ggt cca aag gct caa tac aac gaa att caa ggt tgg gac cac cta     1488
His Gly Pro Lys Ala Gln Tyr Asn Glu Ile Gln Gly Trp Asp His Leu
```

-continued

```
                       485                 490                 495
tcc ttg ttg cca act ttc ggt gct aag gac tat gaa acc cac aga gtc    1536
Ser Leu Leu Pro Thr Phe Gly Ala Lys Asp Tyr Glu Thr His Arg Val
            500                 505                 510 gct acc acc ggt gaa tgg gac aag ttg acc caa gac aag tct ttc aac    1584
Ala Thr Thr Gly Glu Trp Asp Lys Leu Thr Gln Asp Lys Ser Phe Asn
        515                 520                 525 gac aac tct aag atc aga atg att gaa atc atg ttg cca gtc ttc gat    1632
Asp Asn Ser Lys Ile Arg Met Ile Glu Ile Met Leu Pro Val Phe Asp
    530                 535                 540 gct cca caa aac ttg gtt gaa caa gct aag ttg act gct gct acc aac    1680
Ala Pro Gln Asn Leu Val Glu Gln Ala Lys Leu Thr Ala Ala Thr Asn
545                 550                 555                 560 gct aag caa taa                                                     1692
Ala Lys Gln <210> SEQ ID NO 34
<211> LENGTH: 563
<212> TYPE: PRT
<213> ORGANISM: Saccharomyces cerevisiae

<400> SEQUENCE: 34

Met Ser Glu Ile Thr Leu Gly Lys Tyr Leu Phe Glu Arg Leu Lys Gln
1               5                   10                  15

Val Asn Val Asn Thr Val Phe Gly Leu Pro Gly Asp Phe Asn Leu Ser
            20                  25                  30

Leu Leu Asp Lys Ile Tyr Glu Val Glu Gly Met Arg Trp Ala Gly Asn
        35                  40                  45

Ala Asn Glu Leu Asn Ala Ala Tyr Ala Ala Asp Gly Tyr Ala Arg Ile
    50                  55                  60

Lys Gly Met Ser Cys Ile Ile Thr Thr Phe Gly Val Gly Glu Leu Ser
65                  70                  75                  80

Ala Leu Asn Gly Ile Ala Gly Ser Tyr Ala Glu His Val Gly Val Leu
                85                  90                  95

His Val Val Gly Val Pro Ser Ile Ser Ala Gln Ala Lys Gln Leu Leu
            100                 105                 110

Leu His His Thr Leu Gly Asn Gly Asp Phe Thr Val Phe His Arg Met
        115                 120                 125

Ser Ala Asn Ile Ser Glu Thr Thr Ala Met Ile Thr Asp Ile Ala Thr
    130                 135                 140

Ala Pro Ala Glu Ile Asp Arg Cys Ile Arg Thr Thr Tyr Val Thr Gln
145                 150                 155                 160

Arg Pro Val Tyr Leu Gly Leu Pro Ala Asn Leu Val Asp Leu Asn Val
                165                 170                 175

Pro Ala Lys Leu Leu Gln Thr Pro Ile Asp Met Ser Leu Lys Pro Asn
            180                 185                 190

Asp Ala Glu Ser Glu Lys Glu Val Ile Asp Thr Ile Leu Ala Leu Val
        195                 200                 205

Lys Asp Ala Lys Asn Pro Val Ile Leu Ala Asp Ala Cys Cys Ser Arg
    210                 215                 220

His Asp Val Lys Ala Glu Thr Lys Lys Leu Ile Asp Leu Thr Gln Phe
225                 230                 235                 240

Pro Ala Phe Val Thr Pro Met Gly Lys Gly Ser Ile Asp Glu Gln His
                245                 250                 255

Pro Arg Tyr Gly Gly Val Tyr Val Gly Thr Leu Ser Lys Pro Glu Val
            260                 265                 270
```

```
Lys Glu Ala Val Glu Ser Ala Asp Leu Ile Leu Ser Val Gly Ala Leu
        275                 280                 285

Leu Ser Asp Phe Asn Thr Gly Ser Phe Ser Tyr Ser Tyr Lys Thr Lys
        290                 295                 300

Asn Ile Val Glu Phe His Ser Asp His Met Lys Ile Arg Asn Ala Thr
305                 310                 315                 320

Phe Pro Gly Val Gln Met Lys Phe Val Leu Gln Lys Leu Leu Thr Thr
                325                 330                 335

Ile Ala Asp Ala Ala Lys Gly Tyr Lys Pro Val Ala Val Pro Ala Arg
                340                 345                 350

Thr Pro Ala Asn Ala Ala Val Pro Ala Ser Thr Pro Leu Lys Gln Glu
        355                 360                 365

Trp Met Trp Asn Gln Leu Gly Asn Phe Leu Gln Glu Gly Asp Val Val
    370                 375                 380

Ile Ala Glu Thr Gly Thr Ser Ala Phe Gly Ile Asn Gln Thr Thr Phe
385                 390                 395                 400

Pro Asn Asn Thr Tyr Gly Ile Ser Gln Val Leu Trp Gly Ser Ile Gly
                405                 410                 415

Phe Thr Thr Gly Ala Thr Leu Gly Ala Ala Phe Ala Ala Glu Glu Ile
                420                 425                 430

Asp Pro Lys Lys Arg Val Ile Leu Phe Ile Gly Asp Gly Ser Leu Gln
        435                 440                 445

Leu Thr Val Gln Glu Ile Ser Thr Met Ile Arg Trp Gly Leu Lys Pro
    450                 455                 460

Tyr Leu Phe Val Leu Asn Asp Gly Tyr Thr Ile Glu Lys Leu Ile
465                 470                 475                 480

His Gly Pro Lys Ala Gln Tyr Asn Glu Ile Gln Gly Trp Asp His Leu
                485                 490                 495

Ser Leu Leu Pro Thr Phe Gly Ala Lys Asp Tyr Glu Thr His Arg Val
                500                 505                 510

Ala Thr Thr Gly Glu Trp Asp Lys Leu Thr Gln Asp Lys Ser Phe Asn
        515                 520                 525

Asp Asn Ser Lys Ile Arg Met Ile Glu Ile Met Leu Pro Val Phe Asp
530                 535                 540

Ala Pro Gln Asn Leu Val Glu Gln Ala Lys Leu Thr Ala Ala Thr Asn
545                 550                 555                 560

Ala Lys Gln

<210> SEQ ID NO 35
<211> LENGTH: 1692
<212> TYPE: DNA
<213> ORGANISM: Artificial
<220> FEATURE:
<223> OTHER INFORMATION: Saccharomyces cerevisiae pyruvate decarboxylase
      Pdc codon optimised gene

<400> SEQUENCE: 35
atgtccgaga tcactctggg caaatacctg tttgaacgtc tgaaacaggt gaacgttaat     60
accgtattcg gcctgccggg tgatttcaac ctgtccctgc tggacaaaat ctatgaagtt    120
gaaggtatgc gttgggctgg caacgctaac gagctgaacg cagcgtacgc ggcagatggt    180
tacgctcgta tcaaaggtat gtcttgtatc atcaccacct tcggtgttgg tgagctgagc    240
gccctgaacg gcatcgccgg ctcctatgca gagcacgtgg gcgtgctgca cgttgtgggt    300
gtaccgtcca tcagcgccca ggcaaaacag ctgctgctgc accacaccct gggtaacggc    360
```

-continued

```
gactttaccg ttttccatcg tatgtctgcg aacatcagcg aaactactgc aatgattact      420
gacatcgcta cggcaccggc agaaatcgac cgttgcattc gtaccacgta cgttactcag      480
cgcccggttt atctgggcct gccagccaac ctggtggatc tgaacgtccc ggctaaactg      540
ctgcagactc cgatcgatat gtctctgaaa cctaacgacg cagaatctga aaagaagtt       600 atcgatacta ttctggctct ggtgaaagat gcaagaacc cagttatcct ggctgacgca       660
tgttgctctc gtcatgatgt aaaggcagaa accaaaaagc tgatcgacct gacgcagttc      720
ccggcgttcg ttaccccgat gggcaagggt tccatcgatg agcagcaccc gcgttatggt      780
ggtgtatacg ttggcacgct gtccaaaccg gaggtaaaag aagcggttga aagcgcagat      840
ctgatcctgt ctgttggtgc actgctgagc gacttcaaca ccggttcttt ctcctatagc      900
tacaagacca aaaacattgt ggagtttcac tccgatcaca tgaaaatccg caacgcgacc      960
tttcctggtg tgcagatgaa attcgtactg cagaaactgc tgaccaccat cgccgacgct     1020
gcgaaaggtt ataaaccggt agctgtgccg gcacgtaccc cggcgaacgc cgcggttcct     1080
gcatccactc cactgaagca ggaatggatg tggaatcagc tgggtaattt cctgcaagaa     1140
ggcgacgttg taatcgcaga aaccggcact agcgcgtttg cattaaccaa gacgaccttc     1200
ccaaacaaca cctacggtat cagccaagtc ctgtggggct ctatcggctt caccaccggt     1260
gcaaccctgg gtgcggcttt cgctgctgag gagatcgacc cgaagaaacg tgttatcctg     1320
ttcatcggtg acggctccct gcagctgacc gtccaggaga tttctaccat gatccgctgg     1380
ggcctgaaac cgtacctgtt tgtgctgaac aacgacggct acactattga gaaactgatc     1440
cacggtccga agcacagta taatgagatc cagggttggg atcatctgtc tctgctgccg     1500
acctttggcg ctaaagacta cgagaccac cgcgtggcta ccaccggcga gtgggataaa     1560
ctgacgcagg ataaatcctt caatgacaat agcaagattc gtatgatcga aatcatgctg     1620
ccggtctttg atgctccgca gaacctggta gagcaagcaa aactgaccgc ggcaactaac     1680
gctaaacagt aa                                                         1692
```

```
<210> SEQ ID NO 36
<211> LENGTH: 1707
<212> TYPE: DNA
<213> ORGANISM: Zymomonas mobilis
<220> FEATURE:
<221> NAME/KEY: CDS
<222> LOCATION: (1)..(1707)

<400> SEQUENCE: 36
```

```
atg agt tat act gtc ggt acc tat tta gcg gag cgg ctt gtc cag att      48
Met Ser Tyr Thr Val Gly Thr Tyr Leu Ala Glu Arg Leu Val Gln Ile
1               5                   10                  15 ggt ctc aag cat cac ttc gca gtc gcg ggc gac tac aac ctc gtc ctt      96
Gly Leu Lys His His Phe Ala Val Ala Gly Asp Tyr Asn Leu Val Leu
            20                  25                  30 ctt gac aac ctg ctt ttg aac aaa aac atg gag cag gtt tat tgc tgt     144
Leu Asp Asn Leu Leu Leu Asn Lys Asn Met Glu Gln Val Tyr Cys Cys
        35                  40                  45 aac gaa ctg aac tgc ggt ttc agt gca gaa ggt tat gct cgt gcc aaa     192
Asn Glu Leu Asn Cys Gly Phe Ser Ala Glu Gly Tyr Ala Arg Ala Lys
    50                  55                  60 ggc gca gca gca gcc gtc gtt acc tac agc gtc ggt gcg ctt tcc gca     240
Gly Ala Ala Ala Ala Val Val Thr Tyr Ser Val Gly Ala Leu Ser Ala
65                  70                  75                  80 ttt gat gct atc ggt ggc gcc tat gca gaa aac ctt ccg gtt atc ctg     288
```

```
                Phe Asp Ala Ile Gly Gly Ala Tyr Ala Glu Asn Leu Pro Val Ile Leu
                                85                  90                  95 atc tcc ggt gct ccg aac aac aat gat cac gct gct ggt cac gtg ttg        336
Ile Ser Gly Ala Pro Asn Asn Asn Asp His Ala Ala Gly His Val Leu
        100                 105                 110 cat cac gct ctt ggc aaa acc gac tat cac tat cag ttg gaa atg gcc        384
His His Ala Leu Gly Lys Thr Asp Tyr His Tyr Gln Leu Glu Met Ala
            115                 120                 125 aag aac atc acg gcc gcc gct gaa gcg att tac acc ccg gaa gaa gct        432
Lys Asn Ile Thr Ala Ala Ala Glu Ala Ile Tyr Thr Pro Glu Glu Ala
130                 135                 140 ccg gct aaa atc gat cac gtg att aaa act gct ctt cgt gag aag aag        480
Pro Ala Lys Ile Asp His Val Ile Lys Thr Ala Leu Arg Glu Lys Lys
145                 150                 155                 160 ccg gtt tat ctc gaa atc gct tgc aac att gct tcc atg ccc tgc gcc        528
Pro Val Tyr Leu Glu Ile Ala Cys Asn Ile Ala Ser Met Pro Cys Ala
                165                 170                 175 gct cct gga ccg gca agc gca ttg ttc aat gac gaa gcc agc gac gaa        576
Ala Pro Gly Pro Ala Ser Ala Leu Phe Asn Asp Glu Ala Ser Asp Glu
            180                 185                 190 gct tct ttg aat gca gcg gtt gaa gaa acc ctg aaa ttc atc gcc aac        624
Ala Ser Leu Asn Ala Ala Val Glu Glu Thr Leu Lys Phe Ile Ala Asn
        195                 200                 205 cgc gac aaa gtt gcc gtc ctc gtc ggc agc aag ctg cgc gca gct ggt        672
Arg Asp Lys Val Ala Val Leu Val Gly Ser Lys Leu Arg Ala Ala Gly
210                 215                 220 gct gaa gaa gct gct gtc aaa ttt gct gat gct ctc ggt ggc gca gtt        720
Ala Glu Glu Ala Ala Val Lys Phe Ala Asp Ala Leu Gly Gly Ala Val
225                 230                 235                 240 gct acc atg gct gct gca aaa agc ttc ttc cca gaa gaa aac ccg cat        768
Ala Thr Met Ala Ala Ala Lys Ser Phe Phe Pro Glu Glu Asn Pro His
                245                 250                 255 tac atc ggc acc tca tgg ggt gaa gtc agc tat ccg ggc gtt gaa aag        816
Tyr Ile Gly Thr Ser Trp Gly Glu Val Ser Tyr Pro Gly Val Glu Lys
            260                 265                 270 acg atg aaa gaa gcc gat gcg gtt atc gct ctg gct cct gtc ttc aac        864
Thr Met Lys Glu Ala Asp Ala Val Ile Ala Leu Ala Pro Val Phe Asn
        275                 280                 285 gac tac tcc acc act ggt tgg acg gat att cct gat cct aag aaa ctg        912
Asp Tyr Ser Thr Thr Gly Trp Thr Asp Ile Pro Asp Pro Lys Lys Leu
        290                 295                 300 gtt ctc gct gaa ccg cgt tct gtc gtt aac ggc att cgc ttc ccc            960
Val Leu Ala Glu Pro Arg Ser Val Val Asn Gly Ile Arg Phe Pro
305                 310                 315                 320 agc gtc cat ctg aaa gac tat ctg acc cgt ttg gct cag aaa gtt tcc       1008
Ser Val His Leu Lys Asp Tyr Leu Thr Arg Leu Ala Gln Lys Val Ser
                325                 330                 335 aag aaa acc ggt gca ttg gac ttc ttc aaa tcc ctc aat gca ggt gaa       1056
Lys Lys Thr Gly Ala Leu Asp Phe Phe Lys Ser Leu Asn Ala Gly Glu
            340                 345                 350 ctg aag aaa gcc gct ccg gct gat ccg agt gct ccg ttg gtc aac gca       1104
Leu Lys Lys Ala Ala Pro Ala Asp Pro Ser Ala Pro Leu Val Asn Ala
        355                 360                 365 gaa atc gcc cgt cag gtc gaa gct ctt ctg acc ccg aac acg acg gtt       1152
Glu Ile Ala Arg Gln Val Glu Ala Leu Leu Thr Pro Asn Thr Thr Val
370                 375                 380 att gct gaa acc ggt gac tct tgg ttc aat gct cag cgc atg aag ctc       1200
Ile Ala Glu Thr Gly Asp Ser Trp Phe Asn Ala Gln Arg Met Lys Leu
385                 390                 395                 400
```

| | | | | | | | | | | | | | | | |
|---|---|---|---|---|---|---|---|---|---|---|---|---|---|---|---|
| ccg | aac | ggt | gct | cgc | gtt | gaa | tat | gaa | atg | cag | tgg | ggt | cac | att | ggt | 1248 |
| Pro | Asn | Gly | Ala | Arg | Val | Glu | Tyr | Glu | Met | Gln | Trp | Gly | His | Ile | Gly |
| | | | 405 | | | | | 410 | | | | | 415 | | |

```
ccg aac ggt gct cgc gtt gaa tat gaa atg cag tgg ggt cac att ggt      1248
Pro Asn Gly Ala Arg Val Glu Tyr Glu Met Gln Trp Gly His Ile Gly
            405                 410                 415 tgg tcc gtt cct gcc gcc ttc ggt tat gcc gtc ggt gct ccg gaa cgt      1296
Trp Ser Val Pro Ala Ala Phe Gly Tyr Ala Val Gly Ala Pro Glu Arg
        420                 425                 430 cgc aac atc ctc atg gtt ggt gat ggt tcc ttc cag ctg acg gct cag      1344
Arg Asn Ile Leu Met Val Gly Asp Gly Ser Phe Gln Leu Thr Ala Gln
            435                 440                 445 gaa gtc gct cag atg gtt cgc ctg aaa ctg ccg gtt atc atc ttc ttg      1392
Glu Val Ala Gln Met Val Arg Leu Lys Leu Pro Val Ile Ile Phe Leu
        450                 455                 460 atc aat aac tat ggt tac acc gcc gaa gtt atg atc cat gat ggt ccg      1440
Ile Asn Asn Tyr Gly Tyr Thr Ala Glu Val Met Ile His Asp Gly Pro
465                 470                 475                 480 tac aac aac atc aag aac tgg gat tat gcc ggt ctg atg gaa gtg ttc      1488
Tyr Asn Asn Ile Lys Asn Trp Asp Tyr Ala Gly Leu Met Glu Val Phe
                485                 490                 495 aac ggt aac ggt ggt tat gac agc ggt gct ggt aaa ggc ctg aag gct      1536
Asn Gly Asn Gly Gly Tyr Asp Ser Gly Ala Gly Lys Gly Leu Lys Ala
            500                 505                 510 aaa acc ggt ggc gaa ctg gca gaa gct atc aag gtt gct ctg gca aac      1584
Lys Thr Gly Gly Glu Leu Ala Glu Ala Ile Lys Val Ala Leu Ala Asn
            515                 520                 525 acc gac ggc cca acc ctg atc gaa tgc ttc atc ggt cgt gaa gac tgc      1632
Thr Asp Gly Pro Thr Leu Ile Glu Cys Phe Ile Gly Arg Glu Asp Cys
        530                 535                 540 act gaa gaa ttg gtc aaa tgg ggt aag cgc gtt gct gcc gcc aac agc      1680
Thr Glu Glu Leu Val Lys Trp Gly Lys Arg Val Ala Ala Ala Asn Ser
545                 550                 555                 560 cgt aag cct gtt aac aag ctc ctc tag                                  1707
Arg Lys Pro Val Asn Lys Leu Leu
                565
```

<210> SEQ ID NO 37
<211> LENGTH: 568
<212> TYPE: PRT
<213> ORGANISM: Zymomonas mobilis

<400> SEQUENCE: 37

```
Met Ser Tyr Thr Val Gly Thr Tyr Leu Ala Glu Arg Leu Val Gln Ile
1               5                   10                  15

Gly Leu Lys His His Phe Ala Val Ala Gly Asp Tyr Asn Leu Val Leu
            20                  25                  30

Leu Asp Asn Leu Leu Leu Asn Lys Asn Met Glu Gln Val Tyr Cys Cys
        35                  40                  45

Asn Glu Leu Asn Cys Gly Phe Ser Ala Glu Gly Tyr Ala Arg Ala Lys
    50                  55                  60

Gly Ala Ala Ala Val Val Thr Tyr Ser Val Gly Ala Leu Ser Ala
65                  70                  75                  80

Phe Asp Ala Ile Gly Gly Ala Tyr Ala Glu Asn Leu Pro Val Ile Leu
                85                  90                  95

Ile Ser Gly Ala Pro Asn Asn Asn Asp His Ala Ala Gly His Val Leu
            100                 105                 110

His His Ala Leu Gly Lys Thr Asp Tyr His Tyr Gln Leu Glu Met Ala
        115                 120                 125

Lys Asn Ile Thr Ala Ala Ala Glu Ala Ile Tyr Thr Pro Glu Glu Ala
    130                 135                 140
```

-continued

```
Pro Ala Lys Ile Asp His Val Ile Lys Thr Ala Leu Arg Glu Lys Lys
145                 150                 155                 160

Pro Val Tyr Leu Glu Ile Ala Cys Asn Ile Ala Ser Met Pro Cys Ala
                165                 170                 175

Ala Pro Gly Pro Ala Ser Ala Leu Phe Asn Asp Glu Ala Ser Asp Glu
            180                 185                 190

Ala Ser Leu Asn Ala Ala Val Glu Glu Thr Leu Lys Phe Ile Ala Asn
        195                 200                 205

Arg Asp Lys Val Ala Val Leu Val Gly Ser Lys Leu Arg Ala Ala Gly
    210                 215                 220

Ala Glu Ala Ala Val Lys Phe Ala Asp Ala Leu Gly Gly Ala Val
225                 230                 235                 240

Ala Thr Met Ala Ala Lys Ser Phe Phe Pro Glu Glu Asn Pro His
                245                 250                 255

Tyr Ile Gly Thr Ser Trp Gly Glu Val Ser Tyr Pro Gly Val Glu Lys
            260                 265                 270

Thr Met Lys Glu Ala Asp Ala Val Ile Ala Leu Ala Pro Val Phe Asn
        275                 280                 285

Asp Tyr Ser Thr Thr Gly Trp Thr Asp Ile Pro Asp Pro Lys Lys Leu
    290                 295                 300

Val Leu Ala Glu Pro Arg Ser Val Val Asn Gly Ile Arg Phe Pro
305                 310                 315                 320

Ser Val His Leu Lys Asp Tyr Leu Thr Arg Leu Ala Gln Lys Val Ser
                325                 330                 335

Lys Lys Thr Gly Ala Leu Asp Phe Phe Lys Ser Leu Asn Ala Gly Glu
            340                 345                 350

Leu Lys Lys Ala Ala Pro Ala Asp Pro Ser Ala Pro Leu Val Asn Ala
        355                 360                 365

Glu Ile Ala Arg Gln Val Glu Ala Leu Leu Thr Pro Asn Thr Thr Val
    370                 375                 380

Ile Ala Glu Thr Gly Asp Ser Trp Phe Asn Ala Gln Arg Met Lys Leu
385                 390                 395                 400

Pro Asn Gly Ala Arg Val Glu Tyr Glu Met Gln Trp Gly His Ile Gly
                405                 410                 415

Trp Ser Val Pro Ala Ala Phe Gly Tyr Ala Val Gly Ala Pro Glu Arg
            420                 425                 430

Arg Asn Ile Leu Met Val Gly Asp Gly Ser Phe Gln Leu Thr Ala Gln
        435                 440                 445

Glu Val Ala Gln Met Val Arg Leu Lys Leu Pro Val Ile Ile Phe Leu
    450                 455                 460

Ile Asn Asn Tyr Gly Tyr Thr Ala Glu Val Met Ile His Asp Gly Pro
465                 470                 475                 480

Tyr Asn Asn Ile Lys Asn Trp Asp Tyr Ala Gly Leu Met Glu Val Phe
                485                 490                 495

Asn Gly Asn Gly Gly Tyr Asp Ser Gly Ala Gly Lys Gly Leu Lys Ala
            500                 505                 510

Lys Thr Gly Gly Glu Leu Ala Glu Ala Ile Lys Val Ala Leu Ala Asn
        515                 520                 525

Thr Asp Gly Pro Thr Leu Ile Glu Cys Phe Ile Gly Arg Glu Asp Cys
    530                 535                 540

Thr Glu Glu Leu Val Lys Trp Gly Lys Arg Val Ala Ala Ala Asn Ser
545                 550                 555                 560

Arg Lys Pro Val Asn Lys Leu Leu
```

<210> SEQ ID NO 38
<211> LENGTH: 1707
<212> TYPE: DNA
<213> ORGANISM: Artificial
<220> FEATURE:
<223> OTHER INFORMATION: Zymomonas mobilis pyruvate decarboxylase PdcI472A codon optimised gene

<400> SEQUENCE: 38

```
atgtcttata ctgttggtac ttatctggct gagcgtctgg tgcaaatcgg cctgaaacac      60
cactttgcag ttgctggcga ctacaacctg gttctgctgg ataacctgct gctgaacaaa     120
aacatggagc aagtttattg ctgtaacgag ctgaactgcg gcttctctgc ggagggttat     180
gcgcgtgcga aggtgccgc tgcagcagtc gtaacctact ctgtgggcgc tctgtccgcg     240
ttcgacgcaa tcggtggcgc ttacgctgaa aacctgccgg tgatcctgat agcggtgcg     300
ccgaataata acgaccatgc tgctggccac gttctgcacc acgccctggg taaaactgat     360
taccattacc agctggagat ggctaaaaac atcactgcag cagcagaagc gatctacacc     420
ccggaagagg ctccggcaaa aatcgaccac gtgattaaaa ccgctctgcg tgagaaaaag     480
ccggtatacc tggaaatcgc gtgcaacatc gcgtctatgc cgtgcgccgc accgggtccg     540
gcttctgccc tgttcaacga tgaggcgagc gatgaggcat ctctgaacgc agcagtagaa     600
gaaaccctga aatttatcgc aaaccgtgac aaagtagcag tcctggtagg ttctaaactg     660
cgtgcggctg gtgcggaaga ggctgcggta aagttcgcgg atgctctggg cggtgcagtg     720
gcgaccatgg cagcggctaa atccttcttc ccagaggaga accgcatta cattggtacc     780
tcctggggcg aagtttccta ccctggtgtg agaaaaacca tgaaagaagc gatgctgtg     840
attgccctgg cgcctgtatt caacgattat tccaccaccg gttggaccga tatcccggac     900
ccgaagaaac tggtcctggc tgaaccgcgc tccgtagtag tgaatggcat tcgtttcccg     960
tccgtacacc tgaaggatta cctgacgcgt ctggcacaga agtatccaa gaaaactggc    1020
gcgctggact tctttaaatc cctgaacgct ggtgagctga aaaaggcggc tccggccgat    1080
ccgtccgcac cgctggtgaa cgcagagatt gcacgtcagg ttgaggcact gctgacgccg    1140
aacaccaccg taatcgcgga aacgggcgac tcttggttca acgcacagcg catgaaactg    1200
ccgaacggtg cccgcgttga atatgaaatg cagtgggggtc acatcggctg gtctgtccca    1260
gcagcgtttg ttacgcggt tggtgcaccg gagcgtcgca acatcctgat ggtgggtgac    1320
ggctccttcc agctgactgc tcaggagtg gcgcagatgg tgcgcctgaa gctgccggtt    1380
atcattttcc tgatcaacaa ctacggctac accgccgagg taatgatcca cgatggtccg    1440
tacaacaaca tcaaaaactg ggactacgcc ggtctgatgg aggttttaa cggtaacggc    1500
ggttacgaca gcggtgctgg taagggtctg aaagccaaaa ccggtggcga actggcagag    1560
gcgattaaag ttgcgctggc aaacaccgat ggcccgaccc tgatcgagtg cttcatcggc    1620
cgtgaggact gcaccgagga gctggtcaaa tgggcaaac gtgtggcggc tgctaactct    1680
cgcaagccgg taaacaaact gctgtaa                                       1707
```

<210> SEQ ID NO 39
<211> LENGTH: 1644
<212> TYPE: DNA
<213> ORGANISM: Lactococcus lactis
<220> FEATURE:
<221> NAME/KEY: CDS
<222> LOCATION: (1)..(1644)

<400> SEQUENCE: 39

```
atg tat aca gta gga gat tac ctg tta gac cga tta cac gag ttg gga      48
Met Tyr Thr Val Gly Asp Tyr Leu Leu Asp Arg Leu His Glu Leu Gly
1               5                   10                  15 att gaa gaa att ttt gga gtt cct ggt gac tat aac tta caa ttt tta      96
Ile Glu Glu Ile Phe Gly Val Pro Gly Asp Tyr Asn Leu Gln Phe Leu
                20                  25                  30 gat caa att att tca cgc gaa gat atg aaa tgg att gga aat gct aat     144
Asp Gln Ile Ile Ser Arg Glu Asp Met Lys Trp Ile Gly Asn Ala Asn
            35                  40                  45 gaa tta aat gct tct tat atg gct gat ggt tat gct cgt act aaa aaa     192
Glu Leu Asn Ala Ser Tyr Met Ala Asp Gly Tyr Ala Arg Thr Lys Lys
        50                  55                  60 gct gcc gca ttt ctc acc aca ttt gga gtc ggc gaa ttg agt gcg atc     240
Ala Ala Ala Phe Leu Thr Thr Phe Gly Val Gly Glu Leu Ser Ala Ile
65                  70                  75                  80 aat gga ctg gca gga agt tat gcc gaa aat tta cca gta gta gaa att     288
Asn Gly Leu Ala Gly Ser Tyr Ala Glu Asn Leu Pro Val Val Glu Ile
                85                  90                  95 gtt ggt tca cca act tca aaa gta caa aat gac gga aaa ttt gtc cat     336
Val Gly Ser Pro Thr Ser Lys Val Gln Asn Asp Gly Lys Phe Val His
                100                 105                 110 cat aca cta gca gat ggt gat ttt aaa cac ttt atg aag atg cat gaa     384
His Thr Leu Ala Asp Gly Asp Phe Lys His Phe Met Lys Met His Glu
            115                 120                 125 cct gtt aca gca gcg cgg act tta ctg aca gca gaa aat gcc aca tat     432
Pro Val Thr Ala Ala Arg Thr Leu Leu Thr Ala Glu Asn Ala Thr Tyr
        130                 135                 140 gaa att gac cga gta ctt tct caa tta cta aaa gaa aga aaa cca gtc     480
Glu Ile Asp Arg Val Leu Ser Gln Leu Leu Lys Glu Arg Lys Pro Val
145                 150                 155                 160 tat att aac tta cca gtc gat gtt gct gca gca aaa gca gag aag cct     528
Tyr Ile Asn Leu Pro Val Asp Val Ala Ala Ala Lys Ala Glu Lys Pro
                165                 170                 175 gca tta tct tta gaa aaa gaa agc tct aca aca aat aca act gaa caa     576
Ala Leu Ser Leu Glu Lys Glu Ser Ser Thr Thr Asn Thr Thr Glu Gln
                180                 185                 190 gtg att ttg agt aag att gaa gaa agt ttg aaa aat gcc caa aaa cca     624
Val Ile Leu Ser Lys Ile Glu Glu Ser Leu Lys Asn Ala Gln Lys Pro
            195                 200                 205 gta gtg att gca gga cac gaa gta att agt ttt ggt tta gaa aaa acg     672
Val Val Ile Ala Gly His Glu Val Ile Ser Phe Gly Leu Glu Lys Thr
        210                 215                 220 gta act cag ttt gtt tca gaa aca aaa cta ccg att acg aca cta aat     720
Val Thr Gln Phe Val Ser Glu Thr Lys Leu Pro Ile Thr Thr Leu Asn
225                 230                 235                 240 ttt ggt aaa agt gct gtt gat gaa tct ttg ccc tca ttt tta gga ata     768
Phe Gly Lys Ser Ala Val Asp Glu Ser Leu Pro Ser Phe Leu Gly Ile
                245                 250                 255 tat aac ggg aaa ctt tca gaa atc agt ctt aaa aat ttt gtg gag tcc     816
Tyr Asn Gly Lys Leu Ser Glu Ile Ser Leu Lys Asn Phe Val Glu Ser
                260                 265                 270 gca gac ttt atc cta atg ctt gga gtg aag ctt acg gac tcc tca aca     864
Ala Asp Phe Ile Leu Met Leu Gly Val Lys Leu Thr Asp Ser Ser Thr
            275                 280                 285 ggt gca ttc aca cat cat tta gat gaa aat aaa atg att tca cta aac     912
Gly Ala Phe Thr His His Leu Asp Glu Asn Lys Met Ile Ser Leu Asn
        290                 295                 300
```

| | | |
|---|---|---|
| ata gat gaa gga ata att ttc aat aaa gtg gta gaa gat ttt gat ttt<br>Ile Asp Glu Gly Ile Ile Phe Asn Lys Val Val Glu Asp Phe Asp Phe<br>305                        310                     315                   320 | 960 | |
| aga gca gtg gtt tct tct tta tca gaa tta aaa gga ata gaa tat gaa<br>Arg Ala Val Val Ser Ser Leu Ser Glu Leu Lys Gly Ile Glu Tyr Glu<br>                        325                     330                     335 | 1008 | |
| gga caa tat att gat aag caa tat gaa gaa ttt att cca tca agt gct<br>Gly Gln Tyr Ile Asp Lys Gln Tyr Glu Glu Phe Ile Pro Ser Ser Ala<br>                  340                    345                    350 | 1056 | |
| ccc tta tca caa gac cgt cta tgg cag gca gtt gaa agt ttg act caa<br>Pro Leu Ser Gln Asp Arg Leu Trp Gln Ala Val Glu Ser Leu Thr Gln<br>        355                    360                    365 | 1104 | |
| agc aat gaa aca atc gtt gct gaa caa gga acc tca ttt ttt gga gct<br>Ser Asn Glu Thr Ile Val Ala Glu Gln Gly Thr Ser Phe Phe Gly Ala<br>370                        375                     380 | 1152 | |
| tca aca att ttc tta aaa tca aat agt cgt ttt att gga caa cct tta<br>Ser Thr Ile Phe Leu Lys Ser Asn Ser Arg Phe Ile Gly Gln Pro Leu<br>385                        390                     395                   400 | 1200 | |
| tgg ggt tct att gga tat act ttt cca gcg gct tta gga agc caa att<br>Trp Gly Ser Ile Gly Tyr Thr Phe Pro Ala Ala Leu Gly Ser Gln Ile<br>                             405                    410                    415 | 1248 | |
| gcg gat aaa gag agc aga cac ctt tta ttt att ggt gat ggt tca ctt<br>Ala Asp Lys Glu Ser Arg His Leu Leu Phe Ile Gly Asp Gly Ser Leu<br>        420                    425                    430 | 1296 | |
| caa ctt acc gta caa gaa tta gga cta tca atc aga gaa aaa ctc aat<br>Gln Leu Thr Val Gln Glu Leu Gly Leu Ser Ile Arg Glu Lys Leu Asn<br>             435                    440                    445 | 1344 | |
| cca att tgt ttt atc ata aat aat gat ggt tat aca gtt gaa aga gaa<br>Pro Ile Cys Phe Ile Ile Asn Asn Asp Gly Tyr Thr Val Glu Arg Glu<br>450                        455                     460 | 1392 | |
| atc cac gga cct act caa agt tat aac gac att cca atg tgg aat tac<br>Ile His Gly Pro Thr Gln Ser Tyr Asn Asp Ile Pro Met Trp Asn Tyr<br>465                        470                    475                   480 | 1440 | |
| tcg aaa tta cca gaa aca ttt gga gca aca gaa gat cgt gta gta tca<br>Ser Lys Leu Pro Glu Thr Phe Gly Ala Thr Glu Asp Arg Val Val Ser<br>                        485                    490                    495 | 1488 | |
| aaa att gtt aga aca gag aat gaa ttt gtg tct gtc atg aaa gaa gcc<br>Lys Ile Val Arg Thr Glu Asn Glu Phe Val Ser Val Met Lys Glu Ala<br>        500                    505                    510 | 1536 | |
| caa gca gat gtc aat aga atg tat tgg ata gaa cta gtt ttg gaa aaa<br>Gln Ala Asp Val Asn Arg Met Tyr Trp Ile Glu Leu Val Leu Glu Lys<br>             515                    520                    525 | 1584 | |
| gaa gat gcg cca aaa tta ctg aaa aaa atg ggt aaa tta ttt gct gag<br>Glu Asp Ala Pro Lys Leu Leu Lys Lys Met Gly Lys Leu Phe Ala Glu<br>530                        535                     540 | 1632 | |
| caa aat aaa tag<br>Gln Asn Lys<br>545 | 1644 | |

<210> SEQ ID NO 40
<211> LENGTH: 547
<212> TYPE: PRT
<213> ORGANISM: Lactococcus lactis

<400> SEQUENCE: 40

Met Tyr Thr Val Gly Asp Tyr Leu Leu Asp Arg Leu His Glu Leu Gly
1                 5                   10                 15

Ile Glu Glu Ile Phe Gly Val Pro Gly Asp Tyr Asn Leu Gln Phe Leu
               20                   25                 30

Asp Gln Ile Ile Ser Arg Glu Asp Met Lys Trp Ile Gly Asn Ala Asn

```
            35                  40                  45
Glu Leu Asn Ala Ser Tyr Met Ala Asp Gly Tyr Ala Arg Thr Lys Lys
 50                  55                  60

Ala Ala Ala Phe Leu Thr Thr Phe Gly Val Gly Glu Leu Ser Ala Ile
 65                  70                  75                  80

Asn Gly Leu Ala Gly Ser Tyr Ala Glu Asn Leu Pro Val Val Glu Ile
                 85                  90                  95

Val Gly Ser Pro Thr Ser Lys Val Gln Asn Asp Gly Lys Phe Val His
            100                 105                 110

His Thr Leu Ala Asp Gly Asp Phe Lys His Phe Met Lys Met His Glu
        115                 120                 125

Pro Val Thr Ala Ala Arg Thr Leu Leu Thr Ala Glu Asn Ala Thr Tyr
130                 135                 140

Glu Ile Asp Arg Val Leu Ser Gln Leu Leu Lys Glu Arg Lys Pro Val
145                 150                 155                 160

Tyr Ile Asn Leu Pro Val Asp Val Ala Ala Lys Ala Glu Lys Pro
                165                 170                 175

Ala Leu Ser Leu Glu Lys Glu Ser Ser Thr Asn Thr Thr Glu Gln
            180                 185                 190

Val Ile Leu Ser Lys Ile Glu Ser Leu Lys Asn Ala Gln Lys Pro
        195                 200                 205

Val Val Ile Ala Gly His Glu Val Ile Ser Phe Gly Leu Glu Lys Thr
210                 215                 220

Val Thr Gln Phe Val Ser Glu Thr Lys Leu Pro Ile Thr Thr Leu Asn
225                 230                 235                 240

Phe Gly Lys Ser Ala Val Asp Glu Ser Leu Pro Ser Phe Leu Gly Ile
                245                 250                 255

Tyr Asn Gly Lys Leu Ser Glu Ile Ser Leu Lys Asn Phe Val Glu Ser
            260                 265                 270

Ala Asp Phe Ile Leu Met Leu Gly Val Lys Leu Thr Asp Ser Ser Thr
        275                 280                 285

Gly Ala Phe Thr His His Leu Asp Glu Asn Lys Met Ile Ser Leu Asn
290                 295                 300

Ile Asp Glu Gly Ile Ile Phe Asn Lys Val Val Glu Asp Phe Asp Phe
305                 310                 315                 320

Arg Ala Val Val Ser Ser Leu Ser Glu Leu Lys Gly Ile Glu Tyr Glu
                325                 330                 335

Gly Gln Tyr Ile Asp Lys Gln Tyr Glu Glu Phe Ile Pro Ser Ser Ala
            340                 345                 350

Pro Leu Ser Gln Asp Arg Leu Trp Gln Ala Val Glu Ser Leu Thr Gln
        355                 360                 365

Ser Asn Glu Thr Ile Val Ala Glu Gln Gly Thr Ser Phe Phe Gly Ala
370                 375                 380

Ser Thr Ile Phe Leu Lys Ser Asn Ser Arg Phe Ile Gly Gln Pro Leu
385                 390                 395                 400

Trp Gly Ser Ile Gly Tyr Thr Phe Pro Ala Ala Leu Gly Ser Gln Ile
                405                 410                 415

Ala Asp Lys Glu Ser Arg His Leu Leu Phe Ile Gly Asp Gly Ser Leu
            420                 425                 430

Gln Leu Thr Val Gln Glu Leu Gly Leu Ser Ile Arg Glu Lys Leu Asn
        435                 440                 445

Pro Ile Cys Phe Ile Ile Asn Asn Asp Gly Tyr Thr Val Glu Arg Glu
450                 455                 460
```

```
Ile His Gly Pro Thr Gln Ser Tyr Asn Asp Ile Pro Met Trp Asn Tyr
465                 470                 475                 480

Ser Lys Leu Pro Glu Thr Phe Gly Ala Thr Glu Asp Arg Val Val Ser
                485                 490                 495

Lys Ile Val Arg Thr Glu Asn Glu Phe Val Ser Val Met Lys Glu Ala
            500                 505                 510

Gln Ala Asp Val Asn Arg Met Tyr Trp Ile Glu Leu Val Leu Glu Lys
        515                 520                 525

Glu Asp Ala Pro Lys Leu Leu Lys Lys Met Gly Lys Leu Phe Ala Glu
    530                 535                 540

Gln Asn Lys
545

<210> SEQ ID NO 41
<211> LENGTH: 1644
<212> TYPE: DNA
<213> ORGANISM: Artificial
<220> FEATURE:
<223> OTHER INFORMATION: Lactococcus lactis branched chain alpha-
      ketoacid decarboxylase KdcA codon optimised gene

<400> SEQUENCE: 41
atgtatactg ttggtgatta tctgctggac cgtctgcatg aactgggcat tgaagaaatc      60
ttcggtgtcc aggcgactta caacctgcag ttcctggacc agatcatctc ccgcgaagat    120
atgaaatgga tcggtaacgc aaacgagctg aacgcgtctt atatggctga tggttatgct    180
cgcaccaaaa aggctgcggc ctttctgacc acctttggtg tgggcgagct gagcgcgatc    240
aacggcctgg caggttccta cgctgagaac ctgccggtag tagaaatcgt tggttccccg    300
acctctaagg ttcagaacga cggcaaattc gtacatcaca ccctggcgga cggcgatttt    360 aagcactttta tgaaaatgca cgaaccggtc accgccgctc gcactctgct gaccgcggaa    420
aacgcaacgt acgagatcga tcgtgtactg tcccagctgc tgaaagaacg taaaccggtg    480
tatatcaatc tgccggttga tgtcgctgcg gccaaagcag agaaaccggc actgtccctg    540
gagaaggaga gctccactac taacaccacc gaacaggtta tcctgtccaa aattgaagaa    600
tctctgaaaa acgcacagaa accggtggtt atcgcaggtc acgaggttat ctccttcggc    660
ctggagaaaa ctgttactca attcgtctct gaaacgaaac tgccgatcac gaccctgaac    720 tttgcaagt ccgcagttga cgaatctctg cctcttttcc tgggcattta acggcaaa    780 ctgtccgaga tctcccctgaa gaacttcgta gaatccgctg actttatcct gatgctgggt    840
gtgaaactga ccgactcctc taccggtgcg ttcacgcacc atctggatga aaacaaaatg    900
atcagcctga acatcgacga gggtatcatc ttcaacaagg tagttgaaga tttcgacttc    960
cgtgctgttg tcagcagcct gtccgagctg aaaggcattg agtacgaggg tcaatacatc   1020
gataaacagt acgaagagtt tattccgtct tctgcaccgc tgagccagga ccgcctgtgg   1080
caggcagttg agtccctgac gcagtccaac gaaactatcg tagcggaaca aggtaccctct   1140 ttcttcggtg cttctaccat ctttctgaag tccaactctc gctttatcgg tcagccgctg   1200
tggggttcta tcggttacac gttcccggct gcgctgggta ccagatcgc tgataaagag   1260 tctcgtcatc tgctgttcat cggtgatggt tccctgcagc tgactgtaca ggaactgggt   1320
ctgtctatcc gtgaaaaact gaacccgatt gtttttatca tcaataacga tggctacact   1380
gttgagcgtg aaattcatgg tccgactcag tcttacaacg atattccgat gtggaactac   1440
tctaaactgc cggaaaacctt cggtgcaact gaggatcgcg tcgtgagcaa gattgtgcgt   1500
```

```
actgagaacg agttcgtatc tgttatgaaa gaggcgcagg cagatgtgaa ccgcatgtac    1560
tggatcgaac tggttctgga aaagaggat gcaccgaaac tgctgaagaa aatgggtaaa    1620
ctgtttgcgg agcagaacaa gtaa                                         1644

<210> SEQ ID NO 42
<211> LENGTH: 1647
<212> TYPE: DNA
<213> ORGANISM: Lactococcus lactis
<220> FEATURE:
<221> NAME/KEY: CDS
<222> LOCATION: (1)..(1647)

<400> SEQUENCE: 42 atg tat aca gta gga gat tac cta tta gac cga tta cac gag tta gga      48
Met Tyr Thr Val Gly Asp Tyr Leu Leu Asp Arg Leu His Glu Leu Gly
1               5                  10                  15 att gaa gaa att ttt gga gtc cct gga gac tat aac tta caa ttt tta      96
Ile Glu Glu Ile Phe Gly Val Pro Gly Asp Tyr Asn Leu Gln Phe Leu
            20                  25                  30 gat caa att att tcc cac aag gat atg aaa tgg gtc gga aat gct aat     144
Asp Gln Ile Ile Ser His Lys Asp Met Lys Trp Val Gly Asn Ala Asn
        35                  40                  45 gaa tta aat gct tca tat atg gct gat ggc tat gct cgt act aaa aaa     192
Glu Leu Asn Ala Ser Tyr Met Ala Asp Gly Tyr Ala Arg Thr Lys Lys
    50                  55                  60 gct gcc gca ttt ctt aca acc ttt gga gta ggt gaa ttg agt gca gtt     240
Ala Ala Ala Phe Leu Thr Thr Phe Gly Val Gly Glu Leu Ser Ala Val
65                  70                  75                  80 aat gga tta gca gga agt tac gcc gaa aat tta cca gta gta gaa ata     288
Asn Gly Leu Ala Gly Ser Tyr Ala Glu Asn Leu Pro Val Val Glu Ile
                85                  90                  95 gtg gga tca cct aca tca aaa gtt caa aat gaa gga aaa ttt gtt cat     336
Val Gly Ser Pro Thr Ser Lys Val Gln Asn Glu Gly Lys Phe Val His
            100                 105                 110 cat acg ctg gct gac ggt gat ttt aaa cac ttt atg aaa atg cac gaa     384
His Thr Leu Ala Asp Gly Asp Phe Lys His Phe Met Lys Met His Glu
        115                 120                 125 cct gtt aca gca gct cga act tta ctg aca gca gaa aat gca acc gtt     432
Pro Val Thr Ala Ala Arg Thr Leu Leu Thr Ala Glu Asn Ala Thr Val
    130                 135                 140 gaa att gac cga gta ctt tct gca cta tta aaa gaa aga aaa cct gtc     480
Glu Ile Asp Arg Val Leu Ser Ala Leu Leu Lys Glu Arg Lys Pro Val
145                 150                 155                 160 tat atc aac tta cca gtt gat gtt gct gct gca aaa gca gag aaa ccc     528
Tyr Ile Asn Leu Pro Val Asp Val Ala Ala Ala Lys Ala Glu Lys Pro
                165                 170                 175 tca ctc cct ttg aaa aag gaa aac tca act tca aat aca agt gac caa     576
Ser Leu Pro Leu Lys Lys Glu Asn Ser Thr Ser Asn Thr Ser Asp Gln
            180                 185                 190 gaa att ttg aac aaa att caa gaa agc ttg aaa aat gcc aaa aaa cca     624
Glu Ile Leu Asn Lys Ile Gln Glu Ser Leu Lys Asn Ala Lys Lys Pro
        195                 200                 205 atc gtg att aca gga cat gaa ata att agt ttt ggc tta gaa aaa aca     672
Ile Val Ile Thr Gly His Glu Ile Ile Ser Phe Gly Leu Glu Lys Thr
    210                 215                 220 gtc act caa ttt att tca aag aca aaa cta cct att acg aca tta aac     720
Val Thr Gln Phe Ile Ser Lys Thr Lys Leu Pro Ile Thr Thr Leu Asn
225                 230                 235                 240 ttt ggt aaa agt tca gtt gat gaa gcc ctc cct tca ttt tta gga atc     768
```

```
                Phe Gly Lys Ser Ser Val Asp Glu Ala Leu Pro Ser Phe Leu Gly Ile
                                245                 250                 255 tat aat ggt aca ctc tca gag cct aat ctt aaa gaa ttc gtg gaa tca        816
Tyr Asn Gly Thr Leu Ser Glu Pro Asn Leu Lys Glu Phe Val Glu Ser
                260                 265                 270 gcc gac ttc atc ttg atg ctt gga gtt aaa ctc aca gac tct tca aca        864
Ala Asp Phe Ile Leu Met Leu Gly Val Lys Leu Thr Asp Ser Ser Thr
            275                 280                 285 gga gcc ttc act cat cat tta aat gaa aat aaa atg att tca ctg aat        912
Gly Ala Phe Thr His His Leu Asn Glu Asn Lys Met Ile Ser Leu Asn
        290                 295                 300 ata gat gaa gga aaa ata ttt aac gaa aga atc caa aat ttt gat ttt        960
Ile Asp Glu Gly Lys Ile Phe Asn Glu Arg Ile Gln Asn Phe Asp Phe
305                 310                 315                 320 gaa tcc ctc atc tcc tct ctc tta gac cta agc gaa ata gaa tac aaa       1008
Glu Ser Leu Ile Ser Ser Leu Leu Asp Leu Ser Glu Ile Glu Tyr Lys
                325                 330                 335 gga aaa tat atc gat aaa aag caa gaa gac ttt gtt cca tca aat gcg       1056
Gly Lys Tyr Ile Asp Lys Lys Gln Glu Asp Phe Val Pro Ser Asn Ala
            340                 345                 350 ctt tta tca caa gac cgc cta tgg caa gca gtt gaa aac cta act caa       1104
Leu Leu Ser Gln Asp Arg Leu Trp Gln Ala Val Glu Asn Leu Thr Gln
        355                 360                 365 agc aat gaa aca atc gtt gct gaa caa ggg aca tca ttc ttt ggc gct       1152
Ser Asn Glu Thr Ile Val Ala Glu Gln Gly Thr Ser Phe Phe Gly Ala
370                 375                 380 tca tca att ttc tta aaa tca aag agt cat ttt att ggt caa ccc tta       1200
Ser Ser Ile Phe Leu Lys Ser Lys Ser His Phe Ile Gly Gln Pro Leu
385                 390                 395                 400 tgg gga tca att gga tat aca ttc cca gca gca tta gga agc caa att       1248
Trp Gly Ser Ile Gly Tyr Thr Phe Pro Ala Ala Leu Gly Ser Gln Ile
                405                 410                 415 gca gat aaa gaa agc aga cac ctt tta ttt att ggt gat ggt tca ctt       1296
Ala Asp Lys Glu Ser Arg His Leu Leu Phe Ile Gly Asp Gly Ser Leu
            420                 425                 430 caa ctt aca gtg caa gaa tta gga tta gca atc aga gaa aaa att aat       1344
Gln Leu Thr Val Gln Glu Leu Gly Leu Ala Ile Arg Glu Lys Ile Asn
        435                 440                 445 cca att tgc ttt att atc aat aat gat ggt tat aca gtc gaa aga gaa       1392
Pro Ile Cys Phe Ile Ile Asn Asn Asp Gly Tyr Thr Val Glu Arg Glu
450                 455                 460 att cat gga cca aat caa agc tac aat gat att cca atg tgg aat tac       1440
Ile His Gly Pro Asn Gln Ser Tyr Asn Asp Ile Pro Met Trp Asn Tyr
465                 470                 475                 480 tca aaa tta cca gaa tcg ttt gga gca aca gaa gat cga gta gtc tca       1488
Ser Lys Leu Pro Glu Ser Phe Gly Ala Thr Glu Asp Arg Val Val Ser
                485                 490                 495 aaa atc gtt aga act gaa aat gaa ttt gtg tct gtc atg aaa gaa gct       1536
Lys Ile Val Arg Thr Glu Asn Glu Phe Val Ser Val Met Lys Glu Ala
            500                 505                 510 caa gca gat cca aat aga atg tac tgg att gag tta att ttg gca aaa       1584
Gln Ala Asp Pro Asn Arg Met Tyr Trp Ile Glu Leu Ile Leu Ala Lys
        515                 520                 525 gaa ggt gca cca aaa gta ctg aaa aaa atg ggc aaa cta ttt gct gaa       1632
Glu Gly Ala Pro Lys Val Leu Lys Lys Met Gly Lys Leu Phe Ala Glu
530                 535                 540 caa aat aaa tca taa                                                   1647
Gln Asn Lys Ser
545
```

```
<210> SEQ ID NO 43
<211> LENGTH: 548
<212> TYPE: PRT
<213> ORGANISM: Lactococcus lactis

<400> SEQUENCE: 43
```

| | | | | | | | | | | | | | | |
|---|---|---|---|---|---|---|---|---|---|---|---|---|---|---|
| Met | Tyr | Thr | Val | Gly | Asp | Tyr | Leu | Leu | Asp | Arg | Leu | His | Glu | Leu | Gly |
| 1 | | | | 5 | | | | | 10 | | | | | 15 | |
| Ile | Glu | Glu | Ile | Phe | Gly | Val | Pro | Gly | Asp | Tyr | Asn | Leu | Gln | Phe | Leu |
| | | | 20 | | | | | 25 | | | | | 30 | | |
| Asp | Gln | Ile | Ile | Ser | His | Lys | Asp | Met | Lys | Trp | Val | Gly | Asn | Ala | Asn |
| | | 35 | | | | | 40 | | | | | 45 | | | |
| Glu | Leu | Asn | Ala | Ser | Tyr | Met | Ala | Asp | Gly | Tyr | Ala | Arg | Thr | Lys | Lys |
| | 50 | | | | | 55 | | | | | 60 | | | | |
| Ala | Ala | Ala | Phe | Leu | Thr | Thr | Phe | Gly | Val | Gly | Glu | Leu | Ser | Ala | Val |
| 65 | | | | | 70 | | | | | 75 | | | | | 80 |
| Asn | Gly | Leu | Ala | Gly | Ser | Tyr | Ala | Glu | Asn | Leu | Pro | Val | Val | Glu | Ile |
| | | | | 85 | | | | | 90 | | | | | 95 | |
| Val | Gly | Ser | Pro | Thr | Ser | Lys | Val | Gln | Asn | Glu | Gly | Lys | Phe | Val | His |
| | | | 100 | | | | | 105 | | | | | 110 | | |
| His | Thr | Leu | Ala | Asp | Gly | Asp | Phe | Lys | His | Phe | Met | Lys | Met | His | Glu |
| | | 115 | | | | | 120 | | | | | 125 | | | |
| Pro | Val | Thr | Ala | Ala | Arg | Thr | Leu | Leu | Thr | Ala | Glu | Asn | Ala | Thr | Val |
| | 130 | | | | | 135 | | | | | 140 | | | | |
| Glu | Ile | Asp | Arg | Val | Leu | Ser | Ala | Leu | Leu | Lys | Glu | Arg | Lys | Pro | Val |
| 145 | | | | | 150 | | | | | 155 | | | | | 160 |
| Tyr | Ile | Asn | Leu | Pro | Val | Asp | Val | Ala | Ala | Ala | Lys | Ala | Glu | Lys | Pro |
| | | | | 165 | | | | | 170 | | | | | 175 | |
| Ser | Leu | Pro | Leu | Lys | Lys | Glu | Asn | Ser | Thr | Ser | Asn | Thr | Ser | Asp | Gln |
| | | | 180 | | | | | 185 | | | | | 190 | | |
| Glu | Ile | Leu | Asn | Lys | Ile | Gln | Glu | Ser | Leu | Lys | Asn | Ala | Lys | Lys | Pro |
| | | 195 | | | | | 200 | | | | | 205 | | | |
| Ile | Val | Ile | Thr | Gly | His | Glu | Ile | Ile | Ser | Phe | Gly | Leu | Glu | Lys | Thr |
| | 210 | | | | | 215 | | | | | 220 | | | | |
| Val | Thr | Gln | Phe | Ile | Ser | Lys | Thr | Lys | Leu | Pro | Ile | Thr | Thr | Leu | Asn |
| 225 | | | | | 230 | | | | | 235 | | | | | 240 |
| Phe | Gly | Lys | Ser | Ser | Val | Asp | Glu | Ala | Leu | Pro | Ser | Phe | Leu | Gly | Ile |
| | | | | 245 | | | | | 250 | | | | | 255 | |
| Tyr | Asn | Gly | Thr | Leu | Ser | Glu | Pro | Asn | Leu | Lys | Glu | Phe | Val | Glu | Ser |
| | | | 260 | | | | | 265 | | | | | 270 | | |
| Ala | Asp | Phe | Ile | Leu | Met | Leu | Gly | Val | Lys | Leu | Thr | Asp | Ser | Ser | Thr |
| | | 275 | | | | | 280 | | | | | 285 | | | |
| Gly | Ala | Phe | Thr | His | His | Leu | Asn | Glu | Asn | Lys | Met | Ile | Ser | Leu | Asn |
| | 290 | | | | | 295 | | | | | 300 | | | | |
| Ile | Asp | Glu | Gly | Lys | Ile | Phe | Asn | Glu | Arg | Ile | Gln | Asn | Phe | Asp | Phe |
| 305 | | | | | 310 | | | | | 315 | | | | | 320 |
| Glu | Ser | Leu | Ile | Ser | Ser | Leu | Asp | Leu | Ser | Glu | Ile | Glu | Tyr | Lys |
| | | | | 325 | | | | | 330 | | | | | 335 | |
| Gly | Lys | Tyr | Ile | Asp | Lys | Lys | Gln | Glu | Asp | Phe | Val | Pro | Ser | Asn | Ala |
| | | | 340 | | | | | 345 | | | | | 350 | | |
| Leu | Leu | Ser | Gln | Asp | Arg | Leu | Trp | Gln | Ala | Val | Glu | Asn | Leu | Thr | Gln |
| | | 355 | | | | | 360 | | | | | 365 | | | |
| Ser | Asn | Glu | Thr | Ile | Val | Ala | Glu | Gln | Gly | Thr | Ser | Phe | Phe | Gly | Ala |
| | 370 | | | | | 375 | | | | | 380 | | | | |

```
Ser Ser Ile Phe Leu Lys Ser Lys Ser His Phe Ile Gly Gln Pro Leu
385                 390                 395                 400

Trp Gly Ser Ile Gly Tyr Thr Phe Pro Ala Ala Leu Gly Ser Gln Ile
            405                 410                 415

Ala Asp Lys Glu Ser Arg His Leu Leu Phe Ile Gly Asp Gly Ser Leu
        420                 425                 430

Gln Leu Thr Val Gln Glu Leu Gly Leu Ala Ile Arg Glu Lys Ile Asn
            435                 440                 445

Pro Ile Cys Phe Ile Ile Asn Asn Asp Gly Tyr Thr Val Glu Arg Glu
        450                 455                 460

Ile His Gly Pro Asn Gln Ser Tyr Asn Asp Ile Pro Met Trp Asn Tyr
465                 470                 475                 480

Ser Lys Leu Pro Glu Ser Phe Gly Ala Thr Glu Asp Arg Val Val Ser
            485                 490                 495

Lys Ile Val Arg Thr Glu Asn Glu Phe Val Ser Val Met Lys Glu Ala
        500                 505                 510

Gln Ala Asp Pro Asn Arg Met Tyr Trp Ile Glu Leu Ile Leu Ala Lys
        515                 520                 525

Glu Gly Ala Pro Lys Val Leu Lys Lys Met Gly Lys Leu Phe Ala Glu
        530                 535                 540

Gln Asn Lys Ser
545
```

<210> SEQ ID NO 44
<211> LENGTH: 1647
<212> TYPE: DNA
<213> ORGANISM: Artificial
<220> FEATURE:
<223> OTHER INFORMATION: Lactococcus lactis -ketoisovalerate
      decarboxylase KivD codon optimised gene

<400> SEQUENCE: 44

```
atgtatactg ttggtgatta cctgctggat cgtctgcatg aactgggcat cgaggaaatt    60
ttcggcgtac ctggtgacta taacctgcag ttcctggatc agatcatttc ccacaaagat   120
atgaaatggg ttggtaacgc gaacgagctg aatgcaagct acatggctga cggttatgca   180
cgcaccaaga agctgcggc gttcctgact acttttggcg tcggcgagct gtctgcggta   240
aacggtctgg ccggctccta cgcggaaaac ctgccggtag tagaaatcgt cggttccccg   300
acctctaaag ttcagaacga gggtaaattc gtgcaccata ctctggccga tggtgacttc   360
aaacacttca tgaagatgca cgaaccggtc actgctgctc gtacgctgct gaccgcggaa   420
aatgcgactg tcgagattga tcgtgtactg agcgcactgc tgaaagaacg caagcctgta   480
tacatcaacc tgccggttga tgtcgcggcc gccaaagcgg aaaaaccatc tctgccgctg   540
aaaaaggaga acagcaccct aacaccagcg accaggaaa tcctgaacaa gatccaggag   600
tctctgaaga cgctaaaaa gccgatcgta atcaccggcc atgagattat ctctttcggt   660
ctggagaaaa ctgtcaccca gttcatcagc aaaaccaaac tgccgatcac caccctgaac   720
ttcggtaaat cctccgttga cgaagcgctg ccgtcctttc tgggtatttta aacggcact   780
ctgtctgagc cgaacctgaa agagttcgtg gagtctgcgg attttatcct gatgctgggc   840
gtgaaactga cggattcctc caccggtgca ttcacccacc acctgaatga aataaaatg   900
atctctctga acattgatga gggcaaaaat ttcaacgagc gtattcagaa cttcgatttc   960
gaatccctga tctcctccct gctggatctg tccgagattg aatataaagg caaatacatt  1020
```

-continued

| | |
|---|---|
| gataagaagc aagaggactt cgtaccgtct aacgcgctgc tgagccagga ccgtctgtgg | 1080 |
| caagctgtgg aaaacctgac ccagtccaac gaaaccatcg tggcggaaca gggtaccctcc | 1140 |
| ttcttcggtg ctagctctat cttcctgaaa tctaaaagcc acttcatcgg tcagccactg | 1200 |
| tggggctcta ttggctacac cttcccggca gcgctgggtt cccaaatcgc agacaaagaa | 1260 |
| tcccgccacc tgctgttcat tggtgacggc tctctgcaac tgaccgtaca ggagctgggt | 1320 |
| ctggcgattc gtgagaaaat caacccgatt tgtttcatca tcaacaacga tggctacact | 1380 |
| gttgagcgtg agatccacgg cccgaaccag tcctacaacg acattccgat gtggaactac | 1440 |
| tctaaactgc cggaatcctt cggtgcgact gaagaccgtg tcgtaagcaa gatcgtccgt | 1500 |
| accgaaaacg aattcgtgtc tgtcatgaaa gaagcacagg cggacccgaa ccgcatgtac | 1560 |
| tggatcgagc tgattctggc taaagagggc gcgccaaaag tactgaaaaa gatgggtaaa | 1620 |
| ctgttcgcag aacagaacaa atcctaa | 1647 |

<210> SEQ ID NO 45
<211> LENGTH: 3696
<212> TYPE: DNA
<213> ORGANISM: Mycobacterium tuberculosis
<220> FEATURE:
<221> NAME/KEY: CDS
<222> LOCATION: (1)..(3696)

<400> SEQUENCE: 45

| | |
|---|---|
| gtg gcc aac ata agt tca cca ttc ggg caa aac gaa tgg ctg gtc gaa<br>Val Ala Asn Ile Ser Ser Pro Phe Gly Gln Asn Glu Trp Leu Val Glu<br>1                  5                10             15 | 48 |
| gag atg tac cgc aag ttc cgc gac gac ccc tcc tcg gtc gat ccc agc<br>Glu Met Tyr Arg Lys Phe Arg Asp Asp Pro Ser Ser Val Asp Pro Ser<br>               20                25             30 | 96 |
| tgg cac gag ttc ctg gtt gac tac agc ccc gaa ccc acc tcc caa cca<br>Trp His Glu Phe Leu Val Asp Tyr Ser Pro Glu Pro Thr Ser Gln Pro<br>        35                40             45 | 144 |
| gct gcc gaa cca acc cgg gtt acc tcg cca ctc gtt gcc gag cgg gcc<br>Ala Ala Glu Pro Thr Arg Val Thr Ser Pro Leu Val Ala Glu Arg Ala<br>50                55                60 | 192 |
| gct gcg gcc gcc ccg cag gca ccc ccc aag ccg gcc gac acc gcg gcc<br>Ala Ala Ala Ala Pro Gln Ala Pro Pro Lys Pro Ala Asp Thr Ala Ala<br>65                70                75             80 | 240 |
| gcg ggc aac ggc gtg gtc gcc gca ctg gcc gcc aaa act gcc gtt ccc<br>Ala Gly Asn Gly Val Val Ala Ala Leu Ala Ala Lys Thr Ala Val Pro<br>               85                90             95 | 288 |
| ccg cca gcc gaa ggt gac gag gta gcc gtg ctg cgc ggc gcc gcc gcg<br>Pro Pro Ala Glu Gly Asp Glu Val Ala Val Leu Arg Gly Ala Ala Ala<br>               100             105             110 | 336 |
| gcc gtc gtc aag aac atg tcc gcg tcg ttg gag gtg ccg acg gcg acc<br>Ala Val Val Lys Asn Met Ser Ala Ser Leu Glu Val Pro Thr Ala Thr<br>        115               120             125 | 384 |
| agc gtc cgg gcg gtc ccg gcc aag cta ctg atc gac aac cgg atc gtc<br>Ser Val Arg Ala Val Pro Ala Lys Leu Leu Ile Asp Asn Arg Ile Val<br>130              135                140 | 432 |
| atc aac aac cag ttg aag cgg acc cgc ggc ggc aag atc tcg ttc acg<br>Ile Asn Asn Gln Leu Lys Arg Thr Arg Gly Gly Lys Ile Ser Phe Thr<br>145                150                155            160 | 480 |
| cat ttg ctg ggc tac gcc ctg gtg cag gcg gtg aag aaa ttc ccg aac<br>His Leu Leu Gly Tyr Ala Leu Val Gln Ala Val Lys Lys Phe Pro Asn<br>               165             170             175 | 528 |
| atg aac cgg cac tac acc gaa gtc gac ggc aag ccc acc gcg gtc acg<br>Met Asn Arg His Tyr Thr Glu Val Asp Gly Lys Pro Thr Ala Val Thr | 576 |

```
                 180                      185                      190
ccg gcg cac acc aat ctc ggc ctg gcg atc gac ctg caa ggc aag gac      624
Pro Ala His Thr Asn Leu Gly Leu Ala Ile Asp Leu Gln Gly Lys Asp
            195                      200                      205 ggg aag cgt tcc ctg gtg gtg gcc ggc atc aag cgg tgc gag acc atg      672
Gly Lys Arg Ser Leu Val Val Ala Gly Ile Lys Arg Cys Glu Thr Met
210                      215                      220 cga ttc gcg cag ttc gtc acg gcc tac gaa gac atc gta cgc cgg gcc      720
Arg Phe Ala Gln Phe Val Thr Ala Tyr Glu Asp Ile Val Arg Arg Ala
225                      230                      235                      240 cgc gac ggc aag ctg acc act gaa gac ttt gcc ggc gtg acg att tcg      768
Arg Asp Gly Lys Leu Thr Thr Glu Asp Phe Ala Gly Val Thr Ile Ser
            245                      250                      255 ctg acc aat ccc gga acc atc ggc acc gtg cat tcg gtg ccg cgg ctg      816
Leu Thr Asn Pro Gly Thr Ile Gly Thr Val His Ser Val Pro Arg Leu
            260                      265                      270 atg ccc ggc cag ggc gcc atc atc ggc gtg ggc gcc atg gaa tac ccc      864
Met Pro Gly Gln Gly Ala Ile Ile Gly Val Gly Ala Met Glu Tyr Pro
            275                      280                      285 gcc gag ttt caa ggc gcc agc gag gaa cgc atc gcc gag ctg ggc atc      912
Ala Glu Phe Gln Gly Ala Ser Glu Glu Arg Ile Ala Glu Leu Gly Ile
            290                      295                      300 ggc aaa ttg atc act ttg acc tcc acc tac gac cac cgc atc atc cag      960
Gly Lys Leu Ile Thr Leu Thr Ser Thr Tyr Asp His Arg Ile Ile Gln
305                      310                      315                      320 ggc gcg gaa tcg ggc gac ttc ctg cgc acc atc cac gag ttg ctc ctc     1008
Gly Ala Glu Ser Gly Asp Phe Leu Arg Thr Ile His Glu Leu Leu Leu
                325                      330                      335 tcg gat ggc ttc tgg gac gag gtc ttc cgc gaa ctg agc atc cca tat     1056
Ser Asp Gly Phe Trp Asp Glu Val Phe Arg Glu Leu Ser Ile Pro Tyr
            340                      345                      350 ctg ccg gtg cgc tgg agc acc gac aac ccc gac tcg atc gtc gac aag     1104
Leu Pro Val Arg Trp Ser Thr Asp Asn Pro Asp Ser Ile Val Asp Lys
            355                      360                      365 aac gct cgc gtc atg aac ttg atc gcg gcc tac cgc aac cgc ggc cat     1152
Asn Ala Arg Val Met Asn Leu Ile Ala Ala Tyr Arg Asn Arg Gly His
            370                      375                      380 ctg atg gcc gat acc gac ccg ctg cgg ttg gac aaa gct cgg ttc cgc     1200
Leu Met Ala Asp Thr Asp Pro Leu Arg Leu Asp Lys Ala Arg Phe Arg
385                      390                      395                      400 agt cac ccc gac ctc gaa gtg ctg acc cac ggc ctg acg ctg tgg gat     1248
Ser His Pro Asp Leu Glu Val Leu Thr His Gly Leu Thr Leu Trp Asp
                405                      410                      415 ctc gat cgg gtg ttc aag gtc gac ggc ttt gcc ggt gcg cag tac aag     1296
Leu Asp Arg Val Phe Lys Val Asp Gly Phe Ala Gly Ala Gln Tyr Lys
            420                      425                      430 aaa ctg cgc gac gtg ctg ggc ttg ctg cgc gat gcc tac tgc cgc cac     1344
Lys Leu Arg Asp Val Leu Gly Leu Leu Arg Asp Ala Tyr Cys Arg His
            435                      440                      445 atc ggc gtg gag tac gcc cat atc ctc gac ccc gaa caa aag gag tgg     1392
Ile Gly Val Glu Tyr Ala His Ile Leu Asp Pro Glu Gln Lys Glu Trp
            450                      455                      460 ctc gaa caa cgg gtc gag acc aag cac gtc aaa ccc act gtg gcc caa     1440
Leu Glu Gln Arg Val Glu Thr Lys His Val Lys Pro Thr Val Ala Gln
465                      470                      475                      480 cag aaa tac atc ctc agc aag ctc aac gcc gcc gag gcc ttt gaa acg     1488
Gln Lys Tyr Ile Leu Ser Lys Leu Asn Ala Ala Glu Ala Phe Glu Thr
                485                      490                      495 ttc cta cag acc aag tac gtc ggc cag aag cgg ttc tcg ctg gaa ggc     1536
```

-continued

```
                Phe Leu Gln Thr Lys Tyr Val Gly Gln Lys Arg Phe Ser Leu Glu Gly
                                500                 505                 510 gcc gaa agc gtg atc ccg atg atg gac gcg gcg atc gac cag tgc gct              1584
Ala Glu Ser Val Ile Pro Met Met Asp Ala Ala Ile Asp Gln Cys Ala
        515                 520                 525 gag cac ggc ctc gac gag gtg gtc atc ggg atg ccg cac cgg ggc cgg              1632
Glu His Gly Leu Asp Glu Val Val Ile Gly Met Pro His Arg Gly Arg
530                 535                 540 ctc aac gtg ctg gcc aac atc gtc ggc aag ccg tac tcg cag atc ttc              1680
Leu Asn Val Leu Ala Asn Ile Val Gly Lys Pro Tyr Ser Gln Ile Phe
545                 550                 555                 560 acc gag ttc gag ggc aac ctg aat ccg tcg cag gcg cac ggc tcc ggt              1728
Thr Glu Phe Glu Gly Asn Leu Asn Pro Ser Gln Ala His Gly Ser Gly
                565                 570                 575 gac gtc aag tac cac ctg ggc gcc acc ggg ctg tac ctg cag atg ttc              1776
Asp Val Lys Tyr His Leu Gly Ala Thr Gly Leu Tyr Leu Gln Met Phe
            580                 585                 590 ggc gac aac gac att cag gtg tcg ctg acc gcc aac ccg tcg cat ctg              1824
Gly Asp Asn Asp Ile Gln Val Ser Leu Thr Ala Asn Pro Ser His Leu
        595                 600                 605 gag gcc gtc gac ccg gtg ctg gag gga ttg gtg cgg gcc aag cag gat              1872
Glu Ala Val Asp Pro Val Leu Glu Gly Leu Val Arg Ala Lys Gln Asp
610                 615                 620 ctg ctc gac cac gga agc atc gac agc gac ggc caa cgg gcg ttc tcg              1920
Leu Leu Asp His Gly Ser Ile Asp Ser Asp Gly Gln Arg Ala Phe Ser
625                 630                 635                 640 gtg gtg ccg ctg atg ttg cat ggc gat gcc gcg ttc gcc ggt cag ggt              1968
Val Val Pro Leu Met Leu His Gly Asp Ala Ala Phe Ala Gly Gln Gly
                645                 650                 655 gtg gtc gcc gag acg ctg aac ctg gcg aat ctg ccg ggc tac cgc gtc              2016
Val Val Ala Glu Thr Leu Asn Leu Ala Asn Leu Pro Gly Tyr Arg Val
            660                 665                 670 ggc ggc acc atc cac atc atc gtc aac aac cag atc ggc ttc acc acc              2064
Gly Gly Thr Ile His Ile Ile Val Asn Asn Gln Ile Gly Phe Thr Thr
        675                 680                 685 gcg ccc gag tat tcc agg tcc agc gag tac tgc acc gac gtc gca aag              2112
Ala Pro Glu Tyr Ser Arg Ser Ser Glu Tyr Cys Thr Asp Val Ala Lys
690                 695                 700 atg atc ggg gca ccg atc ttt cac gtc aac ggc gac gac ccg gag gcg              2160
Met Ile Gly Ala Pro Ile Phe His Val Asn Gly Asp Asp Pro Glu Ala
705                 710                 715                 720 tgt gtc tgg gtg gcg cgg ttg gcg gtg gac ttc cga caa cgg ttc aag              2208
Cys Val Trp Val Ala Arg Leu Ala Val Asp Phe Arg Gln Arg Phe Lys
                725                 730                 735 aag gac gtc gtc atc gac atg ctg tgc tac cgc cgc cgc ggg cac aac              2256
Lys Asp Val Val Ile Asp Met Leu Cys Tyr Arg Arg Arg Gly His Asn
            740                 745                 750 gag ggt gac gac ccg tcg atg acc aac ccc tac gtg tac gac gtc gtc              2304
Glu Gly Asp Asp Pro Ser Met Thr Asn Pro Tyr Val Tyr Asp Val Val
        755                 760                 765 gac acc aag cgc ggg gcc cgc aaa agc tac acc gaa gcc ctg atc gga              2352
Asp Thr Lys Arg Gly Ala Arg Lys Ser Tyr Thr Glu Ala Leu Ile Gly
770                 775                 780 cgt ggc gac atc tcg atg aag gag gcc gag gac gcg ctg cgc gac tac              2400
Arg Gly Asp Ile Ser Met Lys Glu Ala Glu Asp Ala Leu Arg Asp Tyr
785                 790                 795                 800 cag ggc cag ctg gaa cgg gtg ttc aac gaa gtg cgc gag ctg gag aag              2448
Gln Gly Gln Leu Glu Arg Val Phe Asn Glu Val Arg Glu Leu Glu Lys
                805                 810                 815
```

```
cac ggt gtg cag ccg agc gag tcg gtc gag tcc gac cag atg att ccc     2496
His Gly Val Gln Pro Ser Glu Ser Val Glu Ser Asp Gln Met Ile Pro
            820                 825                 830 gcg ggg ctg gcc act gcg gtg gac aag tcg ctg ctg gcc cgg atc ggc     2544
Ala Gly Leu Ala Thr Ala Val Asp Lys Ser Leu Leu Ala Arg Ile Gly
            835                 840                 845 gat gcg ttc ctc gcc ttg ccg aac ggc ttc acc gcg cac ccg cga gtc     2592
Asp Ala Phe Leu Ala Leu Pro Asn Gly Phe Thr Ala His Pro Arg Val
            850                 855                 860 caa ccg gtg ctg gag aag cgc cgg gag atg gcc tat gaa ggc aag atc     2640
Gln Pro Val Leu Glu Lys Arg Arg Glu Met Ala Tyr Glu Gly Lys Ile
865                 870                 875                 880 gac tgg gcc ttt ggc gag ctg ctg gcg ctg ggc tcg ctg gtg gcc gaa     2688
Asp Trp Ala Phe Gly Glu Leu Leu Ala Leu Gly Ser Leu Val Ala Glu
                885                 890                 895 ggc aag ctg gtg cgc ttg tcg ggg cag gac agc cgc cgc ggc acc ttc     2736
Gly Lys Leu Val Arg Leu Ser Gly Gln Asp Ser Arg Arg Gly Thr Phe
                900                 905                 910 tcc cag cgg cat tcg gtt ctc atc gac cgc cac act ggc gag gag ttc     2784
Ser Gln Arg His Ser Val Leu Ile Asp Arg His Thr Gly Glu Glu Phe
            915                 920                 925 aca cca ctg cag ctg ctg gcg acc aac tcc gac ggc agc ccg acc ggc     2832
Thr Pro Leu Gln Leu Leu Ala Thr Asn Ser Asp Gly Ser Pro Thr Gly
930                 935                 940 gga aag ttc ctg gtc tac gac tcg cca ctg tcg gag tac gcc gcc gtc     2880
Gly Lys Phe Leu Val Tyr Asp Ser Pro Leu Ser Glu Tyr Ala Ala Val
945                 950                 955                 960 ggc ttc gag tac ggc tac act gtg ggc aat ccg gac gcc gtg gtg ctc     2928
Gly Phe Glu Tyr Gly Tyr Thr Val Gly Asn Pro Asp Ala Val Val Leu
                965                 970                 975 tgg gag gcg cag ttc ggc gac ttc gtc aac ggc gcg cag tcg atc atc     2976
Trp Glu Ala Gln Phe Gly Asp Phe Val Asn Gly Ala Gln Ser Ile Ile
            980                 985                 990 gac gag ttc atc agc tcc ggt gag gcc aag tgg ggc caa ttg tcc aac     3024
Asp Glu Phe Ile Ser Ser Gly Glu Ala Lys Trp Gly Gln Leu Ser Asn
            995                1000                1005 gtc gtg ctg ctg tta ccg cac  ggg cac gag ggg cag  gga ccc gac       3069
Val Val Leu Leu Leu Pro His  Gly His Glu Gly Gln  Gly Pro Asp
        1010               1015                 1020 cac act tct gcc cgg atc gaa  cgc ttc ttg cag ttg  tgg gcg aa        3114
His Thr Ser Ala Arg Ile Glu  Arg Phe Leu Gln Leu  Trp Ala Glu
        1025               1030                 1035 ggt tcg atg acc atc gcg atg  ccg tcg act ccg tcg  aac tac ttc       3159
Gly Ser Met Thr Ile Ala Met  Pro Ser Thr Pro Ser  Asn Tyr Phe
        1040               1045                 1050 cac ctg cta cgc cgg cat gcc  ctg gac ggc atc caa  cgc ccg ctg       3204
His Leu Leu Arg Arg His Ala  Leu Asp Gly Ile Gln  Arg Pro Leu
        1055               1060                 1065 atc gtg ttc acg ccc aag tcg  atg ttg cgt cac aag  gcc gcc gtc       3249
Ile Val Phe Thr Pro Lys Ser  Met Leu Arg His Lys  Ala Ala Val
        1070               1075                 1080 agc gaa atc aag gac ttc acc  gag atc aag ttc cgc  tca gtg ctg       3294
Ser Glu Ile Lys Asp Phe Thr  Glu Ile Lys Phe Arg  Ser Val Leu
        1085               1090                 1095 gag gaa ccc acc tat gag gac  ggc atc gga gac cgc  aac aag gtc       3339
Glu Glu Pro Thr Tyr Glu Asp  Gly Ile Gly Asp Arg  Asn Lys Val
        1100               1105                 1110 agc cgg atc ctg ctg acc agt  ggc aag ctg tat tac  gag ctg gcc       3384
Ser Arg Ile Leu Leu Thr Ser  Gly Lys Leu Tyr Tyr  Glu Leu Ala
        1115               1120                 1125
```

```
gcc cgc aag gcc aag gac aac cgc aat gac ctc gcg atc gtg cgg     3429
Ala Arg Lys Ala Lys Asp Asn Arg Asn Asp Leu Ala Ile Val Arg
    1130            1135                1140 ctt gaa cag ctc gcc ccg ctg ccc agg cgt cga ctg cgt gaa acg     3474
Leu Glu Gln Leu Ala Pro Leu Pro Arg Arg Leu Arg Glu Thr
1145            1150                1155 ctg gac cgc tac gag aac gtc aag gag ttc ttc tgg gtc caa gag     3519
Leu Asp Arg Tyr Glu Asn Val Lys Glu Phe Phe Trp Val Gln Glu
1160            1165                1170 gaa ccg gcc aac cag ggt gcg tgg ccg cga ttc ggg ctc gaa cta     3564
Glu Pro Ala Asn Gln Gly Ala Trp Pro Arg Phe Gly Leu Glu Leu
    1175            1180                1185 ccc gag ctg ctg cct gac aag ttg gcc ggg atc aag cga atc tcg     3609
Pro Glu Leu Leu Pro Asp Lys Leu Ala Gly Ile Lys Arg Ile Ser
1190            1195                1200 cgc cgg gcg atg tca gcc ccg tcg tca ggc tcg tcg aag gtg cac     3654
Arg Arg Ala Met Ser Ala Pro Ser Ser Gly Ser Ser Lys Val His
1205            1210                1215 gcc gtc gaa cag cag gag atc ctc gac gag gcg ttc ggc tga         3696
Ala Val Glu Gln Gln Glu Ile Leu Asp Glu Ala Phe Gly
1220            1225                1230

<210> SEQ ID NO 46
<211> LENGTH: 1231
<212> TYPE: PRT
<213> ORGANISM: Mycobacterium tuberculosis

<400> SEQUENCE: 46

Val Ala Asn Ile Ser Ser Pro Phe Gly Gln Asn Glu Trp Leu Val Glu
1               5                   10                  15

Glu Met Tyr Arg Lys Phe Arg Asp Asp Pro Ser Ser Val Asp Pro Ser
                20                  25                  30

Trp His Glu Phe Leu Val Asp Tyr Ser Pro Glu Pro Thr Ser Gln Pro
            35                  40                  45

Ala Ala Glu Pro Thr Arg Val Thr Ser Pro Leu Val Ala Glu Arg Ala
        50                  55                  60

Ala Ala Ala Ala Pro Gln Ala Pro Lys Pro Ala Asp Thr Ala Ala
65                  70                  75                  80

Ala Gly Asn Gly Val Val Ala Ala Leu Ala Ala Lys Thr Ala Val Pro
                85                  90                  95

Pro Pro Ala Glu Gly Asp Glu Val Ala Val Leu Arg Gly Ala Ala Ala
            100                 105                 110

Ala Val Val Lys Asn Met Ser Ala Ser Leu Glu Val Pro Thr Ala Thr
        115                 120                 125

Ser Val Arg Ala Val Pro Ala Lys Leu Leu Ile Asp Asn Arg Ile Val
    130                 135                 140

Ile Asn Asn Gln Leu Lys Arg Thr Arg Gly Gly Lys Ile Ser Phe Thr
145                 150                 155                 160

His Leu Leu Gly Tyr Ala Leu Val Gln Ala Val Lys Lys Phe Pro Asn
                165                 170                 175

Met Asn Arg His Tyr Thr Glu Val Asp Gly Lys Pro Thr Ala Val Thr
            180                 185                 190

Pro Ala His Thr Asn Leu Gly Leu Ala Ile Asp Leu Gln Gly Lys Asp
        195                 200                 205

Gly Lys Arg Ser Leu Val Val Ala Gly Ile Lys Arg Cys Glu Thr Met
    210                 215                 220
```

```
Arg Phe Ala Gln Phe Val Thr Ala Tyr Glu Asp Ile Val Arg Arg Ala
225                 230                 235                 240

Arg Asp Gly Lys Leu Thr Thr Glu Asp Phe Ala Gly Val Thr Ile Ser
            245                 250                 255

Leu Thr Asn Pro Gly Thr Ile Gly Thr Val His Ser Val Pro Arg Leu
        260                 265                 270

Met Pro Gly Gln Gly Ala Ile Ile Gly Val Gly Ala Met Glu Tyr Pro
    275                 280                 285

Ala Glu Phe Gln Gly Ala Ser Glu Glu Arg Ile Ala Glu Leu Gly Ile
290                 295                 300

Gly Lys Leu Ile Thr Leu Thr Ser Thr Tyr Asp His Arg Ile Ile Gln
305                 310                 315                 320

Gly Ala Glu Ser Gly Asp Phe Leu Arg Thr Ile His Glu Leu Leu Leu
            325                 330                 335

Ser Asp Gly Phe Trp Asp Glu Val Phe Arg Glu Leu Ser Ile Pro Tyr
        340                 345                 350

Leu Pro Val Arg Trp Ser Thr Asp Asn Pro Asp Ser Ile Val Asp Lys
    355                 360                 365

Asn Ala Arg Val Met Asn Leu Ile Ala Ala Tyr Arg Asn Arg Gly His
370                 375                 380

Leu Met Ala Asp Thr Asp Pro Leu Arg Leu Asp Lys Ala Arg Phe Arg
385                 390                 395                 400

Ser His Pro Asp Leu Glu Val Leu Thr His Gly Leu Thr Leu Trp Asp
            405                 410                 415

Leu Asp Arg Val Phe Lys Val Asp Gly Phe Ala Gly Ala Gln Tyr Lys
        420                 425                 430

Lys Leu Arg Asp Val Leu Gly Leu Leu Arg Asp Ala Tyr Cys Arg His
    435                 440                 445

Ile Gly Val Glu Tyr Ala His Ile Leu Asp Pro Glu Gln Lys Glu Trp
450                 455                 460

Leu Glu Gln Arg Val Glu Thr Lys His Val Lys Pro Thr Val Ala Gln
465                 470                 475                 480

Gln Lys Tyr Ile Leu Ser Lys Leu Asn Ala Ala Glu Ala Phe Glu Thr
            485                 490                 495

Phe Leu Gln Thr Lys Tyr Val Gly Gln Lys Arg Phe Ser Leu Glu Gly
        500                 505                 510

Ala Glu Ser Val Ile Pro Met Met Asp Ala Ala Ile Asp Gln Cys Ala
    515                 520                 525

Glu His Gly Leu Asp Glu Val Val Ile Gly Met Pro His Arg Gly Arg
530                 535                 540

Leu Asn Val Leu Ala Asn Ile Val Gly Lys Pro Tyr Ser Gln Ile Phe
545                 550                 555                 560

Thr Glu Phe Glu Gly Asn Leu Asn Pro Ser Gln Ala His Gly Ser Gly
            565                 570                 575

Asp Val Lys Tyr His Leu Gly Ala Thr Gly Leu Tyr Leu Gln Met Phe
        580                 585                 590

Gly Asp Asn Asp Ile Gln Val Ser Leu Thr Ala Asn Pro Ser His Leu
    595                 600                 605

Glu Ala Val Asp Pro Val Leu Glu Gly Leu Val Arg Ala Lys Gln Asp
610                 615                 620

Leu Leu Asp His Gly Ser Ile Asp Ser Asp Gly Gln Arg Ala Phe Ser
625                 630                 635                 640

Val Val Pro Leu Met Leu His Gly Asp Ala Ala Phe Ala Gly Gln Gly
```

-continued

```
                645                 650                 655
Val Val Ala Glu Thr Leu Asn Leu Ala Asn Leu Pro Gly Tyr Arg Val
            660                 665                 670
Gly Gly Thr Ile His Ile Ile Val Asn Asn Gln Ile Gly Phe Thr Thr
            675                 680                 685
Ala Pro Glu Tyr Ser Arg Ser Ser Glu Tyr Cys Thr Asp Val Ala Lys
            690                 695                 700
Met Ile Gly Ala Pro Ile Phe His Val Asn Gly Asp Asp Pro Glu Ala
705                 710                 715                 720
Cys Val Trp Val Ala Arg Leu Ala Val Asp Phe Arg Gln Arg Phe Lys
            725                 730                 735
Lys Asp Val Val Ile Asp Met Leu Cys Tyr Arg Arg Arg Gly His Asn
            740                 745                 750
Glu Gly Asp Asp Pro Ser Met Thr Asn Pro Tyr Val Tyr Asp Val Val
            755                 760                 765
Asp Thr Lys Arg Gly Ala Arg Lys Ser Tyr Thr Glu Ala Leu Ile Gly
            770                 775                 780
Arg Gly Asp Ile Ser Met Lys Glu Ala Glu Asp Ala Leu Arg Asp Tyr
785                 790                 795                 800
Gln Gly Gln Leu Glu Arg Val Phe Asn Glu Val Arg Glu Leu Glu Lys
            805                 810                 815
His Gly Val Gln Pro Ser Glu Ser Val Glu Ser Asp Gln Met Ile Pro
            820                 825                 830
Ala Gly Leu Ala Thr Ala Val Asp Lys Ser Leu Leu Ala Arg Ile Gly
            835                 840                 845
Asp Ala Phe Leu Ala Leu Pro Asn Gly Phe Thr Ala His Pro Arg Val
850                 855                 860
Gln Pro Val Leu Glu Lys Arg Arg Glu Met Ala Tyr Glu Gly Lys Ile
865                 870                 875                 880
Asp Trp Ala Phe Gly Glu Leu Leu Ala Leu Gly Ser Leu Val Ala Glu
            885                 890                 895
Gly Lys Leu Val Arg Leu Ser Gly Gln Asp Ser Arg Arg Gly Thr Phe
            900                 905                 910
Ser Gln Arg His Ser Val Leu Ile Asp Arg His Thr Gly Glu Glu Phe
            915                 920                 925
Thr Pro Leu Gln Leu Leu Ala Thr Asn Ser Asp Gly Ser Pro Thr Gly
            930                 935                 940
Gly Lys Phe Leu Val Tyr Asp Ser Pro Leu Ser Glu Tyr Ala Ala Val
945                 950                 955                 960
Gly Phe Glu Tyr Gly Tyr Thr Val Gly Asn Pro Asp Ala Val Val Leu
            965                 970                 975
Trp Glu Ala Gln Phe Gly Asp Phe Val Asn Gly Ala Gln Ser Ile Ile
            980                 985                 990
Asp Glu Phe Ile Ser Ser Gly Glu Ala Lys Trp Gly Gln Leu Ser Asn
            995                 1000                1005
Val Val Leu Leu Leu Pro His Gly His Glu Gly Gln Gly Pro Asp
            1010                1015                1020
His Thr Ser Ala Arg Ile Glu Arg Phe Leu Gln Leu Trp Ala Glu
            1025                1030                1035
Gly Ser Met Thr Ile Ala Met Pro Ser Thr Pro Ser Asn Tyr Phe
            1040                1045                1050
His Leu Leu Arg Arg His Ala Leu Asp Gly Ile Gln Arg Pro Leu
            1055                1060                1065
```

```
Ile Val  Phe Thr Pro Lys Ser  Met Leu Arg His Lys  Ala Ala Val
    1070                 1075                 1080

Ser Glu  Ile Lys Asp Phe Thr  Glu Ile Lys Phe Arg  Ser Val Leu
    1085                 1090                 1095

Glu Glu  Pro Thr Tyr Glu Asp  Gly Ile Gly Asp Arg  Asn Lys Val
    1100                 1105                 1110

Ser Arg  Ile Leu Leu Thr Ser  Gly Lys Leu Tyr Tyr  Glu Leu Ala
    1115                 1120                 1125

Ala Arg  Lys Ala Lys Asp Asn  Arg Asn Asp Leu Ala  Ile Val Arg
    1130                 1135                 1140

Leu Glu  Gln Leu Ala Pro Leu  Pro Arg Arg Arg Leu  Arg Glu Thr
    1145                 1150                 1155

Leu Asp  Arg Tyr Glu Asn Val  Lys Glu Phe Phe Trp  Val Gln Glu
    1160                 1165                 1170

Glu Pro  Ala Asn Gln Gly Ala  Trp Pro Arg Phe Gly  Leu Glu Leu
    1175                 1180                 1185

Pro Glu  Leu Leu Pro Asp Lys  Leu Ala Gly Ile Lys  Arg Ile Ser
    1190                 1195                 1200

Arg Arg  Ala Met Ser Ala Pro  Ser Ser Gly Ser Ser  Lys Val His
    1205                 1210                 1215

Ala Val  Glu Gln Gln Glu Ile  Leu Asp Glu Ala Phe  Gly
    1220                 1225                 1230

<210> SEQ ID NO 47
<211> LENGTH: 3696
<212> TYPE: DNA
<213> ORGANISM: Artificial
<220> FEATURE:
<223> OTHER INFORMATION: Mycobacterium tuberculosis  -ketoglutarate
      decarboxylase Kgd codon optimised gene

<400> SEQUENCE: 47
atggctaata tctcctctcc gtttggtcag aatgaatggc tggtagaaga aatgtaccgt     60
aaattccgcg atgacccgtc ctctgtggac ccgtcctggc atgaattcct ggtagactac    120
agcccggagc cgaccagcca accggcagcg gaaccaaccc gcgttacttc tccgctggta    180
gcggaacgtg cagctgctgc cgcgcctcag gcgccgccta aaccggcgga tactgccgca    240
gccggtaacg gtgtggtggc cgcactggct gctaagactg cggttccgcc gccagcagaa    300
ggcgatgaag ttgcagtcct gcgcggtgcg gcggctgcag tggtgaaaaa catgagcgcg    360
tccctggagg taccgaccgc cacgagcgtg cgcgcggtcc ctgctaaact gctgattgat    420
aaccgtattg tgatcaacaa ccagctgaaa cgtacccgtg gtggcaagat ctccttcact    480
catctgctgg gttatgcact ggtacaagcg gttaagaaat tccctaacat gaaccgtcat    540
tacactgagg tcgacggtaa accgacggct gttactccgg cacacacgaa cctgggcctg    600
gcgatcgacc tgcaaggtaa agatggtaag cgctccctgg tagttgcggg tattaaacgt    660
tgcgaaacca tgcgtttcgc acaattcgta accgcctacg aggacattgt ccgccgtgct    720
cgtgatggca aactgaccac cgaagatttt gcgggcgtta ctattagcct gaccaaccca    780
ggcaccatcg gcaccgtgca cagcgtacct cgtctgatgc cgggccaagg tgcgattatc    840
ggtgtgggtg ccatggagta cccggcagaa tttcagggtg cttctgaaga gcgcatcgcc    900
gagctgggta ttggtaaact gatcaccctg acttctacct atgaccaccg catcattcag    960
ggcgcagaat ccggtgactt cctgcgcact attcacgaac tgctgctgtc cgacggtttc   1020
```

| | |
|---|---|
| tgggatgaag ttttcgtga actgagcatc ccatatctgc cagttcgctg gtccaccgac | 1080 |
| aatccggact ctatcgttga caaaaacgct cgcgtaatga acctgatcgc tgcttatcgt | 1140 |
| aatcgtggtc acctgatggc tgatacggat ccgctgcgcc tggataaagc tcgtttccgt | 1200 |
| tcccacccgg acctggaagt gctgacccat ggtctgactc tgtgggatct ggaccgcgtg | 1260 |
| ttcaaagtag atggtttcgc gggtgctcag tacaagaagc tgccgtgacgt gctgggtctg | 1320 |
| ctgcgtgatg cgtactgtcg tcacattggt gtggagtacg cccacattct ggatccggaa | 1380 |
| cagaaagaat ggctggagca cgtgtcgag accaaacacg taaaaccgac cgtagcgcag | 1440 |
| cagaaatata tcctgtccaa actgaacgcc gccgaggctt cgaaactttt cctgcagacc | 1500 |
| aagtacgtgg gccagaaacg cttcagcctg gagggtgcgg aaagcgttat tccgatgatg | 1560 |
| gatgcagcta tcgatcagtg cgcggaacat ggtctggatg aagtcgttat cggtatgccg | 1620 |
| caccgtggtc gcctgaacgt actggcaaac atcgtcggta accatattc tcagatcttc | 1680 |
| acggaattcg agggcaacct gaacccgtcc caagcccacg gctccggcga cgtaaaatat | 1740 |
| catctgggtg ctaccggcct gtatctgcag atgttcggtg ataacgacat ccaggtatct | 1800 |
| ctgactgcta acccgagcca ctggaggcg gttgatcctg ttctgaaagg tctggttcgc | 1860 |
| gccaaacagg atctgctgga ccacggctct atcgacagcg atggccagcg tgcattcagc | 1920 |
| gttgtaccgc tgatgctgca tggcgacgcg gcgttcgccg gtcagggtgt cgtagcagaa | 1980 |
| actctgaacc tggcgaacct gcctggctat cgcgtgggtg gcaccattca catcatcgtt | 2040 |
| aacaaccaaa tcggtttcac cacggcaccg gagtatagcc gttctagcga atattgcacc | 2100 |
| gacgtagcca aaatgatcgg tgcgccgatc ttccatgtaa acggtgacga tccagaggcc | 2160 |
| tgcgtgtggg tggctcgtct ggccgtagac ttccgccagc gttttaagaa agatgtggtt | 2220 |
| atcgacatgc tgtgctaccg ccgtcgtggt cacaacgaag gtgatgatcc gtctatgact | 2280 |
| aacccgtatg tctatgacgt ggtggacacc aagcgtggtg cacgcaaatc ttacacggag | 2340 |
| gccctgatcg tcgtggcga catctctatg aaagaagcgg aagacgctct gcgtgattac | 2400 |
| cagggtcagc tggaacgtgt gttcaatgag gtgcgtgagc tggaaaagca cggcgtacaa | 2460 |
| ccgtccgaat ccgtagagtc cgatcagatg atccctgctg gtctggcaac tgctgttgat | 2520 |
| aaaagcctgc tggcgcgtat cggcgacgca ttcctggcgc tgccgaatgg ctttaccgcg | 2580 |
| cacccgcgcg tacagccggt actggaaaaa cgtcgtgaaa tggcctacga agtaaaatc | 2640 |
| gattgggcct tcggtgagct gctggccctg gctctctgg tggctgaggg caagctggta | 2700 |
| cgcctgagcg gccaggactc ccgtcgcggc acttttctc agcgtcacag cgtcctgatc | 2760 |
| gatcgtcaca ccggcgaaga attcacgccg ctgcaactgc tggctactaa ctccgatggt | 2820 |
| agcccgaccg gtggtaagtt cctggtgtac gattccccgc tgtccgaata tgctgcagtt | 2880 |
| ggtttcgagt atggttacac cgttggcaac ccggacgcag tggttctgtg gaagcgcag | 2940 |
| ttcggcgatt tcgttaacgg tgcccagtcc attatcgatg agtttattag cagcggcgag | 3000 |
| gccaaatggg gccagctgtc taacgttgtg ctgctgctgc ctcacggcca cgagggtcaa | 3060 |
| ggcccggacc acacctccgc ccgtatcgaa cgcttcctgc agctgtgggc tgaaggctct | 3120 |
| atgaccatcg cgatgccgtc taccccaagc aactacttcc acctgctgcg tcgccacgca | 3180 |
| ctggacggca ttcagcgccc gctgatcgtt ttcacccccaa aatccatgct gcgccacaaa | 3240 |
| gcagctgttt ctgaaatcaa agatttttacg gaaattaaat tccgttctgt gctggaagaa | 3300 |
| ccaacctacg aagacggtat tggcgaccgc aacaaggtaa gccgtatcct gctgacctcc | 3360 |
| ggcaaactgt actacgagct ggcagcacgt aaggcaaaag ataaccgcaa cgacctggcc | 3420 |

```
atcgtccgcc tggaacagct ggcgccactg ccacgccgtc gcctgcgtga aaccctggat    3480
cgctacgaaa acgtaaaaga attcttctgg gtgcaggaag aaccggcaaa ccagggtgcg    3540
tggccgcgct ttggtctgga actgccggaa ctgctgccgg ataaactggc aggtatcaag    3600
cgcatcagcc gtcgcgctat gagcgccccg tcttctggta gctctaaagt acacgctgta    3660
gaacagcaag agatcctgga tgaggccttc ggctaa                              3696
```

```
<210> SEQ ID NO 48
<211> LENGTH: 74
<212> TYPE: DNA
<213> ORGANISM: Artificial sequence
<220> FEATURE:
<223> OTHER INFORMATION: Forward primer for amplification of Bacillus
      subtilis aminotransferase x

<400> SEQUENCE: 48
ggggacaagt ttgtacaaaa aagcaggcta ggaggaatta accatgaagg ttttagtcaa    60
tggccggctg attg                                                      74

<210> SEQ ID NO 49
<211> LENGTH: 62
<212> TYPE: DNA
<213> ORGANISM: Artificial sequence
<220> FEATURE:
<223> OTHER INFORMATION: Reverse primer for amplification of Bacillus
      subtilis aminotransferase x

<400> SEQUENCE: 49
ggggaccact ttgtacaaga aagctgggtt tatgaaatgc tagcagcctg ttgaatgctt    60
tc                                                                   62

<210> SEQ ID NO 50
<211> LENGTH: 82
<212> TYPE: DNA
<213> ORGANISM: Artificial sequence
<220> FEATURE:
<223> OTHER INFORMATION: Forward primer for amplification of Bacillus
      subtilis aminotransferase y

<400> SEQUENCE: 50
ggggacaagt ttgtacaaaa aagcaggcta ggaggaatta accatgactc atgatttgat    60
agaaaaaagt aaaaagcacc tc                                             82

<210> SEQ ID NO 51
<211> LENGTH: 57
<212> TYPE: DNA
<213> ORGANISM: Artificial sequence
<220> FEATURE:
<223> OTHER INFORMATION: Reverse primer for amplification of Bacillus
      subtilis aminotransferase y

<400> SEQUENCE: 51
ggggaccact ttgtacaaga aagctgggtt caatcttcaa ggctcgtaac ctcgtgg       57

<210> SEQ ID NO 52
<211> LENGTH: 64
<212> TYPE: DNA
<213> ORGANISM: Artificial sequence
<220> FEATURE:
<223> OTHER INFORMATION: Forward primer for amplification of Rhodobacter
      sphaeroides aminotransferase

<400> SEQUENCE: 52
```

```
gggacaagt tgtacaaaa aagcaggcta ggaggaatta accatgcccg gttgcggggg    60
cttg                                                              64

<210> SEQ ID NO 53
<211> LENGTH: 51
<212> TYPE: DNA
<213> ORGANISM: Artificial sequence
<220> FEATURE:
<223> OTHER INFORMATION: Reverse primer for amplification of Rhodobacter
      sphaeroides aminotransferase

<400> SEQUENCE: 53
ggggaccact ttgtacaaga aagctgggtt cagacggcgg ccggttcttt c           51

<210> SEQ ID NO 54
<211> LENGTH: 78
<212> TYPE: DNA
<213> ORGANISM: Artificial sequence
<220> FEATURE:
<223> OTHER INFORMATION: Forward primer for amplification of Legionella
      pneumophila aminotransferase

<400> SEQUENCE: 54
ggggacaagt ttgtacaaaa aagcaggcta ggaggaatta accatgagta tcgcatttgt   60
taacggcaag tattgttg                                                78

<210> SEQ ID NO 55
<211> LENGTH: 67
<212> TYPE: DNA
<213> ORGANISM: Artificial sequence
<220> FEATURE:
<223> OTHER INFORMATION: Reverse primer for amplification of Legionella
      pneumophila aminotransferase

<400> SEQUENCE: 55
ggggaccact ttgtacaaga aagctgggtt tagtttacta gttgttggta ggaatcatta   60
attatcc                                                            67

<210> SEQ ID NO 56
<211> LENGTH: 76
<212> TYPE: DNA
<213> ORGANISM: Artificial sequence
<220> FEATURE:
<223> OTHER INFORMATION: Forward primer for amplification of
      Nitrosomonas europaea aminotransferase

<400> SEQUENCE: 56
ggggacaagt ttgtacaaaa aagcaggcta ggaggaatta accatgattt acctcaatgg   60
caaatttctg ccgatg                                                  76

<210> SEQ ID NO 57
<211> LENGTH: 50
<212> TYPE: DNA
<213> ORGANISM: Artificial sequence
<220> FEATURE:
<223> OTHER INFORMATION: Reverse primer for amplification of
      Nitrosomonas europaea aminotransferase

<400> SEQUENCE: 57
ggggaccact ttgtacaaga aagctgggtt tactggcgtg gagcatgccc              50

<210> SEQ ID NO 58
<211> LENGTH: 79
```

<212> TYPE: DNA
<213> ORGANISM: Artificial sequence
<220> FEATURE:
<223> OTHER INFORMATION: Forward primer for amplification of Neisseria
      gonorrhoeae aminotransferase

<400> SEQUENCE: 58
ggggacaagt tgtacaaaa aagcaggcta ggaggaatta accatgagga taaatatgaa    60
ccgtaacgaa attttattc                                                79

<210> SEQ ID NO 59
<211> LENGTH: 56
<212> TYPE: DNA
<213> ORGANISM: Artificial sequence
<220> FEATURE:
<223> OTHER INFORMATION: Reverse primer for amplification of Neisseria
      gonorrhoeae aminotransferase

<400> SEQUENCE: 59
ggggaccact tgtacaaga aagctgggtt catgcagcca tcgccttgaa cacttc         56

<210> SEQ ID NO 60
<211> LENGTH: 66
<212> TYPE: DNA
<213> ORGANISM: Artificial sequence
<220> FEATURE:
<223> OTHER INFORMATION: Forward primer for amplification of Pseudomonas
      aeruginosa aminotransferase

<400> SEQUENCE: 60
ggggacaagt tgtacaaaa aagcaggcta ggaggaatta accatgtcga tggccgatcg    60
tgatgg                                                              66

<210> SEQ ID NO 61
<211> LENGTH: 53
<212> TYPE: DNA
<213> ORGANISM: Artificial sequence
<220> FEATURE:
<223> OTHER INFORMATION: Reverse primer for amplification of Pseudomonas
      aeruginosa aminotransferase

<400> SEQUENCE: 61
ggggaccact tgtacaaga aagctgggtt tacttgacca gggtacgcca ctc            53

<210> SEQ ID NO 62
<211> LENGTH: 67
<212> TYPE: DNA
<213> ORGANISM: Artificial sequence
<220> FEATURE:
<223> OTHER INFORMATION: Forward primer for amplification of
      Rhodopseudomonas palustris aminotransferase

<400> SEQUENCE: 62
ggggacaagt tgtacaaaa aagcaggcta ggaggaatta accatgaagc tgataccgtg    60
ccgcgcc                                                             67

<210> SEQ ID NO 63
<211> LENGTH: 51
<212> TYPE: DNA
<213> ORGANISM: Artificial sequence
<220> FEATURE:
<223> OTHER INFORMATION: Reverse primer for amplification of
      Rhodopseudomonas palustris aminotransferase

<400> SEQUENCE: 63

```
gggggaccact tgtacaaga aagctgggtt caggcgaccg cgcggatcac c        51
```

<210> SEQ ID NO 64
<211> LENGTH: 1353
<212> TYPE: DNA
<213> ORGANISM: Bacillus subtilis

<400> SEQUENCE: 64

```
atggagatga tggggatgga aaacattcag caaaatcagg gattaaagca aaaagatgag      60
caatttgtgt ggcatgccat gaagggagcg catcaagcgg acagcctgat agcccagaag     120
gccgaagggg cctgggtaac cgacacagac ggacgccgct atttggatgc gatgtccggt     180
ttgtggtgcg tcaacattgg ttacggcaga aaggagcttg cggaggctgc ctatgagcaa     240
ctaaaggagc tgccttacta cccgttaacg caaagtcacg cacccgcaat tcaactggcg     300
gaaaagctga atgaatggct tggcggcgat tatgttattt ttttttccaa cagcggatcg     360
gaagcaaacg aaactgcttt taaaattgcc cgccagtacc atctgcaaaa cggcgaccac     420
agccgttata aattcatctc aagatatcgg gcataccacg caatacatt gggagcgctc     480
tcagctaccg gacaggcgca gcggaaatat aaatacgagc ctttgagcca agggttcctg     540
catgcagctc cgccagatat ataccggaat cctgatgatg cagacacgct tgaaagcgca     600
aatgaaatcg accgcatcat gacatgggaa ttaagcgaaa cgattgccgg ggtcattatg     660
gagcccatca ttacaggcgg aggcatccta atgccgccgg acggatatat gaagaaggtg     720
gaggacattt gccggcgcca cggagcccctt ttgatttgcg atgaagtgat ctgcgggttt     780
ggacggacag gtgagccgtt cgggtttatg cactacggtg tgaagcctga tatcattacg     840
atggcaaagg gaatcacaag cgcgtatctg ccattgtcag cgactgctgt gaaacgggac     900
attttcgaag cgtatcaggg ggaagctcct tatgaccgtt ccgccacgt gaacacgttc     960
ggcggaagcc cggctgcctg tgctttggcg ttgaaaaacc tgcaaattat ggaggacgaa    1020
cagctgattc agcgatcccg tgatcttgga gcaaagcttt taggtgagct tcaagctctg    1080
agagaacacc cggcagtcgg ggatgttaga ggaaagggc tgctgatcgg aatcgaactc    1140
gtcaaagaca aattgactaa agagccggct gatgccgcca agtaaaccca agtggttgcg    1200
gcgtgcaaag aaaaagggct gatcatcggc aaaaacggcg atacagtcgc cggctacaac    1260
aatgtcatcc acgttgcgcc gccattttgc ctgacagaag aggacctttc ctttatcgtg    1320
aaaacggtga agaaagctt tcaaacgata taa                                  1353
```

<210> SEQ ID NO 65
<211> LENGTH: 450
<212> TYPE: PRT
<213> ORGANISM: Bacillus subtilis

<400> SEQUENCE: 65

```
Met Glu Met Met Gly Met Glu Asn Ile Gln Gln Asn Gln Gly Leu Lys
 1               5                  10                  15
Gln Lys Asp Glu Gln Phe Val Trp His Ala Met Lys Gly Ala His Gln
            20                  25                  30
Ala Asp Ser Leu Ile Ala Gln Lys Ala Glu Gly Ala Trp Val Thr Asp
        35                  40                  45
Thr Asp Gly Arg Arg Tyr Leu Asp Ala Met Ser Gly Leu Trp Cys Val
    50                  55                  60
Asn Ile Gly Tyr Gly Arg Lys Glu Leu Ala Glu Ala Ala Tyr Glu Gln
65                  70                  75                  80
```

Leu Lys Glu Leu Pro Tyr Tyr Pro Leu Thr Gln Ser His Ala Pro Ala
             85                  90                  95

Ile Gln Leu Ala Glu Lys Leu Asn Glu Trp Leu Gly Gly Asp Tyr Val
        100                 105                 110

Ile Phe Phe Ser Asn Ser Gly Ser Glu Ala Asn Glu Thr Ala Phe Lys
        115                 120                 125

Ile Ala Arg Gln Tyr His Leu Gln Asn Gly Asp His Ser Arg Tyr Lys
    130                 135                 140

Phe Ile Ser Arg Tyr Arg Ala Tyr His Gly Asn Thr Leu Gly Ala Leu
145                 150                 155                 160

Ser Ala Thr Gly Gln Ala Gln Arg Lys Tyr Lys Tyr Glu Pro Leu Ser
                165                 170                 175

Gln Gly Phe Leu His Ala Ala Pro Asp Ile Tyr Arg Asn Pro Asp
            180                 185                 190

Asp Ala Asp Thr Leu Glu Ser Ala Asn Glu Ile Asp Arg Ile Met Thr
            195                 200                 205

Trp Glu Leu Ser Glu Thr Ile Ala Gly Val Ile Met Glu Pro Ile Ile
    210                 215                 220

Thr Gly Gly Gly Ile Leu Met Pro Pro Asp Gly Tyr Met Lys Lys Val
225                 230                 235                 240

Glu Asp Ile Cys Arg Arg His Gly Ala Leu Leu Ile Cys Asp Glu Val
                245                 250                 255

Ile Cys Gly Phe Gly Arg Thr Gly Glu Pro Phe Gly Phe Met His Tyr
            260                 265                 270

Gly Val Lys Pro Asp Ile Ile Thr Met Ala Lys Gly Ile Thr Ser Ala
        275                 280                 285

Tyr Leu Pro Leu Ser Ala Thr Ala Val Lys Arg Asp Ile Phe Glu Ala
    290                 295                 300

Tyr Gln Gly Glu Ala Pro Tyr Asp Arg Phe Arg His Val Asn Thr Phe
305                 310                 315                 320

Gly Gly Ser Pro Ala Ala Cys Ala Leu Ala Leu Lys Asn Leu Gln Ile
                325                 330                 335

Met Glu Asp Glu Gln Leu Ile Gln Arg Ser Arg Asp Leu Gly Ala Lys
            340                 345                 350

Leu Leu Gly Glu Leu Gln Ala Leu Arg Glu His Pro Ala Val Gly Asp
        355                 360                 365

Val Arg Gly Lys Gly Leu Leu Ile Gly Ile Glu Leu Val Lys Asp Lys
    370                 375                 380

Leu Thr Lys Glu Pro Ala Asp Ala Ala Lys Val Asn Gln Val Val Ala
385                 390                 395                 400

Ala Cys Lys Glu Lys Gly Leu Ile Ile Gly Lys Asn Gly Asp Thr Val
                405                 410                 415

Ala Gly Tyr Asn Asn Val Ile His Val Ala Pro Pro Phe Cys Leu Thr
            420                 425                 430

Glu Glu Asp Leu Ser Phe Ile Val Lys Thr Val Lys Glu Ser Phe Gln
        435                 440                 445

Thr Ile
    450

<210> SEQ ID NO 66
<211> LENGTH: 1407
<212> TYPE: DNA
<213> ORGANISM: Pseudomonas aeruginosa

<400> SEQUENCE: 66

```
atgaacgcaa gactgcacgc cacgtccccc ctcggcgacg ccgacctggt ccgtgccgac    60
caggcccact acatgcacgg ctaccacgtg ttcgacgacc accgcgtcaa cggctcgctg   120
aacatcgccg ccggcgacgg cgcctatatc tacgacaccg ccggcaaccg ctacctcgac   180
gcggtgggcg gcatgtggtg caccaacatc ggcctggggc gcgaggaaat ggctcgcacc   240
gtggccgagc agacccgcct gctggcctat tccaatccct tctgcgacat ggccaacccg   300
cgcgccatcg aactctgccg caagctcgcc gagctggccc ccggcgacct cgaccacgtg   360
ttcctcacca ccggcggttc caccgccgtg gacaccgcga tccgcctcat gactactac    420
cagaactgcc gcggcaagcg cgccaagaag cacgtcatca gcgggatcaa cgcctaccac   480
ggctcgacct tcctcggcat gtcgctgggc ggcaagagcg ccgaccggcc ggccgagttc   540
gacttcctcg acgagcgcat ccaccacctc gcctgtccct attactaccg cgctccggaa   600
gggctgggcg aagccgagtt cctcgatggc ctggtggacg agttcgaacg caagatcctc   660
gaactgggcg ccgaccgggt gggggcgttc atctccgagc cggtgttcgg ctccggcggc   720
gtgatcgtcc cgcccgcggg ctaccacagg cggatgtggg agctgtgcca gcgctacgac   780
gtgctgtaca tctccgacga agtggtgacc tccttcggcc gcctcggcca cttcttcgcc   840
agccaggcgg tgttcggcgt acagccggac atcatcctca ccgccaaggg cctcacctcc   900
ggctaccagc cgctgggcgc gtgcatcttc tcccggcgca tctgggaggt gatcgccgag   960
ccggacaagg gccgctgctt cagccatggt ttcacctact ccggccaccc ggtggcctgc  1020
gcggcggcgc tgaagaacat cgagatcatc gagcgcgagg gcttgctcgc ccacgccgac  1080
gaggtcggcc gctacttcga ggagcgcctg caaagcctcc gcgacctgcc catcgtcggc  1140
gacgtgcgcg gatgcgcttc catggcctgt gtcgagttcg tcgccgacaa ggcgagcaag  1200
gcgctgtttc cggaaagcct gaacatcggc gagtgggtcc acctgcgggc gcagaagcgc  1260
ggcctgctgg ttcgtccgat cgtccacctg aacgtgatgt cgccgccgct gatcctcacc  1320
cgcgaacagg tcgataccgt ggtccgggtg ctgcgcgaga gcatcgagga aaccgtggag  1380
gatcttgtcc gcgccggtca ccggtaa                                     1407
```

<210> SEQ ID NO 67
<211> LENGTH: 468
<212> TYPE: PRT
<213> ORGANISM: Pseudomonas aeruginosa

<400> SEQUENCE: 67

Met Asn Ala Arg Leu His Ala Thr Ser Pro Leu Gly Asp Ala Asp Leu
1               5                   10                  15

Val Arg Ala Asp Gln Ala His Tyr Met His Gly Tyr His Val Phe Asp
            20                  25                  30

Asp His Arg Val Asn Gly Ser Leu Asn Ile Ala Ala Gly Asp Gly Ala
        35                  40                  45

Tyr Ile Tyr Asp Thr Ala Gly Asn Arg Tyr Leu Asp Ala Val Gly Gly
    50                  55                  60

Met Trp Cys Thr Asn Ile Gly Leu Gly Arg Glu Glu Met Ala Arg Thr
65                  70                  75                  80

Val Ala Glu Gln Thr Arg Leu Leu Ala Tyr Ser Asn Pro Phe Cys Asp
                85                  90                  95

Met Ala Asn Pro Arg Ala Ile Glu Leu Cys Arg Lys Leu Ala Glu Leu
            100                 105                 110

Ala Pro Gly Asp Leu Asp His Val Phe Leu Thr Thr Gly Gly Ser Thr

```
            115                 120                 125
Ala Val Asp Thr Ala Ile Arg Leu Met His Tyr Tyr Gln Asn Cys Arg
        130                 135                 140

Gly Lys Arg Ala Lys Lys His Val Ile Thr Arg Ile Asn Ala Tyr His
145                 150                 155                 160

Gly Ser Thr Phe Leu Gly Met Ser Leu Gly Lys Ser Ala Asp Arg
                165                 170                 175

Pro Ala Glu Phe Asp Phe Leu Asp Glu Arg Ile His His Leu Ala Cys
                180                 185                 190

Pro Tyr Tyr Tyr Arg Ala Pro Glu Gly Leu Gly Glu Ala Glu Phe Leu
                195                 200                 205

Asp Gly Leu Val Asp Glu Phe Glu Arg Lys Ile Leu Glu Leu Gly Ala
        210                 215                 220

Asp Arg Val Gly Ala Phe Ile Ser Glu Pro Val Phe Gly Ser Gly Gly
225                 230                 235                 240

Val Ile Val Pro Pro Ala Gly Tyr His Arg Arg Met Trp Glu Leu Cys
                245                 250                 255

Gln Arg Tyr Asp Val Leu Tyr Ile Ser Asp Glu Val Val Thr Ser Phe
                260                 265                 270

Gly Arg Leu Gly His Phe Phe Ala Ser Gln Ala Val Phe Gly Val Gln
        275                 280                 285

Pro Asp Ile Ile Leu Thr Ala Lys Gly Leu Thr Ser Gly Tyr Gln Pro
        290                 295                 300

Leu Gly Ala Cys Ile Phe Ser Arg Arg Ile Trp Glu Val Ile Ala Glu
305                 310                 315                 320

Pro Asp Lys Gly Arg Cys Phe Ser His Gly Phe Thr Tyr Ser Gly His
                325                 330                 335

Pro Val Ala Cys Ala Ala Ala Leu Lys Asn Ile Glu Ile Ile Glu Arg
                340                 345                 350

Glu Gly Leu Leu Ala His Ala Asp Glu Val Gly Arg Tyr Phe Glu Glu
        355                 360                 365

Arg Leu Gln Ser Leu Arg Asp Leu Pro Ile Val Gly Asp Val Arg Gly
        370                 375                 380

Met Arg Phe Met Ala Cys Val Glu Phe Val Ala Asp Lys Ala Ser Lys
385                 390                 395                 400

Ala Leu Phe Pro Glu Ser Leu Asn Ile Gly Glu Trp Val His Leu Arg
                405                 410                 415

Ala Gln Lys Arg Gly Leu Leu Val Arg Pro Ile Val His Leu Asn Val
                420                 425                 430

Met Ser Pro Pro Leu Ile Leu Thr Arg Glu Gln Val Asp Thr Val Val
        435                 440                 445

Arg Val Leu Arg Glu Ser Ile Glu Glu Thr Val Glu Asp Leu Val Arg
        450                 455                 460

Ala Gly His Arg
465

<210> SEQ ID NO 68
<211> LENGTH: 1335
<212> TYPE: DNA
<213> ORGANISM: Pseudomonas aeruginosa

<400> SEQUENCE: 68
atgacaatga atgacgagcc gcagtcgagc agcctcgaca acttctggat gcccttcacc      60
gccaaccgcc agttcaaggc gcggccgcgc ctgctggaaa gcgccgaagg catccactat     120
```

-continued

```
atcgcccagg gcgggcgccg catcctcgac ggcaccgccg gcctctggtg ctgcaatgcc      180
ggccacggcc ggcgcgagat cagcgaagcg gtggcccggc agatcgccac cctcgactac      240
gccccgccgt tccagatggg tcacccgctg ccgttcgaac tcgccgcgcg gctgacggaa      300
atcgccccgc cgagcctgaa caaagtattc ttcaccaact ccggctcgga atcggcggac      360
accgcgctga agatcgccct tgcctaccag cgcgccatcg gccagggcac ccgcacccgc      420
ctgatcggcc gcgaactggg ctaccacggg gtcggcttcg gcggcctgtc ggtaggcggt      480
atggtcaaca accgcaaggc cttctccgcc aacctgctgc cggggtcga ccacctgccg       540 cacaccctgg acgtcgcccg caacgccttc accgtcggcc tgcccgagca tggcgtggaa      600
aaggccgagg agctggaacg cctggtgacc ctgcacggcg ccgagaatat cgccgcggtg      660
atcgtcgagc cgatgtccgg ctcggccggc gtggtgctgc cgcccaaggg ctaccttcag      720
cggctgcgcg agataacccg caagcatggc atcctgctga tcttcgacga agtgatcacc      780
ggtttcggcc gcgtcggcga agccttcgcc gcgcagcgct ggggcgtcgt cccggacctg      840
ctgacctgcg ccaaggggct gaccaacggc agcatcccga tgggcgccgt attcgtcgac      900
gagaagatcc atgctgcctt catgcaaggc ccgcagggcg ccatcgagtt cttccacggc      960
tatacctatt ccggccatcc ggtagcctgc gccgccgccc tggcgaccct ggacatctac     1020
cgtcgcgacg acctgttcca gcgggccgtc gaactggaag ctactggca ggacgcgctg      1080 ttcagcctgc gcgacctgcc caacgtggtc gacatccgcg ccgtaggcct ggtcggcggc     1140
gtgcaactgg cgccgcacgc ggacggcccc ggcaagcgcg gctacgacgt cttcgagcgc     1200
tgcttctggg agcacgacct gatggtccgg gtgaccggcg acatcatcgc catgtcgccg     1260
ccgctgatca tcgacaagcc ccacatcgac cagatcgtcg agcgcctggc ccaggccatc    1320
cgcgccagcg tctga                                                     1335
```

<210> SEQ ID NO 69
<211> LENGTH: 444
<212> TYPE: PRT
<213> ORGANISM: Pseudomonas aeruginosa

<400> SEQUENCE: 69

```
Met Thr Met Asn Asp Glu Pro Gln Ser Ser Leu Asp Asn Phe Trp
1               5                   10                  15

Met Pro Phe Thr Ala Asn Arg Gln Phe Lys Ala Arg Pro Arg Leu Leu
                20                  25                  30

Glu Ser Ala Glu Gly Ile His Tyr Ile Ala Gln Gly Gly Arg Arg Ile
        35                  40                  45

Leu Asp Gly Thr Ala Gly Leu Trp Cys Cys Asn Ala Gly His Gly Arg
    50                  55                  60

Arg Glu Ile Ser Glu Ala Val Ala Arg Gln Ile Ala Thr Leu Asp Tyr
65                  70                  75                  80

Ala Pro Pro Phe Gln Met Gly His Pro Leu Pro Phe Glu Leu Ala Ala
                85                  90                  95

Arg Leu Thr Glu Ile Ala Pro Pro Ser Leu Asn Lys Val Phe Phe Thr
            100                 105                 110

Asn Ser Gly Ser Glu Ser Ala Asp Thr Ala Leu Lys Ile Ala Leu Ala
        115                 120                 125

Tyr Gln Arg Ala Ile Gly Gln Gly Thr Arg Thr Arg Leu Ile Gly Arg
    130                 135                 140

Glu Leu Gly Tyr His Gly Val Gly Phe Gly Gly Leu Ser Val Gly Gly
```

```
            145                 150                 155                 160
Met Val Asn Asn Arg Lys Ala Phe Ser Ala Asn Leu Leu Pro Gly Val
                165                 170                 175

Asp His Leu Pro His Thr Leu Asp Val Ala Arg Asn Ala Phe Thr Val
            180                 185                 190

Gly Leu Pro Glu His Gly Val Glu Lys Ala Glu Leu Glu Arg Leu
        195                 200                 205

Val Thr Leu His Gly Ala Glu Asn Ile Ala Ala Ile Val Glu Pro
    210                 215                 220

Met Ser Gly Ser Ala Gly Val Val Leu Pro Lys Gly Tyr Leu Gln
225                 230                 235                 240

Arg Leu Arg Glu Ile Thr Arg Lys His Gly Ile Leu Ile Phe Asp
                245                 250                 255

Glu Val Ile Thr Gly Phe Gly Arg Val Gly Ala Phe Ala Ala Gln
                260                 265                 270

Arg Trp Gly Val Val Pro Asp Leu Leu Thr Cys Ala Lys Gly Leu Thr
            275                 280                 285

Asn Gly Ser Ile Pro Met Gly Ala Val Phe Val Asp Glu Lys Ile His
    290                 295                 300

Ala Ala Phe Met Gln Gly Pro Gln Gly Ala Ile Glu Phe His Gly
305                 310                 315                 320

Tyr Thr Tyr Ser Gly His Pro Val Ala Cys Ala Ala Leu Ala Thr
                325                 330                 335

Leu Asp Ile Tyr Arg Arg Asp Asp Leu Phe Gln Arg Ala Val Glu Leu
            340                 345                 350

Glu Gly Tyr Trp Gln Asp Ala Leu Phe Ser Leu Arg Asp Leu Pro Asn
        355                 360                 365

Val Val Asp Ile Arg Ala Val Gly Leu Val Gly Gly Val Gln Leu Ala
    370                 375                 380

Pro His Ala Asp Gly Pro Gly Lys Arg Gly Tyr Asp Val Phe Glu Arg
385                 390                 395                 400

Cys Phe Trp Glu His Asp Leu Met Val Arg Val Thr Gly Asp Ile Ile
                405                 410                 415

Ala Met Ser Pro Pro Leu Ile Ile Asp Lys Pro His Ile Asp Gln Ile
                420                 425                 430

Val Glu Arg Leu Ala Gln Ala Ile Arg Ala Ser Val
            435                 440

<210> SEQ ID NO 70
<211> LENGTH: 71
<212> TYPE: DNA
<213> ORGANISM: Artificial sequence
<220> FEATURE:
<223> OTHER INFORMATION: Forward primer for amplification of Bacillus
      subtilis aminotransferase (gi16077991)

<400> SEQUENCE: 70
ggggacaagt ttgtacaaaa aagcaggcta ggaggaatta accatggaga tgatggggat      60
ggaaaacatt c                                                          71

<210> SEQ ID NO 71
<211> LENGTH: 65
<212> TYPE: DNA
<213> ORGANISM: Artificial sequence
<220> FEATURE:
<223> OTHER INFORMATION: Reverse primer for amplification of Bacillus
      subtilis aminotransferase (gi16077991)
```

<400> SEQUENCE: 71
ggggaccact tgtacaaga aagctgggtt tatatcgttt gaaagctttc tttcaccgtt    60
ttcac    65

<210> SEQ ID NO 72
<211> LENGTH: 66
<212> TYPE: DNA
<213> ORGANISM: Artificial sequence
<220> FEATURE:
<223> OTHER INFORMATION: Forward primer for amplification of Pseudomonas
      aeruginosa aminotransferase (gi9951072)

<400> SEQUENCE: 72
ggggacaagt tgtacaaaaa aagcaggcta ggaggaatta accatgaacg caagactgca    60
cgccac    66

<210> SEQ ID NO 73
<211> LENGTH: 48
<212> TYPE: DNA
<213> ORGANISM: Artificial sequence
<220> FEATURE:
<223> OTHER INFORMATION: Reverse primer for amplification of Pseudomonas
      aeruginosa aminotransferase (gi9951072)

<400> SEQUENCE: 73
ggggaccact tgtacaaga aagctgggtt taccggtgac cggcgcgg    48

<210> SEQ ID NO 74
<211> LENGTH: 69
<212> TYPE: DNA
<213> ORGANISM: Artificial sequence
<220> FEATURE:
<223> OTHER INFORMATION: Forward primer for amplification of Pseudomonas
      aeruginosa aminotransferase (gi9951630)

<400> SEQUENCE: 74
ggggacaagt tgtacaaaaa aagcaggcta ggaggaatta accatgacaa tgaatgacga    60
gccgcagtc    69

<210> SEQ ID NO 75
<211> LENGTH: 49
<212> TYPE: DNA
<213> ORGANISM: Artificial sequence
<220> FEATURE:
<223> OTHER INFORMATION: Reverse primer for amplification of Pseudomonas
      aeruginosa aminotransferase (gi9951630)

<400> SEQUENCE: 75
ggggaccact tgtacaaga aagctgggtt cagacgctgg cgcggatgg    49

<210> SEQ ID NO 76
<211> LENGTH: 57
<212> TYPE: DNA
<213> ORGANISM: Artificial sequence
<220> FEATURE:
<223> OTHER INFORMATION: Forward primer -continued

<400> SEQUENCE: 76
aaatttacta gtaagaattt ttgaggaggc aatataaatg aataaaccac agtcttg    57

<210> SEQ ID NO 77
<211> LENGTH: 32
<212> TYPE: DNA
<213> ORGANISM: Artificial sequence
<220> FEATURE:
<223> OTHER INFORMATION: Reverse primer

<400> SEQUENCE: 77
aaatttggat cctacaagaa agctgggttt ac    32

<210> SEQ ID NO 78
<211> LENGTH: 58
<212> TYPE: DNA
<213> ORGANISM: Artificial sequence
<220> FEATURE:
<223> OTHER INFORMATION: Forward primer

<400> SEQUENCE: 78
aaatttacta gtaagaattt ttgaggaggc aatataaatg aacagccaaa tcaccaac    58

<210> SEQ ID NO 79
<211> LENGTH: 37
<212> TYPE: DNA
<213> ORGANISM: Artificial sequence
<220> FEATURE:
<223> OTHER INFORMATION: Reverse primer

<400> SEQUENCE: 79
aaatttggat ccactttgta caagaaagct gggttca    37

<210> SEQ ID NO 80
<211> LENGTH: 57
<212> TYPE: DNA
<213> ORGANISM: Artificial sequence
<220> FEATURE:
<223> OTHER INFORMATION: Forward primer

<400> SEQUENCE: 80
aaatttggat ccgttgagga ggcctcaaaa atgtccgaga tcactctggg caaatac    57

<210> SEQ ID NO 81
<211> LENGTH: 35
<212> TYPE: DNA
<213> ORGANISM: Artificial sequence
<220> FEATURE:
<223> OTHER INFORMATION: Reverse primer

<400> SEQUENCE: 81
aaatttggcg cgccattact gtttagcgtt agttg    35

<210> SEQ ID NO 82
<211> LENGTH: 52
<212> TYPE: DNA
<213> ORGANISM: Artificial sequence
<220> FEATURE:
<223> OTHER INFORMATION: Forward primer

<400> SEQUENCE: 82
aaatttggat ccgttgagga ggcctcaaaa atgtatactg ttggtgatta tc    52

<210> SEQ ID NO 83
<211> LENGTH: 37

```
<212> TYPE: DNA
<213> ORGANISM: Artificial sequence
<220> FEATURE:
<223> OTHER INFORMATION: Reverse primer

<400> SEQUENCE: 83
aaatttggcg cgccattact tgttctgctc cgcaaac                           37
```

PREPARATION OF 6-AMINOCAPROIC ACID FROM 5-FORMYL VALERI C ACID

This application is a continuation of application Ser. No. 12/921,733 (allowed), filed Dec. 21, 2010 (published as US 2011-0171699 A1), which is a U.S. national phase of International Application No. PCT/NL2009/050117, filed Mar. 11, 2009, which designated the U.S. and claims priority to European Application No. 08152584.2, filed Mar. 11, 2008, the entire contents of each of which is hereby incorporated by reference.

The invention relates to a method for preparing 6-aminocaproic acid (hereinafter also referred to as '6-ACA'). The invention further relates to a method for preparing ϵ-caprolactam (hereafter referred to as 'caprolactam') from 6-ACA. The invention further relates to a host cell which may be used in the preparation of 6-ACA or caprolactam.

Caprolactam is a lactam which may be used for the production of polyamide, for instance nylon-6 or nylon-6,12 (a copolymer of caprolactam and laurolactam). Various manners of preparing caprolactam from bulk chemicals are known in the art and include the preparation of caprolactam from cyclohexanone, toluene, phenol, cyclohexanol, benzene or cyclohexane. These intermediate compounds are generally obtained from mineral oil. In view of a growing desire to prepare materials using more sustainable technology it would be desirable to provide a method wherein caprolactam is prepared from an intermediate compound that can be obtained from a biologically renewable source or at least from an intermediate compound that is converted into caprolactam using a biochemical method. Further, it would be desirable to provide a method that requires less energy than conventional chemical processes making use of bulk chemicals from petrochemical origin.

It is known to prepare caprolactam from 6-ACA, e.g. as described in U.S. Pat. No. 6,194,572. As disclosed in WO 2005/068643, 6-ACA may be prepared biochemically by converting 6-aminohex-2-enoic acid (6-AHEA) in the presence of an enzyme having α,β-enoate reductase activity. The 6-AHEA may be prepared from lysine, e.g. biochemically or by pure chemical synthesis. Although the preparation of 6-ACA via the reduction of 6-RHEA is feasible by the methods disclosed in WO 2005/068643, the inventors have found that—under the reduction reaction conditions—6-AHEA may spontaneously and substantially irreversibly cyclise to form an undesired side-product, notably β-homoproline. This cyclisation may be a bottleneck in the production of 6-ACA, and may lead to a considerable loss in yield.

It is an object of the invention to provide a novel method for preparing 6-ACA or caprolactam—which may, inter alia, be used for the preparation of polyamide—or an intermediate compound for the preparation of 6-ACA or caprolactam, that can serve as an alternative for known methods.

It is a further object to provide a novel method that would overcome one or more of the drawbacks mentioned above.

One or more further objects which may be solved in accordance with the invention, will follow from the description, below.

It has now been found possible to prepare 6-ACA from a specific starting compound, namely it has been found possible to prepare 6-aminocaproic acid (6-ACA), wherein the 6-aminocaproic acid is prepared from 2-oxo-heptanedioic acid also known as α-ketopimelic acid (AKP). In particular, the preparation may be carried out in two or more reaction steps. For instance, a method is provided wherein AKP is first converted into 5-formylpentanoate (5-formylvaleric acid, 5-FVA), which 5-FVA is converted into 6-ACA. Further a method is provided wherein AKP is first converted into alpha-aminopimelic acid (AAP). Thereafter, AAP is converted into 6-ACA.

The inventors realised that in principle, it is possible to prepare 6-ACA from AKP in an entirely chemical (i.e. without the use of a biocatalyst) manner. Examples of suitable chemical ways of carrying out individual reaction steps are given herein below. However, the inventors also realised that it is possible to prepare 6-ACA biochemically from AKP.

Accordingly, the present invention in particular relates to a method for preparing 6-ACA, wherein the 6-ACA is prepared from AKP, using at least one biocatalyst.

The invention further relates to a method, wherein 6-ACA is prepared from 5-formylpentanoate (5-formylvaleric acid, 5-FVA), using a biocatalyst. As indicated above, the 5-FVA may be obtained from AKP.

In an embodiment, 6-ACA prepared in a method of the invention is used for preparing caprolactam. Such method comprises cyclising the 6-amino-caproic acid, optionally in the presence of a biocatalyst.

When referring herein to carboxylic acids or carboxylates, e.g. 6-ACA, 2-aminoheptanedioic acid (α-aminopimelic acid, herein after abbreviated as 'AAP'), another amino acid, 5-FVA or AKP, these terms are meant to include the protonated carboxylic acid group (i.e. the neutral group), their corresponding carboxylate (their conjugated bases) as well as salts thereof. When referring herein to amino acids, e.g. 6-ACA, this term is meant to include amino acids in their zwitterionic form (in which the amino group is in the protonated and the carboxylate group is in the deprotonated form), the amino acid in which the amino group is protonated and the carboxylic group is in its neutral form, and the amino acid in which the amino group is in its neutral form and the carboxylate group is in the deprotonated form, as well as salts thereof.

In accordance with the invention, no problems have been noticed with respect to an undesired cyclisation of an intermediate product, when forming 6-ACA and optionally caprolactam, resulting in a loss of yield.

It is envisaged that a method of the invention allows a comparable or even better yield than the method described in WO 2005/68643. It is envisaged that a method of the invention may in particular be favourable if a use is made of a living organism—in particular in a method wherein growth and maintenance of the organism is taken into account.

It is further envisaged that in an embodiment of the invention the productivity of 6-ACA (g/l·h formed) in a method of the invention may be improved.

The term "or" as used herein is defined as "and/or" unless specified otherwise.

The term "a" or "an" as used herein is defined as "at least one" unless specified otherwise.

When referring to a noun (e.g. a compound, an additive, etc.) in the singular, the plural is meant to be included.

When referring to a compound of which stereoisomers exist, the compound may be any of such stereoisomers or a combination thereof. Thus, when referred to, e.g., an amino acid of which enantiomers exist, the amino acid may be the L-enantiomer, the D-enantiomer or a combination thereof. In case a natural stereoisomer exists, the compound is preferably a natural stereoisomer.

When an enzyme is mentioned with reference to an enzyme class (EC) between brackets, the enzyme class is a class wherein the enzyme is classified or may be classified, on the basis of the Enzyme Nomenclature provided by the Nomenclature Committee of the International Union of Biochemistry and Molecular Biology (NC-IUBMB), which nomenclature may be found at URL:chem[dot]qmul[dot]ac [dot]uk[slash]iubmb[slash]enzyme[slash]. Other suitable enzymes that have not (yet) been classified in a specified class but may be classified as such, are meant to be included.

The term "homologue" is used herein in particular for polynucleotides or polypeptides having a sequence identity of at least 30%, preferably at least 40%, more preferably at least 60%, more preferably at least 65%, more preferably at least 70%, more preferably at least 75%, more preferably at least 80%, in particular at least 85%, more in particular at least 90%, at least 91%, at least 92%, at least 93%, at least 94%, at least 95%, at least 96%, at least 97%, at least 98% or at least 99%. The term homologue is also meant to include nucleic acid sequences (polynucleotide sequences) which differ from another nucleic acid sequence due to the degeneracy of the genetic code and encode the same polypeptide sequence.

Sequence identity or similarity is herein defined as a relationship between two or more polypeptide sequences or two or more nucleic acid sequences, as determined by comparing the sequences. Usually, sequence identities or similarities are compared over the whole length of the sequences, but may however also be compared only for a part of the sequences aligning with each other. In the art, "identity" or "similarity" also means the degree of sequence relatedness between polypeptide sequences or nucleic acid sequences, as the case may be, as determined by the match between such sequences. Preferred methods to determine identity or similarity are designed to give the largest match between the sequences tested. In context of this invention a preferred computer program method to determine identity and similarity between two sequences includes BLASTP and BLASTN (Altschul, S. F. et al., J. Mol. Biol. 1990, 215, 403-410, publicly available from NCBI and other sources (BLAST Manual, Altschul, S., et al., NCBI NLM NIH Bethesda, Md. 20894). Preferred parameters for polypeptide sequence comparison using BLASTP are gap open 10.0, gap extend 0.5, Blosum 62 matrix. Preferred parameters for nucleic acid sequence comparison using BLASTN are gap open 10.0, gap extend 0.5, DNA full matrix (DNA identity matrix).

In accordance with the invention, a biocatalyst is used, i.e. at least one reaction step in the method is catalysed by a biological material or moiety derived from a biological source, for instance an organism or a biomolecule derived there from. The biocatalyst may in particular comprise one or more enzymes. The biocatalyst may be used in any form. In an embodiment, one or more enzymes are used isolated from the natural environment (isolated from the organism it has been produced in), for instance as a solution, an emulsion, a dispersion, (a suspension of) freeze-dried cells, as a lysate, or immobilised on a support. In an embodiment, one or more enzymes form part of a living organism (such as living whole cells).

The enzymes may perform a catalytic function inside the cell. It is also possible that the enzyme may be secreted into a medium, wherein the cells are present.

Living cells may be growing cells, resting or dormant cells (e.g. spores) or cells in a stationary phase. It is also possible to use an enzyme forming part of a permeabilised cell (i.e. made permeable to a substrate for the enzyme or a precursor for a substrate for the enzyme or enzymes).

A biocatalyst used in a method of the invention may in principle be any organism, or be obtained or derived from any organism. The organism may be eukaryotic or prokaryotic. In particular the organism may be selected from animals (including humans), plants, bacteria, archaea, yeasts and fungi.

In an embodiment a biocatalyst originates from an animal, in particular from a part thereof—e.g. liver, pancreas, brain, kidney, heart or other organ. The animal may in particular be selected from the group of mammals, more in particular selected from the group of Leporidae, Muridae, Suidae and Bovidae.

Suitable plants in particular include plants selected from the group of *Asplenium*; Cucurbitaceae, in particular *Curcurbita*, e.g. *Curcurbita moschata* (squash), or *Cucumis*; *Mercurialis*, e.g. *Mercurialis perennis*; *Hydnocarpus*; and *Ceratonia*.

Suitable bacteria may in particular be selected amongst the group of *Vibrio, Pseudomonas, Bacillus, Corynebacterium, Brevibacterium, Enterococcus, Streptococcus, Klebsiella, Lactococcus, Lactobacillus, Clostridium, Escherichia, Thermus, Mycobacterium, Zymomonas, Proteus, Agrobacterium, Geobacillus, Acinetobacter, Ralstonia, Rhodobacter, Paracoccus, Novosphingobium, Nitrosomonas, Legionella, Neisseria, Rhodopseudomonas, Staphylococcus, Deinococcus* and *Salmonella*.

Suitable archaea may in particular be selected amongst the group of *Archaeoglobus, Aeropyrum, Halobacterium, Methanosarcina, Methanococcus, Thermoplasma, Pyrobaculum, Methanocaldococcus, Methanobacterium, Methanosphaera, Methanopyrus* and *Methanobrevibacter*.

Suitable fungi may in particular be selected amongst the group of *Rhizopus, Neurospora, Penicillium* and *Aspergillus*.

A suitable yeast may in particular be selected amongst the group of *Candida, Hansenula, Kluyveromyces* and *Saccharomyces*.

It will be clear to the person skilled in the art that use can be made of a naturally occurring biocatalyst (wild type) or a mutant of a naturally occurring biocatalyst with suitable activity in a method according to the invention. Properties of a naturally occurring biocatalyst may be improved by biological techniques known to the skilled person in the art, such as e.g. molecular evolution or rational design. Mutants of wild-type biocatalysts can for example be made by modifying the encoding DNA of an organism capable of acting as a biocatalyst or capable of producing a biocatalytic moiety (such as an enzyme) using mutagenesis techniques known to the person skilled in the art (random mutagenesis, site-directed mutagenesis, directed evolution, gene recombination, etc.). In particular the DNA may be modified such that it encodes an enzyme that differs by at least one amino acid from the wild-type enzyme, so that it encodes an enzyme that comprises one or more amino acid substitutions, deletions and/or insertions compared to the wild-type, or such that the mutants combine sequences of two or more parent enzymes or by effecting the expression of the thus modified DNA in a suitable (host) cell. The latter may be achieved by methods known to the skilled person in the art such as codon optimisation or codon pair optimisation, e.g. based on a method as described in WO 2008/000632.

A mutant biocatalyst may have improved properties, for instance with respect to one or more of the following aspects: selectivity towards the substrate, activity, stability, solvent tolerance, pH profile, temperature profile, substrate profile, susceptibility to inhibition, cofactor utilisation and substrate-affinity. Mutants with improved properties can be identified by applying e.g. suitable high through-put screening or selection methods based on such methods known to the skilled person in the art.

When referred to a biocatalyst, in particular an enzyme, from a particular source, recombinant biocatalysts, in particular enzymes, originating from a first organism, but actually produced in a (genetically modified) second organism, are specifically meant to be included as biocatalysts, in particular enzymes, from that first organism.

In a preferred method of the invention, the preparation comprises a biocatalytic (usually an enzymatic) reaction in the presence of a biocatalyst capable of catalysing the decarboxylation of an α-keto acid or an amino acid (i.e. a compound comprising at least one carboxylic acid group and at least one amino group). An enzyme having such catalytic activity may therefore be referred to as an α-keto acid decarboxylase respectively an amino acid decarboxylase.

Said acid preferably is a diacid, wherein the said biocatalyst is selective towards the acid group next to the keto- or amino-group.

In general, a suitable decarboxylase has α-ketopimelate decarboxylase activity, capable of catalysing the conversion of AKP into 5-FVA or α-aminopimelate decarboxylase activity, capable of catalysing the conversion of AAP to 6-ACA.

An enzyme capable of decarboxylating an α-keto acid or an amino acid may in particular be selected from the group of decarboxylases (E.C. 4.1.1), preferably from the group of oxaloacetate decarboxylases (EC 4.1.1.3), diaminopimelate decarboxylases (EC 4.1.1.20), branched chain α-keto acid decarboxylases (EC 4.1.1.72), α-ketoisovalerate decarboxylases, α-ketoglutarate decarboxylases (EC 4.1.1.71), and pyruvate decarboxylases (EC 4.1.1.1).

One or more other suitable decarboxylases may be selected amongst the group of oxalate decarboxylases (EC 4.1.1.2), acetoacetate decarboxylases (EC 4.1.1.4), valine decarboxylases/leucine decarboxylases (EC 4.1.1.14), glutamate decarboxylases (EC 4.1.1.15), aspartate 1-decarboxylases (EC 4.1.1.11), 3-hydroxyglutamate decarboxylases (EC 4.1.1.16), ornithine decarboxylases (EC 4.1.1.17), lysine decarboxylases (EC 4.1.1.18), arginine decarboxylases (EC 4.1.1.19), 2-oxoglutarate decarboxylases (EC 4.1.1.71), and diaminobutyrate decarboxylases (EC 4.1.1.86)

A decarboxylase may in particular be a decarboxylase of an organism selected from the group of squashes; cucumbers; yeasts; fungi, e.g. *Saccharomyces cerevisiae, Candida flareri, Hansenula* sp., *Kluyveromyces marxianus, Rhizopus javanicus*, and *Neurospora crassa*; mammals, in particular from mammalian brain; and bacteria, such as *Escherichia coli, Lactococcus lactis, Mycobacterium tuberculosis, Pseudomonas* sp. and *Zymomonas mobilis*.

The pyruvate decarboxylase may originate from *Saccharomyces cerevisiae* or *Zymomonas mobilis*. In particular, pyruvate decarboxylase mutant I472A from *Zymomonas mobilis* may be used.

Glutamate decarboxylase, diaminopimelate decarboxylase or aspartate decarboxylase from *Escherichia coli* (*E. coli*) may be used.

Glutamate decarboxylase from *Neurospora crassa, Mycobacterium leprae, Clostridium perfringens, Lactobacillus brevis, Mycobacterium tuberculosis, Streptococcus* or *Lactococcus* may be used. Examples of *Lactococcus* species from which the glutamate decarboxylase may originate in particular include *Lactococcus lactis*, such as *Lactococcus lactis* strain B1157, *Lactococcus lactis* IFPL730, more in particular *Lactococcus lactis* var. *maltigenes* (formerly named *Streptococcus lactis* var. *maltigenes*).

An oxaloacetate decarboxylase from *Pseudomonas* may in particular be used.

A branched-chain alpha-keto acid decarboxylase from *Lactococcus lactis* may be used. More in particular, an alpha-ketoisovalerate decarboxylase from *Lactococcus lactis* may be used.

An alpha-ketoglutarate decarboxylase from *Mycobacterium tuberculosis* may in particular be used.

In a preferred method of the invention, the preparation of 6-ACA comprises an enzymatic reaction in the presence of an enzyme capable of catalysing a transamination reaction in the presence of an amino donor, selected from the group of aminotransferases (E.C. 2.6.1).

In general, a suitable aminotransferase has 6-aminocaproic acid 6-aminotransferase activity, capable of catalysing the conversion of 5-FVA into 6-ACA or α-aminopimelate 2-aminotransferase activity, capable of catalysing the conversion of AKP into AAP.

The aminotransferase may in particular be selected amongst the group of β-aminoisobutyrate:α-ketoglutarate aminotransferases, β-alanine aminotransferases, aspartate aminotransferases, 4-amino-butyrate aminotransferases (EC 2.6.1.19), L-lysine 6-aminotransferase (EC 2.6.1.36), 2-aminoadipate aminotransferases (EC 2.6.1.39), 5-aminovalerate aminotransferases (EC 2.6.1.48), 2-aminohexanoate aminotransferases (EC 2.6.1.67) and lysine:pyruvate 6-aminotransferases (EC 2.6.1.71).

In an embodiment an aminotransferase may be selected amongst the group of alanine aminotransferases (EC 2.6.1.2), leucine aminotransferases (EC 2.6.1.6), alanine-oxo-acid aminotransferases (EC 2.6.1.12), β-alanine-pyruvate aminotransferases (EC 2.6.1.18), (S)-3-amino-2-methylpropionate aminotransferases (EC 2.6.1.22), L,L-diaminopimelate aminotransferase (EC 2.6.1.83).

The aminotransferase may in particular be selected amongst aminotransferases from a mammal; *Mercurialis*, in particular *Mercurialis perennis*, more in particular shoots of *Mercurialis perennis*; *Asplenium*, more in particular *Asplenium unilaterale* or *Asplenium septentrionale*; *Ceratonia*, more in particular *Ceratonia siliqua*; *Rhodobacter*, in particular *Rhodobacter sphaeroides*, *Staphylococcus*, in particular *Staphylococcus aureus*; *Vibrio*, in particular *Vibrio fluvialis*; *Pseudomonas*, in particular *Pseudomonas aeruginosa*; *Rhodopseusomonas*; *Bacillus*, in particular *Bacillus weihenstephanensis* and *Bacillus subtilis*; *Legionella*; *Nitrosomas*; *Neisseria*; or yeast, in particular *Saccharomyces cerevisiae*.

In case the enzyme is of a mammal, it may in particular originate from mammalian kidney, from mammalian liver, from mammalian heart or from mammalian brain. For instance a suitable enzyme may be selected amongst the group of β-aminoisobutyrate:α-ketoglutarate aminotransferase from mammalian kidney, in particular β-aminoisobutyrate:α-ketoglutarate aminotransferase from hog kidney; β-alanine aminotransferase from mammalian liver, in particular β-alanine aminotransferase from rabbit liver; aspartate aminotransferase from mammalian heart; in particular aspartate aminotransferase from pig heart; 4-amino-butyrate aminotransferase from mammalian liver, in particular 4-amino-butyrate aminotransferase from pig liver; 4-aminobutyrate aminotransferase from mammalian brain, in particular 4-aminobutyrate aminotransferase from human, pig, or rat brain; α-ketoadipate-glutamate aminotransferase from *Neurospora*, in particular α-ketoadipate:glutamate aminotransferase from *Neurospora crassa;* 4-amino-butyrate aminotransferase from *E. coli*, or α-aminoadipate aminotransferase from *Thermus*, in particular α-aminoadipate aminotransferase from *Thermus thermophilus*, and 5-aminovalerate aminotransferase from *Clostridium* in particular from *Clostridium aminovalericum*. A suitable 2-aminoadipate aminotransferase may e.g. be provided by *Pyrobaculum islandicum*.

In particular, the amino donor can be selected from the group of ammonia, ammonium ions, amines and amino acids. Suitable amines are primary amines and secondary amines. The amino acid may have a D- or L-configuration. Examples of amino donors are alanine, glutamate, isopropylamine, 2-aminobutane, 2-aminoheptane, phenylmethanamine, 1-phenyl-1-aminoethane, glutamine, tyrosine, phenylalanine, aspartate, β-aminoisobutyrate, β-alanine, 4-aminobutyrate, and α-aminoadipate.

In a further preferred embodiment, the method for preparing 6-ACA comprises a biocatalytic reaction in the presence of an enzyme capable of catalysing a reductive amination reaction in the presence of an ammonia source, selected from the group of oxidoreductases acting on the CH—$NH_2$ group of donors (EC 1.4), in particular from the group of amino acid dehydrogenases (E.C. 1.4.1). In general, a suitable amino acid dehydrogenase has 6-aminocaproic acid 6-dehydrogenase activity, catalysing the conversion of 5-FVA into 6-ACA or has α-aminopimelate 2-dehydrogenase activity, catalysing the conversion of AKP into AAP. In particular a suitable amino acid dehydrogenase be selected amongst the group of diaminopimelate dehydrogenases (EC 1.4.1.16), lysine 6-dehydrogenases (EC 1.4.1.18), glutamate dehydrogenases (EC 1.4.1.3; EC 1.4.1.4), and leucine dehydrogenases (EC 1.4.1.9).

In an embodiment, an amino acid dehydrogenase may be selected amongst an amino acid dehydrogenases classified as glutamate dehydrogenases acting with NAD or NADP as acceptor (EC 1.4.1.3), glutamate dehydrogenases acting with NADP as acceptor (EC 1.4.1.4), leucine dehydrogenases (EC 1.4.1.9), diaminopimelate dehydrogenases (EC 1.4.1.16), and lysine 6-dehydrogenases (EC 1.4.1.18).

An amino acid dehydrogenase may in particular originate from an organism selected from the group of *Corynebacterium*, in particular *Corynebacterium glutamicum*; *Proteus*, in particular *Proteus vulgaris*; *Agrobacterium*, in particular *Agrobacterium tumefaciens*; *Geobacillus*, in particular *Geobacillus stearothermophilus*; *Acinetobacter*, in particular *Acinetobacter* sp. ADP1; *Ralstonia*, in particular *Ralstonia solanacearum*; *Salmonella*, in particular *Salmonella typhimurium*; *Saccharomyces*, in particular *Saccharomyces cerevisiae*; *Brevibacterium*, in particular *Brevibacterium flavum*; and *Bacillus*, in particular *Bacillus sphaericus*, *Bacillus cereus* or *Bacillus subtilis*. For instance a suitable amino acid dehydrogenase may be selected amongst diaminopimelate dehydrogenases from *Bacillus*, in particular *Bacillus sphaericus*; diaminopimelate dehydrogenases from *Brevibacterium* sp.; diaminopimelate dehydrogenases from *Corynebacterium*, in particular diaminopimelate dehydrogenases from *Corynebacterium glutamicum*; diaminopimelate dehydrogenases from *Proteus*, in particular diaminopimelate dehydrogenase from *Proteus vulgaris*; lysine 6-dehydrogenases from *Agrobacterium*, in particular *Agrobacterium tumefaciens*, lysine 6-dehydrogenases from *Geobacillus*, in particular from *Geobacillus stearothermophilus*; glutamate dehydrogenases acting with NADH or NADPH as cofactor (EC 1.4.1.3) from *Acinetobacter*, in particular glutamate dehydrogenases from *Acinetobacter* sp. ADP1; glutamate dehydrogenases (EC 1.4.1.3) from *Ralstonia*, in particular glutamate dehydrogenases from *Ralstonia solanacearum*; glutamate dehydrogenases acting with NADPH as cofactor (EC 1.4.1.4) from *Salmonella*, in particular glutamate dehydrogenases from *Salmonella typhimurium*; glutamate dehydrogenases (EC 1.4.1.4) from *Saccharomyces*, in particular glutamate dehydrogenases from *Saccharomyces cerevisiae*; glutamate dehydrogenases (EC 1.4.1.4) from *Brevibacterium*, in particular glutamate dehydrogenases from *Brevibacterium flavum*; and leucine dehydrogenases from *Bacillus*, in particular leucine dehydrogenases from *Bacillus cereus* or *Bacillus subtilis*.

In a specific embodiment, AKP is biocatalytically converted into 5-formylpentanoate (5-FVA) in the presence of a decarboxylase or other biocatalyst catalysing such conversion. A decarboxylase used in accordance with the invention may in particular be selected from the group of α-keto acid decarboxylases from *Lactococcus lactis*, *Lactococcus lactis* var. *maltigenes* or *Lactococcus lactis* subsp. *cremoris*; branched chain α-keto acid decarboxylases from *Lactococcus lactis* strain B1157 or *Lactococcus lactis* IFPL730; pyruvate decarboxylases from *Saccharomyces cerevisiae*, *Candida flareri*, *Zymomonas mobilis*, *Hansenula* sp., *Rhizopus javanicus*, *Neurospora crassa*, or *Kluyveromyces marxianus*; α-ketoglutarate decarboxylases from *Mycobacterium tuberculosis*; glutamate decarboxylases from *E. coli*, *Lactobacillus brevis*, *Mycobacterium leprae*, *Neurospora crassa* or *Clostridium perfringens*; and aspartate decarboxylases from *E. coli*.

In particular, a decarboxylase from *Escherichia coli*, *Zymomonas mobilis*, *Saccharomyces cerevisiae*, *Mycobacterium tuberculosis*, *Pseudomonas* species, or *Lactococcus lactis* has been found suitable to catalyse the conversion of AKP into 5-FVA. More in particular, a biocatalyst comprising a decarboxylase having a amino acid sequence as identified by Sequence ID 31, Sequence ID 34, Sequence ID 37, Sequence ID 40, Sequence ID 43, Sequence ID 46 or a homologue thereof may be used. It is also envisaged that such decarboxylase may be used to prepare 6-ACA from AAP.

Thereafter 5-FVA is converted into 6-ACA. This can be done chemically: 6-ACA can be prepared in high yield by reductive amination of 5-FVA with ammonia over a hydrogenation catalyst, for example Ni on $SiO_2/Al_2O_3$ support, as described for 9-aminononanoic acid (9-aminopelargonic acid) and 12-aminododecanoic acid (12-aminolauric acid) in EP-A 628 535 or DE 4 322 065.

Alternatively, 6-ACA can be obtained by hydrogenation over $PtO_2$ of 6-oximocaproic acid, prepared by reaction of 5-FVA and hydroxylamine. (see e.g. F. O. Ayorinde, E. Y. Nana, P. D. Nicely, A. S. Woods, E. O. Price, C. P. Nwaonicha *J. Am. Oil Chem. Soc.* 1997, 74, 531-538 for synthesis of the homologous 12-aminododecanoic acid).

In an embodiment, the conversion of 5-FVA to 6-ACA is performed biocatalytically in the presence of (i) an amino donor and (ii) an aminotransferase, an amino acid dehydrogenase or another biocatalyst capable of catalysing such conversion. In particular in such an embodiment the aminotransferase may be selected from the group of aminotransferases from *Vibrio fluvialis*, *Pseudomonas aeruginosa*, *Bacillus subtilis*, *Bacillus weihenstephanensis* or *Escherichia coli*; β-aminoisobutyrate:α-ketoglutarate aminotransferase from hog kidney; β-alanine aminotransferase from rabbit liver; aminotransferase from shoots from *Mercurialis perennis*; 4-aminobutyrate aminotransferase from pig liver or from human, rat, or pig brain; β-alanine aminotransferase from rabbit liver; and L-lysine:α-ketoglutarate-ϵ-aminotransferase. In case an amino acid dehydrogenase is used, such amino acid dehydrogenase may in particular be selected from the group of lysine 6-dehydrogenases from *Agrobacterium tumefaciens* or *Geobacillus stearothermophilus*. Another suitable amino acid dehydrogenase may be selected from the group of diaminopimelate dehydrogenases from *Bacillus sphaericus*, *Brevibacterium* sp., *Corynebacterium glutamicum*, or *Proteus vulgaris*; from the group of glutamate dehydrogenases acting with NADH or NADPH as cofactor (EC 1.4.1.3) from *Acinetobacter* sp. ADP1 or *Ralstonia solanacearum*; from the group of glutamate dehydrogenases acting with NADPH as cofactor (EC 1.4.1.4) from *Salmonella typhimurium*; from the group of glutamate dehydrogenases (EC 1.4.1.4) from *Saccharomyces cerevisiae* or *Brevibacterium flavum*; or from the group of leucine dehydrogenases from *Bacillus cereus* or *Bacillus subtilis*.

In a specific embodiment, the conversion of 5-FVA to 6-ACA is catalysed by a biocatalyst comprising an aminotransferase comprising an amino acid sequence according to Sequence ID 2, Sequence ID 5, Sequence ID 8, Sequence ID 65, Sequence ID 67, Sequence ID 69 or a homologue of any of these sequences.

In a specific embodiment, AKP is chemically converted into 5-FVA. Efficient chemical decarboxylation of a 2-keto carboxylic acid into the corresponding aldehyde can be performed by intermediate enamine formation using a secondary amine, for instance morpholine, under azeotropic water removal and simultaneous loss of $CO_2$, e.g. based on a method as described in Tetrahedron Lett. 1982, 23(4), 459-462. The intermediate terminal enamide is subsequently hydrolysed to the corresponding aldehyde. 5-FVA may thereafter be biocatalytically converted into 6-ACA by transamination in the presence of an aminotransferase or by enzymatic reductive amination by an amino acid dehydrogenase or another biocatalyst able of catalysing such conversion. Such aminotransferase or amino acid dehydrogenase may in particular be selected from the biocatalysts mentioned above when describing the conversion of 5-FVA to 6-ACA.

Alternatively, the conversion of 5-FVA to 6-ACA may be performed by a chemical method, e.g. as mentioned above.

In a specific embodiment, AKP is biocatalytically converted into AAP in the presence of (i) an aminotransferase, an amino acid dehydrogenase, or another biocatalyst capable of catalysing such conversion and (ii) an amino donor. Such aminotransferase used in accordance with the invention for the conversion of AKP to AAP may in particular be selected from aminotransferases mentioned above, more in particular from the group of aspartate aminotransferases from pig heart; α-ketoadipate:glutamate aminotransferases from *Neurospora crassa* or yeast; aminotransferases from shoots from *Mercurialis perennis*; 4-aminobutyrate aminotransferases from *E. coli*; α-aminoadipate aminotransferases from *Thermus thermophilus*; aminotransferases from *Asplenium septentrionale* or *Asplenium unilaterale*; and aminotransferases from *Ceratonia siliqua*.

In a preferred embodiment, the aminotransferase for the conversion of AKP to AAP is selected from the group of aminotransferases from *Vibrio*, *Pseudomonas*, *Bacillus*, *Legionella*, *Nitrosomonas*, *Neisseria*, *Rhodobacter*, *Escherichia* and *Rhodopseudomonas*.

In particular, aminotransferases from an organism selected from the group of *Bacillus subtilis*, *Rhodobacter sphaeroides*, *Legionella pneumophila*, *Nitrosomonas europaea*, *Neisseria gonorrhoeae*, *Pseudomonas syringae*, *Rhodopseudomonas palustris*, *Vibrio fluvialis*, *Escherichia coli* and *Pseudomonas aeruginosa*, have been found suitable to catalyse the conversion of AKP to AAP.

In a specific embodiment, for the conversion of AKP to AAP an aminotransferase is used comprising an amino acid sequence according to Sequence ID 2, Sequence ID 8, Sequence ID 12, Sequence ID 15, Sequence ID 17, Sequence ID 19, Sequence ID 21, Sequence ID 23, Sequence ID 25, Sequence ID 27, Sequence ID 29 or a homologue of any of these sequences.

In a further embodiment, the method for preparing AAP comprises a biocatalytic reaction in the presence of an enzyme capable of catalysing a reductive amination reaction in the presence of an ammonia source, selected from the group of oxidoreductases acting on the CH—$NH_2$ group of donors (EC 1.4), in particular from the group of amino acid dehydrogenases (E.C. 1.4.1). In general, a suitable amino acid dehydrogenase has α-aminopimelate 2-dehydrogenase activity, catalysing the conversion of AKP into AAP.

In particular a suitable amino acid dehydrogenase may be selected from the group of diaminopimelate dehydrogenases (EC 1.4.1.16), glutamate dehydrogenases (EC 1.4.1.3; EC 1.4.1.4), and leucine dehydrogenases (EC 1.4.1.9).

In an embodiment, an amino acid dehydrogenase is selected amongst amino acid dehydrogenases classified as glutamate dehydrogenases acting with NAD or NADP as acceptor (EC 1.4.1.3), glutamate dehydrogenases acting with NADP as acceptor (EC 1.4.1.4), leucine dehydrogenases (EC 1.4.1.9), and diaminopimelate dehydrogenases (EC 1.4.1.16).

An amino acid dehydrogenase may in particular originate from an organism selected from the group of *Corynebacterium*, in particular *Corynebacterium glutamicum*; *Proteus*, in particular *Proteus vulgaris*; *Agrobacterium*, in particular *Agrobacterium tumefaciens*; *Geobacillus*, in particular *Geobacillus stearothermophilus*; *Acinetobacter*, in particular *Acinetobacter* sp. ADP1; *Ralstonia*, in particular *Ralstonia solanacearum*; *Salmonella*, in particular *Salmonella typhimurium*; *Saccharomyces*, in particular *Saccharomyces cerevisiae*; *Brevibacterium*, in particular *Brevibacterium flavum*; and *Bacillus*, in particular *Bacillus sphaericus*, *Bacillus cereus* or *Bacillus subtilis*.

For instance a suitable amino acid dehydrogenase may be selected amongst diaminopimelate dehydrogenases from *Bacillus*, in particular *Bacillus sphaericus*; diaminopimelate dehydrogenases from *Brevibacterium* sp.; diaminopimelate dehydrogenases from *Corynebacterium*, in particular diaminopimelate dehydrogenases from *Corynebacterium glutamicum*; diaminopimelate dehydrogenases from *Proteus*, in particular diaminopimelate dehydrogenase from *Proteus vulgaris*; glutamate dehydrogenases acting with NADH or NADPH as cofactor (EC 1.4.1.3) from *Acinetobacter*, in particular glutamate dehydrogenases from *Acinetobacter* sp. ADP1; glutamate dehydrogenases (EC 1.4.1.3) from *Ralstonia*, in particular glutamate dehydrogenases from *Ralstonia solanacearum*; glutamate dehydrogenases acting with NADPH as cofactor (EC 1.4.1.4) from *Salmonella*, in particular glutamate dehydrogenases from *Salmonella typhimurium*; glutamate dehydrogenases (EC 1.4.1.4) from *Saccharomyces*, in particular glutamate dehydrogenases from *Saccharomyces cerevisiae*; glutamate dehydrogenases (EC 1.4.1.4) from *Brevibacterium*, in particular glutamate dehydrogenases from *Brevibacterium flavum*; and leucine dehydrogenases from *Bacillus*, in particular leucine dehydrogenases from *Bacillus cereus* or *Bacillus subtilis*.

Another suitable amino acid dehydrogenase may be selected from the group of lysine 6-dehydrogenases from *Agrobacterium tumefaciens* or *Geobacillus stearothermophilus*; or from the group of leucine dehydrogenases from *Bacillus cereus* or *Bacillus subtilis*.

AAP prepared in a method of the invention may further be used for the preparation of 6-ACA. The inventors have realised that AAP, prepared from AKP, can be converted into 6-ACA by a decarboxylation reaction. This can be performed chemically, for instance by heating in a high boiling solvent in the presence of a ketone or aldehyde catalyst. For example, amino acids are decarboxylated in good yields in cyclohexanol at 150-160° C. with 1-2 v/v % of cyclohexenone as described by M. Hashimoto, Y. Eda, Y. Osanai, T. Iwai and S. Aoki in *Chem. Lett.* 1986, 893-896. Similar methods are described in Eur. Pat. Appl. 1586553, 2005 by Daiso, and by S. D. Brandt, D. Mansell, S. Freeman, I. A. Fleet, J. F. Alder *J. Pharm. Biomed. Anal.* 2006, 41, 872-882.

Alternatively, the decarboxylation of AAP to 6-ACA may be performed biocatalytically in the presence of a decarboxylase or other biocatalyst catalysing such decarboxylation.

The decarboxylase may be selected amongst decarboxylases capable of catalysing the decarboxylation of an α-amino acid. An enzyme capable of decarboxylating an alpha-amino acid may in particular be selected from the group of decarboxylases (E.C. 4.1.1), preferably from the group of pyruvate decarboxylases (EC 4.1.1.1), diaminopimelate decarboxylases (EC 4.1.1.20), diaminopimelate decarboxylases (EC 4.1.1.20), branched chain alpha-keto acid decarboxylases (EC 4.1.1.72), which include alpha-ketoisovalerate decarboxylases, and alpha-ketoglutarate decarboxylases (EC 4.1.1.71).

One or more other suitable decarboxylases may in particular be selected amongst the group of oxalate decarboxylases (EC 4.1.1.2), oxaloacetate decarboxylases (EC 4.1.1.3), acetoacetate decarboxylases (EC 4.1.1.4), aspartate 1-decarboxylases (EC 4.1.1.11), valine decarboxylases/leucine decarboxylases (EC 4.1.1.14), glutamate decarboxylases (EC 4.1.1.15), 3-hydroxyglutamate decarboxylases (EC 4.1.1.16), ornithine decarboxylases (EC 4.1.1.17), lysine decarboxylases (EC 4.1.1.18), arginine decarboxylases (EC 4.1.1.19), 2-oxoglutarate decarboxylases (EC 4.1.1.71), and diaminobutyrate decarboxylases (EC 4.1.1.86).

A decarboxylase may in particular be a decarboxylase of an organism selected from the group of squashes, e.g. *Curcurbita moschata*; cucumbers; yeasts; fungi, e.g. *Saccharomyces cerevisiae, Candida flareri, Hansenula* sp., *Kluyveromyces marxianus, Rhizopus javanicus*, and *Neurospora crassa*; mammals, in particular from mammalian brain; and bacteria such as *Escherichia coli, Lactococcus lactis, Mycobacterium tuberculosis, Pseudomonas* sp. and *Zymomonas mobilis*.

The pyruvate decarboxylase may originate from *Saccharomyces cerevisiae* or *Zymomonas mobilis*. In particular, pyruvate decarboxylase mutant I472A from *Zymomonas mobilis* may be used. An oxaloacetate decarboxylase from *Pseudomonas* may in particular be used. Glutamate decarboxylase or aspartate decarboxylase from *Escherichia coli* (*E. coli*) may be used, or glutamate decarboxylase from *Neurospora crassa, Mycobacterium leprae, Clostridium perfringens, Lactobacillus brevis, Mycobacterium tuberculosis, Streptococcus* or *Lactococcus* may be used. Examples of *Lactococcus* species from which the glutamate decarboxylase may originate in particular include *Lactococcus lactis*, such as *Lactococcus lactis* strain B1157, *Lactococcus lactis* IFPL730, more in particular *Lactococcus lactis* var. *maltigenes* (formerly named *Streptococcus lactis* var. *maltigenes*). A diaminopimelate decarboxylase may, e.g., be from an organism capable of synthesising lysine from diaminopimelate. Such organism may in particular be found amongst bacteria, archaea and plants. In particular, the diaminopimelate decarboxylase may be from a gram negative bacterium, for instance *E. coli*. Branched-chain alpha-keto acid decarboxylases from *Lactococcus lactis* may be used. More in particular, branched chain alpha-keto acid decarboxylases and alpha-ketoisovalerate decarboxylases from *Lactococcus lactis* may be used.

An alpha-ketoglutarate decarboxylase from *Mycobacterium tuberculosis* may in particular be used. The inventors have found that alpha-ketoglutarate decarboxylase (Kgd) from *Mycobacterium tuberculosis* may be used for converting AAP into 6-ACA. In particular, the inventors have found that such decarboxylase comprising a sequence as shown in SEQUENCE ID No. 46 or a functional analogue thereof may be capable of catalysing the formation of 6-ACA from AAP.

A glutamate decarboxylase may in particular be selected from *Curcurbita moschata*, cucumber, yeast, or calf brain; and diaminopimelate decarboxylases (EC 4.1.1.20).

A diaminopimelate decarboxylase may, e.g., be from an organism capable of synthesising lysine from diaminopimelate. Such organism may in particular be found amongst bacteria, archaea and plants.

In particular, the diaminopimelate decarboxylase may be from a gram negative bacterium, for instance *E. coli*.

In a specific embodiment, AKP is chemically converted into AAP. AAP can be prepared from 2-oxopimelic acid by catalytic Leuckart-Wallach reaction as described for similar compounds. This reaction is performed with ammonium formate in methanol and [RhCp*Cl$_2$]$_2$ as homogeneous catalyst (M. Kitamura, D. Lee, S. Hayashi, S. Tanaka, M. Yoshimura *J. Org. Chem.* 2002, 67, 8685-8687). Alternatively, the Leuckart-Wallach reaction can be performed with aqueous ammonium formate using [Ir$^{III}$Cp*(bpy)H$_2$O]SO$_4$ as catalyst as described by S. Ogo, K. Uehara and S. Fukuzumi in *J. Am. Chem. Soc.* 2004, 126, 3020-3021. Transformation of α-keto acids into (enantiomerically enriched) amino acids is also possible by reaction with (chiral) benzylamines and subsequent hydrogenation of the intermediate imine over Pd/C or Pd(OH)$_2$/C. See for example, R. G. Hiskey, R. C. Northrop *J. Am. Chem. Soc.* 1961, 83, 4798.

Thereafter AAP is biocatalytically converted into 6-ACA, in the presence of a decarboxylase or another biocatalyst capable of performing such decarboxylation. Such decarboxylase may in particular be selected amongst the biocatalysts referred to above, when describing biocatalysts for the conversion of AAP to 6-ACA.

Alternatively, the conversion of AAP to 6-ACA may be performed by a chemical method, e.g. as mentioned above.

In a specific embodiment, AKP is biocatalytically converted into 5-FVA in the presence of a decarboxylase or other biocatalyst capable of catalysing such conversion and 5-FVA is thereafter converted into 6-ACA in the presence of an aminotransferase, amino acid dehydrogenase, or other biocatalyst capable of catalysing such conversion. Decarboxylases suitable for these reactions may in particular be selected from the group of decarboxylases mentioned above, when describing the biocatalytic conversion of AKP into 5-FVA. A suitable aminotransferase or amino acid dehydrogenase for the conversion of 5-FVA may in particular be selected from those mentioned above, when describing the biocatalytic conversion of 5-FVA to 6-ACA.

In a specific embodiment, AKP is biocatalytically converted into AAP in the presence of an aminotransferase, amino acid dehydrogenase, or other biocatalyst capable of catalysing such conversion and AAP is thereafter converted into 6-ACA in the presence of a decarboxylase or other biocatalyst capable of catalysing such conversion.

Enzymes suitable for these reactions may in particular be selected from the group of aminotransferases, amino acid dehydrogenases, and decarboxylases which have been described above when describing the biocatalytic conversion of AKP into AAP and the biocatalytic conversion of AAP into 6-ACA respectively.

AKP used to prepare 6-ACA may in principle be obtained in any way. For instance, AKP may be obtained based on a method as described by H. Jäger et al. Chem. Ber. 1959, 92, 2492-2499. AKP can be prepared by alkylating cyclopentanone with diethyl oxalate using sodium ethoxide as a base, refluxing the resultant product in a strong acid (2 M HCl) and recovering the product, e.g. by crystallisation from toluene.

It is also possible to obtain AKP from a natural source, e.g. from methanogenic Archaea, from *Asplenium septentrionale*, or from *Hydnocarpus anthelminthica*. AKP may for instance be extracted from such organism, or a part thereof, e.g. from *Hydnocarpus anthelminthica* seeds. A suitable extraction method may e.g. be based on the method described in A. I. Virtanen and A. M. Berg in Acta Chemica Scandinavica 1954, 6, 1085-1086, wherein the extraction of amino acids and AKP from *Asplenium*, using 70% ethanol, is described.

In a specific embodiment, AKP is prepared in a method comprising converting alpha-ketoglutaric acid (AKG) into alpha-ketoadipic acid (AKA) and converting alpha-ketoadipic acid into alpha-ketopimelic acid. This reaction may be catalysed by a biocatalyst. AKG may, e.g., be prepared biocatalytically from a carbon source, such as a carbohydrate, in a manner known in the art per se.

A suitable biocatalyst for preparing AKP from AKG may in particular be selected amongst biocatalysts catalysing $C_1$-elongation of alpha-ketoglutaric acid into alpha-ketoadipic acid and/or $C_1$-elongation of alpha-ketoadipic acid into alpha-ketopimelic acid.

In a specific embodiment, the preparation of AKP is catalysed by a biocatalyst comprising
 a. an AksA enzyme or an homologue thereof;
 b. at least one enzyme selected from the group of AksD enzymes, AksE enzymes, homologues of AksD enzymes and homologues of AksE enzymes; and
 c. an AksF enzyme or a homologue thereof.

One or more of the AksA, AksD, AksE, AksF enzymes or homologues thereof may be found in an organism selected from the group of methanogenic archaea, preferably selected from the group of *Methanococcus, Methanocaldococcus, Methanosarcina, Methanothermobacter, Methanosphaera, Methanopyrus* and *Methanobrevibacter*.

In a specific embodiment, the biocatalyst catalysing the preparation of AKP from alpha-ketoglutaric acid (AKG) comprises an enzyme system catalysing the conversion of alpha-ketoglutaric acid into alpha-ketoadipic acid, wherein said enzyme system forms part of the alpha-amino adipate pathway for lysine biosynthesis. The term 'enzyme system' is in particular used herein for a single enzyme or a group of enzymes whereby a specific conversion can be catalysed.

The preparation of AKP from AKG may comprise one or more biocatalytic reactions with known or unknown intermediates e.g. the conversion of AKG into AKA or the conversion of AKA into AKP. Such system may be present inside a cell or isolated from a cell. The enzyme system may in particular be from an organism selected from the group of yeasts, fungi, archaea and bacteria, in particular from the group of *Penicillium, Cephalosporium, Paelicomyces, Trichophytum, Aspergillus, Phanerochaete, Emericella, Ustilago, Schizosaccharomyces, Saccharomyces, Candida, Yarrowia, Pichia, Kluyveromyces, Thermus, Deinococcus, Pyrococcus, Sulfolobus, Thermococcus, Methanococcus, Methanocaldococcus, Methanosphaera, Methanopyrus, Methanobrevibacter, Methanosarcina* and *Methanothermobacter*.

In a specific embodiment, the biocatalyst catalysing the preparation of AKP from alpha-ketoglutaric acid comprises an enzyme system catalysing the conversion of alpha-ketoglutaric acid into alpha-ketoadipic acid, wherein at least one of the enzymes of the enzyme system originates from nitrogen fixing bacteria selected from the group of cyanobacteria, rhizobiales, γ-proteobacteria and actinobacteria, in particular from the group of *Anabaena, Microcystis, Synechocystis, Rhizobium, Bradyrhizobium, Pseudomonas, Azotobacter, Klebsiella* and *Frankia*.

Examples of homologues for these Aks enzymes and the genes encoding these enzymes are given in the Tables 1A and 1B on the following pages.

TABLE 1A

| Enzyme name | Organism | gene | Protein |
|---|---|---|---|
| AksA | *Methanocaldococcus jannashii* | MJ0503 | NP_247479 |
| | *Methanothermobacter thermoautotropicum* ΔH | MTH1630 | NP_276742 |
| | *Methanococcus maripaludis* S2 | MMP0153 | NP_987273 |
| | *Methanococcus maripaludis* C5 | MmarC5_1522 | YP_001098033 |
| | *Methanococcus maripaludis* C7 | MmarC7_1153 | YP_001330370 |
| | *Methanosphaera stadtmanae* DSM 3091 | Msp_0199 | YP_447259 |
| | *Methanopyrus kandleri* AV19 | MK1209 | NP_614492 |
| | *Methanobrevibacter smithii* ATCC35061 | Msm_0722 | YP_001273295 |
| | *Methanococcus vannielii* SB | Mevan_1158 | YP_001323668 |
| | *Methanococcus aeolicus* Nankai 3 | Maeo_0994 | YP_001325184 |
| AksD | *Methanocaldococcus jannashii* | MJ1003 | NP_247997 |
| | *Methanothermobacter thermoautotropicum* ΔH | MTH1386 | NP_276502 |
| | *Methanococcus maripaludis* S2 | Mmp1480 | NP_988600 |
| | *Methanococcus maripaludis* C5 | MmarC5_0098 | YP_001096630 |
| | *Methanococcus maripaludis* C7 | MmarC7_0724 | YP_001329942 |
| | *Methanosphaera stadtmanae* DSM 3091 | Msp_1486 | YP_448499 |
| | *Methanopyrus kandleri* AV19 | MK1440 | NP_614723 |
| | *Methanobrevibacter smithii* ATCC35061 | Msm_0723 | YP_001273296 |
| | *Methanococcus vannielii* SB | Mevan_0789 | YP_001323307 |
| | *Methanococcus aeolicus* Nankai 3 | Maeo_0311 | YP_001324511 |

References to gene and protein can be found via URL: ncbi[dot]nlm[dot]nih[dot]gov[slash], (as available on 15 Apr. 2008)

TABLE 1B

| Enzyme name | Organism | gene | Protein |
|---|---|---|---|
| AksE | Methanocaldococcus jannashii | MJ1271 | NP_248267 |
| | Methanothermobacter thermoautotropicum ΔH | MTH1387 | NP_276503 |
| | Methanococcus maripaludis S2 | MMP0381 | NP_987501 |
| | Methanococcus maripaludis C5 | MmarC5_1257 | YP_001097769 |
| | Methanococcus maripaludis C7 | MmarC7_1379 | YP_001330593 |
| | Methanosphaera stadtmanae DSM 3091 | Msp_1485 | YP_448498 |
| | Methanopyrus kandleri AV19 | MK0781 | NP_614065 |
| | Methanobrevibacter smithii ATCC35061 | Msm_0847 | YP_001273420 |
| | Methanococcus vannielii SB | Mevan_1368 | YP_001323877 |
| | Methanococcus aeolicus Nankai 3 | Maeo_0652 | YP_001324848 |
| AksF | Methanocaldococcus jannashii | MJ1596 | NP_248605 |
| | Methanothermobacter thermoautotropicum ΔH | MTH184 | NP_275327 |
| | Methanococcus maripaludis S2 | MMP0880 | NP988000 |
| | Methanococcus maripaludis C5 | MmarC5_ 0688 | YP001097214 |
| | Methanococcus maripaludis C7 | MmarC7 _ 0128 | YP_001329349 |
| | Methanosphaera stadtmanae DSM 3091 | Msp_0674 | YP_447715 |
| | Methanopyrus kandleri AV19 | MK0782 | NP_614066 |
| | Methanobrevibacter smithii ATCC35061 | Msm_0373 | YP001272946 |
| | Methanococcus vannielii SB | Mevan_0040 | YP_001322567 |
| | Methanococcus aeolicus Nankai 3 | Maeo_1484 | YP_001325672 |

References to gene and protein can be found via URL: ncbi[dot]nlm[dot]nih[dot]gov[slash], (as available on 15 Apr. 2008

If desired, 6-ACA obtained in accordance with the invention can be cyclised to form caprolactam, e.g. as described in U.S. Pat. No. 6,194,572.

Reaction conditions for any biocatalytic step in the context of the present invention may be chosen depending upon known conditions for the biocatalyst, in particular the enzyme, the information disclosed herein and optionally some routine experimentation.

In principle, the pH of the reaction medium used may be chosen within wide limits, as long as the biocatalyst is active under the pH conditions. Alkaline, neutral or acidic conditions may be used, depending on the biocatalyst and other factors. In case the method includes the use of a micro-organism, e.g. for expressing an enzyme catalysing a method of the invention, the pH is selected such that the micro-organism is capable of performing its intended function or functions. The pH may in particular be chosen within the range of four pH units below neutral pH and two pH units above neutral pH, i.e. between pH 3 and pH 9 in case of an essentially aqueous system at 25° C. A system is considered aqueous if water is the only solvent or the predominant solvent (>50 wt. %, in particular >90 wt. %, based on total liquids), wherein e.g. a minor amount of alcohol or another solvent (<50 wt. %, in particular <10 wt. %, based on total liquids) may be dissolved (e.g. as a carbon source) in such a concentration that micro-organisms which may be present remain active. In particular in case a yeast and/or a fungus is used, acidic conditions may be preferred, in particular the pH may be in the range of pH 3 to pH 8, based on an essentially aqueous system at 25° C. If desired, the pH may be adjusted using an acid and/or a base or buffered with a suitable combination of an acid and a base.

In principle, the incubation conditions can be chosen within wide limits as long as the biocatalyst shows sufficient activity and/or growth. This includes aerobic, micro-aerobic, oxygen limited and anaerobic conditions.

Anaerobic conditions are herein defined as conditions without any oxygen or in which substantially no oxygen is consumed by the biocatalyst, in particular a micro-organism, and usually corresponds to an oxygen consumption of less than 5 mmol/l·h, in particular to an oxygen consumption of less than 2.5 mmol/l·h, or less than 1 mmol/l·h.

Aerobic conditions are conditions in which a sufficient level of oxygen for unrestricted growth is dissolved in the medium, able to support a rate of oxygen consumption of at least 10 mmol/l·h, more preferably more than 20 mmol/l·h, even more preferably more than 50 mmol/l·h, and most preferably more than 100 mmol/l·h.

Oxygen-limited conditions are defined as conditions in which the oxygen consumption is limited by the oxygen transfer from the gas to the liquid. The lower limit for oxygen-limited conditions is determined by the upper limit for anaerobic conditions, i.e. usually at least 1 mmol/l·h, and in particular at least 2.5 mmol/l·h, or at least 5 mmol/l·h. The upper limit for oxygen-limited conditions is determined by the lower limit for aerobic conditions, i.e. less than 100 mmol/l·h, less than 50 mmol/l·h, less than 20 mmol/l·h, or less than to 10 mmol/l·h.

Whether conditions are aerobic, anaerobic or oxygen limited is dependent on the conditions under which the method is carried out, in particular by the amount and composition of ingoing gas flow, the actual mixing/mass transfer properties of the equipment used, the type of micro-organism used and the micro-organism density.

In principle, the temperature used is not critical, as long as the biocatalyst, in particular the enzyme, shows substantial activity. Generally, the temperature may be at least 0° C., in particular at least 15° C., more in particular at least 20° C. A desired maximum temperature depends upon the biocatalyst. In general such maximum temperature is known in the art, e.g. indicated in a product data sheet in case of a commercially available biocatalyst, or can be determined routinely based on common general knowledge and the information disclosed herein. The temperature is usually 90° C. or less, preferably 70° C. or less, in particular 50° C. or less, more in particular or 40° C. or less.

In particular if a biocatalytic reaction is performed outside a host organism, a reaction medium comprising an organic solvent may be used in a high concentration (e.g. more than 50%, or more than 90 wt. %), in case an enzyme is used that retains sufficient activity in such a medium.

In an advantageous method 6-ACA is prepared making use of a whole cell biotransformation of the substrate for 6-ACA or an intermediate for forming 6-ACA (AKP, AAP or 5-FVA), comprising a micro-organism wherein one or more biocatalysts (usually one or more enzymes) catalysing the biotransformation are produced, such as one or more biocatalysts selected from the group of biocatalysts capable of catalysing the conversion of AKP to AAP, biocatalysts capable of catalysing the conversion of AAP to 6-ACA, biocatalysts capable of catalysing the conversion of AKP to 5-FVA and biocatalysts capable of catalysing the conversion of 5-FVA to G-ACA. In a preferred embodiment the microorganism is capable of producing a decarboxylase and/or at least one enzyme selected from amino acid dehydrogenases and aminotransferases are produced. capable of catalysing a reaction step as described above, and a carbon source for the micro-organism.

The carbon source may in particular contain at least one compound selected from the group of monohydric alcohols, polyhydric alcohols, carboxylic acids, carbon dioxide, fatty acids, glycerides, including mixtures comprising any of said compounds. Suitable monohydric alcohols include methanol and ethanol, Suitable polyols include glycerol and carbohydrates. Suitable fatty acids or glycerides may in particular be provided in the form of an edible oil, preferably of plant origin.

In particular a carbohydrate may be used, because usually carbohydrates can be obtained in large amounts from a biologically renewable source, such as an agricultural product, preferably an agricultural waste-material. Preferably a carbohydrate is used selected from the group of glucose, fructose, sucrose, lactose, saccharose, starch, cellulose and hemi-cellulose. Particularly preferred are glucose, oligosaccharides comprising glucose and polysaccharides comprising glucose.

A cell, in particular a recombinant cell, comprising one or more biocatalysts (usually one or more enzymes) for catalysing a reaction step in a method of the invention can be constructed using molecular biological techniques, which are known in the art per se. For instance, if one or more biocatalysts are to be produced in a recombinant cell (which may be a heterologous system), such techniques can be used to provide a vector (such as a recombinant vector) which comprises one or more genes encoding one or more of said biocatalysts. One or more vectors may be used, each comprising one or more of such genes. Such vector can comprise one or more regulatory elements, e.g. one or more promoters, which may be operably linked to a gene encoding an biocatalyst.

As used herein, the term "operably linked" refers to a linkage of polynucleotide elements (or coding sequences or nucleic acid sequence) in a functional relationship. A nucleic acid sequence is "operably linked" when it is placed into a functional relationship with another nucleic acid sequence. For instance, a promoter or enhancer is operably linked to a coding sequence if it affects the transcription of the coding sequence.

As used herein, the term "promoter" refers to a nucleic acid fragment that functions to control the transcription of one or more genes, located upstream with respect to the direction of transcription of the transcription initiation site of the gene, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one of skilled in the art to act directly or indirectly to regulate the amount of transcription from the promoter. A "constitutive" promoter is a promoter that is active under most environmental and developmental conditions. An "inducible" promoter is a promoter that is active under environmental or developmental regulation. The term "homologous" when used to indicate the relation between a given (recombinant) nucleic acid or polypeptide molecule and a given host organism or host cell, is understood to mean that in nature the nucleic acid or polypeptide molecule is produced by a host cell or organisms of the same species, preferably of the same variety or strain.

The promoter that could be used to achieve the expression of the nucleic acid sequences coding for an enzyme for use in a method of the invention, in particular an aminotransferase, an amino acid dehydrogenase or a decarboxylase, such as described herein above may be native to the nucleic acid sequence coding for the enzyme to be expressed, or may be heterologous to the nucleic acid sequence (coding sequence) to which it is operably linked. Preferably, the promoter is homologous, i.e. endogenous to the host cell.

If a heterologous promoter (to the nucleic acid sequence encoding for the enzyme of interest) is used, the heterologous promoter is preferably capable of producing a higher steady state level of the transcript comprising the coding sequence (or is capable of producing more transcript molecules, i.e. mRNA molecules, per unit of time) than is the promoter that is native to the coding sequence. Suitable promoters in this context include both constitutive and inducible natural promoters as well as engineered promoters, which are well known to the person skilled in the art.

A "strong constitutive promoter" is one which causes mRNAs to be initiated at high frequency compared to a native host cell. Examples of such strong constitutive promoters in Gram-positive micro-organisms include SP01-26, SP01-15, veg, pyc (pyruvate carboxylase promoter), and amyE.

Examples of inducible promoters in Gram-positive micro-organisms include, the IPTG inducible Pspac promoter, the xylose inducible PxylA promoter.

Examples of constitutive and inducible promoters in Gram-negative microorganisms include, but are not limited to, tac, tet, trp-tet, lpp, lac, lpp-lac, laclq, T7, T5, T3, gal, trc, ara ($P_{BAD}$), SP6, $\lambda$-$P_R$, and $\lambda$-$P_L$.

Promoters for (filamentous) fungal cells are known in the art and can be, for example, the glucose-6-phosphate dehydrogenase gpdA promoters, protease promoters such as pepA, pepB, pepC, the glucoamylase glaA promoters, amylase amyA, amyB promoters, the catalase catR or catA promoters, glucose oxidase goxC promoter, beta-galactosidase lacA promoter, alpha-glucosidase aglA promoter, translation elongation factor tefA promoter, xylanase promoters such as xlnA, xlnB, xlnC, xlnD, cellulase promoters such as eglA, eglB, cbhA, promoters of transcriptional regulators such as areA, creA, xlnR, pacC, prtT, or another promotor, and can be found among others at the NCBI website (URL: ncbi[dot]nlm[dot]nih[dot]gov[slash]entrez[slash]).

The term "heterologous" when used with respect to a nucleic acid (DNA or RNA) or protein refers to a nucleic acid or protein that does not occur naturally as part of the organism, cell, genome or DNA or RNA sequence in which it is present, or that is found in a cell or location or locations in the genome or DNA or RNA sequence that differ from that in which it is found in nature. Heterologous nucleic acids or proteins are not endogenous to the cell into which it is introduced, but has been obtained from another cell or synthetically or recombinantly produced. Generally, though not necessarily, such nucleic acids encode proteins that are not normally produced by the cell in which the DNA is transcribed or expressed. Similarly exogenous RNA encodes for proteins not normally expressed in the cell in which the exogenous RNA is present. Heterologous nucleic acids and proteins may also be referred to as foreign nucleic acids or proteins. Any nucleic acid or protein that one of skill in the art would recognize as heterologous or foreign to the cell in which it is expressed is herein encompassed by the term heterologous nucleic acid or protein.

A method according to the invention may be carried out in a host organism, which may be novel.

Accordingly, the invention also relates to a host cell comprising one or more biocatalysts capable of catalysing at least one reaction step in a method of the invention, in particular capable of catalysing at least one reaction step in the conversion of AKP, AAP or 5-FVA to 6-ACA. The invention also relates to a novel vector comprising one or more genes encoding for one or more enzymes capable of catalysing at least one reaction step in a method of the invention, in particular capable of catalysing at least one reaction step in the conversion of AKP to 6-ACA and to a novel host cell comprising one or more genes encoding for one or more enzymes capable of catalysing at least one reaction step in a method of the invention, in particular capable of catalysing at least one reaction step in the conversion of AKP to 6-ACA (which one or more genes may form part of one or more vectors).

In a specific embodiment, a host cell according to the invention is a recombinant cell comprising a nucleic acid sequence encoding a biocatalyst capable of catalysing a transamination reaction or a reductive amination reaction to form alpha-aminopimelic acid from alpha-ketopimelic acid. Said sequence may be part of a vector or may have been inserted into the chromosomal DNA.

In particular, a host cell or vector according to the invention may comprise at least one nucleic acid sequence, in particular at least two nucleic acid sequences, selected from the group of nucleic acid sequences encoding an enzyme with α-ketopimelic acid decarboxylase activity, nucleic acid sequences encoding an enzyme with 5-formylpentanoate aminotransferase activity, nucleic acid sequences encoding an enzyme with α-ketopimelic acid aminotransferase activity, nucleic acid sequences encoding an enzyme with α-ketopimelic acid dehydrogenase activity and nucleic acid sequences encoding an enzyme with α-aminopimelic acid decarboxylase activity. Of these sequences, typically one or more, in particular two or more, are recombinant sequences.

In preferred embodiment the host cell, typically a recombinant host cell, or the vector according to the invention comprises a nucleic acid sequence encoding at least one biocatalyst having α-ketopimelic acid decarboxylase activity, and/or at least one nucleic acid sequence selected from sequences encoding a biocatalyst with 5-formylpentanoate aminotransferase activity.

In such an embodiment, the nucleic acid sequence encoding an enzyme with α-ketopimelic acid decarboxylase activity may in particular comprise an amino acid sequence according to Sequence ID 31, Sequence ID 34, Sequence ID 37, Sequence ID 40, Sequence ID 43 or Sequence ID 46 or a homologue of any of these sequences and/or the nucleic acid sequence encoding an enzyme with 5-formylpentanoate aminotransferase may in particular comprise an amino acid sequence according to Sequence ID 2, Sequence ID 5, Sequence ID 8, Sequence ID 65 Sequence ID 67, Sequence ID 69 or a homologue thereof. One or more of said nucleic acid sequences may form part of one or more recombinant vectors.

In a further preferred embodiment, the vector or host cell comprises a nucleic acid sequence encoding an enzyme with α-ketopimelic acid aminotransferase activity and/or a nucleic acid sequence encoding an enzyme with α-aminopimelic acid decarboxylase activity. The nucleic acid sequence encoding an enzyme with α-ketopimelic acid aminotransferase activity may in particular comprise an amino acid sequence according to Sequence ID 2, Sequence ID 8, Sequence ID 12, Sequence ID 15, Sequence ID 17, Sequence ID 19, Sequence ID 21, Sequence ID 23, Sequence ID 25, Sequence ID 27, Sequence ID 29, or a homologue thereof. One or more of said nucleic acid sequences may form part of one or more recombinant vectors.

In a specific preferred embodiment, a host cell according to the invention comprises a nucleic acid sequence encoding an enzyme with α-aminopimelate 2-dehydrogenase activity and a nucleic acid sequence encoding an enzyme with α-aminopimelate decarboxylase activity.

In a specific preferred embodiment, a host cell according to the invention comprises a nucleic acid sequence encoding an enzyme with 6-aminocaproic acid 6-dehydrogenase activity and a nucleic acid sequence encoding an enzyme with α-ketopimelic acid decarboxylase activity.

One or more suitable genes of a host cell or vectors according to the invention may in particular be selected amongst genes encoding an enzyme as mentioned herein above.

In a specific embodiment, the host cell is a recombinant cell comprising at least one nucleic acid sequence selected from the group of sequences as identified in any of Sequence ID 1, Sequence ID 3, Sequence ID 4, Sequence ID 6, Sequence ID 7, Sequence ID 11, Sequence ID 13, Sequence ID 14, Sequence ID 16, Sequence ID 18, Sequence ID 20, Sequence ID 22, Sequence ID 24, Sequence ID 26, Sequence ID 28, Sequence ID 30, Sequence ID 32, Sequence ID 33, Sequence ID 35, Sequence ID 36, Sequence ID 38, Sequence ID 39, Sequence ID 41, Sequence ID 42, Sequence ID 44, Sequence ID 45, Sequence ID 47, Sequence ID 64, Sequence ID 66, Sequence ID 68 and functional analogues thereof.

A nucleic acid sequence encoding an enzyme with 5-FVA aminotransferase activity, may in particular be a sequence selected from the group of sequences represented by any of the Sequence ID's 1, 3, 4, 6, 7, 64, 66, 68, and functional analogues of any of these sequences.

As used herein, the term "functional analogues" at least includes other sequences encoding an enzyme having the same amino acid sequence and other sequences encoding a homologue of such enzyme.

A nucleic acid sequence encoding an enzyme with AKP decarboxylase activity may in particular be a sequence selected from the group of sequences represented by any of the Sequence ID's 30, 32, 33, 35, 36, 38, 39, 41, 42, 44, 45, 47 and functional analogues of any of these sequences.

In a preferred embodiment, the host cell comprises a nucleic acid sequence encoding an enzyme, capable of catalysing the conversion of AAP to AKP, according to Sequence ID No.: 1, 3, 7, 11, 13, 14, 16, 18, 20, 22, 24, 26, 28, or a functional analogue thereof, which may be a wild type or non-wild type sequence In a specific embodiment, the host cell comprises at least one nucleic acid sequence encoding a biocatalyst having alpha-aminopimelic acid decarboxylase activity, which may be homologous or heterologous to the host cell. In particular such biocatalyst may be selected from the group of decarboxylases (E.C. 4.1.1), more in particular from the group of glutamate decarboxylases (EC 4.1.1.15), diaminopimelate decarboxylases (EC 4.1.1.20) aspartate 1-decarboxylases (EC 4.1.1.11), branched chain alpha-keto acid decarboxylases, alpha-ketoisovalerate decarboxylases, alpha-ketoglutarate decarboxylases, pyruvate decarboxylases (EC 4.1.1.1) and oxaloacetate decarboxylases (E.C. 4.1.1.3).

In a specific embodiment, the host cell comprises one or more enzymes catalysing the formation of AKP from AKG (see also above). Use may be made of an enzyme system forming part of the alpha-amino adipate pathway for lysine biosynthesis. The term 'enzyme system' is in particular used herein for a single enzyme or a group of enzymes whereby a specific conversion can be catalysed. Said conversion may comprise one or more chemical reactions with known or unknown intermediates e.g. the conversion of AKG into AKA or the conversion of AKA into AKP. Such system may be present inside a cell or isolated from a cell. It is known that aminotransferases often have a wide substrate range. If present, it may be desired to decrease activity of one or more such enzymes in a host cell such that activity in the conversion of AKA to alpha-aminoadipate (AAA) is reduced, whilst maintaining relevant catalytic functions for biosynthesis of other amino acids or cellular components. Also a host cell devoid of any other enzymatic activity resulting in the conversion of AKA to an undesired side product is preferred.

In a preferred host cell, suitable for preparing AAP making use of a whole cell biotransformation process, one or more biocatalysts capable of catalysing at least one reaction step in the preparation of alpha-ketopimelic acid from alpha-ketoglutaric acid are encoded for. Suitable biocatalysts are, e.g., as described above when discussing the preparation of AKP.

The host cell may for instance be selected from bacteria, yeasts or fungi. In particular the host cell may be selected from the genera selected from the group of *Aspergillus, Penicillium, Saccharomyces, Kluyveromyces, Pichia, Candida, Hansenula, Bacillus, Corynebacterium, Pseudomonas, Gluconobacter, Methanococcus, Methanobacterium, Methanocaldococcus* and *Methanosarcina* and *Escherichia*. Herein, usually one or more encoding nucleic acid sequences as mentioned above have been cloned and expressed.

In particular, the host strain and, thus, a host cell suitable for the biochemical synthesis of 6-ACA may be selected from the group of *Escherichia coli, Bacillus subtilis, Bacillus amyloliquefaciens, Corynebacterium glutamicum, Aspergillus niger, Penicillium chrysogenum, Saccharomyces cervisiae, Hansenula polymorpha, Candida albicans, Kluyveromyces lactis, Pichia stipitis, Pichia pastoris, Methanobacterium thermoautothrophicum* ΔH, *Methanococcus maripaludis, Methanococcus voltae, Methanosarcina acetivorans, Methanosarcina barkeri* and *Methanosarcina mazei* host cells. In a preferred embodiment, the host cell is capable of producing lysine (as a precursor).

The host cell may be in principle a naturally occurring organism or may be an engineered organism. Such an organism can be engineered using a mutation screening or metabolic engineering strategies known in the art. In a specific embodiment, the host cell naturally comprises (or is capable of producing) one or more of the enzymes suitable for catalysing a reaction step in a method of the invention, such as one or more activities selected from the group of decarboxylases, aminotransferases and amino acid dehydrogenases capable of catalysing a reaction step in a method of the invention. For instance *E. coli* may naturally be capable of producing an enzyme catalysing a transamination in a method of the invention. It is also possible to provide a recombinant host cell with both a recombinant gene encoding an aminotransferase or amino acid dehydrogenase capable of catalysing a reaction step in a method of the invention and a recombinant gene encoding a decarboxylase gene capable of catalysing a reaction step in a method of the invention.

For instance a host cell may be selected of the genus *Corynebacterium*, in particular *C. glutamicum*, enteric bacteria, in particular *Escherichia coli, Bacillus*, in particular *B. subtilis* and *B. methanolicus*, and *Saccharomyces*, in particular *S. cerevisiae*. Particularly suitable are *C. glutamicum* or *B. methanolicus* strains which have been developed for the industrial production of lysine.

The invention further relates to a micro-organism, which may be a wild-type micro-organism isolated from its natural environment or a recombinant micro-organism, comprising DNA containing a nucleic acid sequence as identified in any Sequence ID selected from the group of Sequence ID 3, Sequence ID 6, Sequence ID 13, Sequence ID No. 32, Sequence ID No. 35, Sequence ID No. 41, Sequence ID No. 44, Sequence ID No. 47, and functional analogues thereof.

Functional analogues of a nucleotides sequence, as referred to herein, are in particular nucleotide sequences encoding the same amino acid sequence as that nucleotide sequence or encoding a homologue of that nucleotide sequence. In particular, preferred functional analogues are nucleotide sequence having a similar, the same or a better level of expression in a host cell of interest as the nucleotide sequence of which it is referred to as being a functional analogue of.

The invention further relates to a polynucleotide or vector comprising a nucleic acid sequence as identified in any Sequence ID selected from the group of Sequence ID 3, Sequence ID 6, Sequence ID 13, Sequence ID No. 32, Sequence ID No. 35, Sequence ID No. 41, Sequence ID No. 44, Sequence ID No. 47 and non-wild-type functional analogues thereof. Such polynucleotide or vector is in particular advantageous for providing a host cell, especially an *E. coli* host cell, or another host cell which is capable of catalysing at least one reaction step in the conversion of AKP to 6-ACA with a high yield, compared to a corresponding wild-type gene.

Optionally, the polynucleotide or vector comprises one or more nucleic acid sequences encoding one or more other biocatalysts suitable for catalysing a reaction step in a method according to the invention, in particular such one or more of the biocatalyst referred to above.

The invention further relates to a method for preparing alpha-aminopimelic acid (AAP), comprising converting AKP into AAP, which conversion is catalysed by a biocatalyst.

For such method in particular a biocatalyst may be used having aminotransferase activity or reductive amination activity as described above.

As indicated above, the AAP may thereafter be used for the preparation of 6-ACA. Alternatively, AAP may be used as such, e.g. as a chemical for biochemical research or as a pH-buffer compound, e.g. for use in an preparative or analytical separation technique such as liquid chromatography or capillary electrophoresis.

Further, AAP prepared in a method of the invention may further be used in the preparation of another compound, for instance, AAP may be converted into caprolactam. As described above, and illustrated in an example, below. AAP can be chemically converted in caprolactam, e.g. by exposure to a high temperature. Without being bound by theory, it is contemplated that also in this reaction 6-ACA may be formed as a short-lived intermediate.

Next, the invention will be illustrated by the following examples.

EXAMPLES

General Methods

Molecular and Genetic Techniques

Standard genetic and molecular biology techniques are generally known in the art and have been previously described (Maniatis et al. 1982 "Molecular cloning: a laboratory manual". Cold Spring Harbor Laboratory, Cold Spring Harbor, N.Y.; Miller 1972 "Experiments in molecular genetics", Cold Spring Harbor Laboratory, Cold Spring Harbor; Sambrook and Russell 2001 "Molecular cloning: a laboratory manual" (3rd edition), Cold Spring Harbor Laboratory, Cold Spring Harbor Laboratory Press; F. Ausubel et al, eds., "Current protocols in molecular biology", Green Publishing and Wiley Interscience, New York 1987).

Plasmids and Strains pBAD/Myc-His C was obtained from Invitrogen (Carlsbad, Calif., USA). Plasmid pBAD/Myc-His-DEST constructed as described in WO2005/068643, was used for protein expression. E. coli TOP10 (Invitrogen, Carlsbad, Calif., USA) was used for all cloning procedures and for expression of target genes.

Media

LB medium (10 g/l tryptone, 5 g/l yeast extract, 5 g/l NaCl) was used for growth of E. coli. Antibiotics (50 μg/ml carbenicillin) were supplemented to maintain plasmids. For induction of gene expression under control of the $P_{BAD}$ promoter in pBAD/Myc-His-DEST derived plasmids, L-arabinose was added to a final concentration of 0.2% (w/v).

Identification of Plasmids

Plasmids carrying the different genes were identified by genetic, biochemical, and/or phenotypic means generally known in the art, such as resistance of transformants to antibiotics, PCR diagnostic analysis of transformant or purification of plasmid DNA, restriction analysis of the purified plasmid DNA or DNA sequence analysis.

HPLC-MS Analysis Method for the Determination of 5-FVA

5-FVA was detected by selective reaction monitoring (SRM)-MS, measuring the transition m/z 129→83. Concentrations for 5-FVA were calculated by measuring the peak area of the 5-FVA peak eluting at approximately 6 min. Calibration was performed by using an external standard procedure. All the LC-MS experiments were performed on an Agilent 1200 LC system, consisting of a quaternary pump, autosampler and column oven, coupled with an Agilent 6410 QQQ triple quadrupole MS.

LC Conditions:

| Column: | 50 × 4.6 mm Nucleosil C18, 5 μm (Machery & Nagel) pre column coupled to a 250 × 4.6 mm id. Prevail C18, 5 μm (Alltech) |
|---|---|
| Column temperature: | room temperature |
| Eluent: | A: water containing 0.1% formic acid B: acetonitrile containing 0.1% formic acid |

| Gradient: | time (min) | % eluent B |
|---|---|---|
| | 0 | 10 |
| | 6 | 50 |
| | 6.1 | 10 |
| | 11 | 10 |

| Flow: | 1.2 ml/min, before entering the MS the flow is split 1:3 |
|---|---|
| Injection volume: | 2 μl |

MS Conditions:

| Ionisation: | negative ion electrospray source conditions: ionspray voltage: 5 kV temperature: 350° C. fragmentor voltage and collision energy optimized |
|---|---|
| Scan mode: | selective reaction mode: transition m/z 129 → 83 |

HPLC-MS Analysis for the Determination of AAP

AAP was detected by selected ion monitoring (SIM)-MS, measuring the protonated molecule for AAP with m/z 176. Concentrations for AAP were calculated by measuring the peak area of the AAP peak eluting at a retention time of 2.7 minutes in the samples. Calibration was performed by using an external standard procedure. All the LC-MS experiments were performed on an Agilent 1100 LC system consisting of a quaternary pump, degasser, autosampler and column oven, coupled with an API 2000 triple quadrupole MS (Applied Biosystems).

LC conditions were as follows:

Column: 50*4 Nucleosil C18, 5 μm (Macherey-Nagel)+ 250×4.6 Prevail C18, 5 μm (Alltech), both at room temperature (RT)

Eluent: A=0.1% (v/v) formic acid in ultrapure water

B=0.1% (v/v) formic acid in acetonitrile (pa, Merck)

Flow: 1.2 ml/min, before entering the MS the flow was split 1:3

Gradient: The gradient was started at t=0 minutes with 90% (v/v) A and changed within 6 minutes to 50% (v/v) A. At 6.1 minutes the gradient was changed to the original condition.

Injection volume: 2 μl

MS conditions: Positive ion electrospray was used for ionization

Detection: in SIM mode on m/z 176, with a dwell time of 100 msec.

HPLC-MS analysis for the determination of 6-ACA

Calibration:

The calibration was performed by an external calibration line of 6-ACA (m/z 132→m/z 114, Rt 7.5 min). All the LC-MS experiments were performed on an Agilent 1100, equipped with a quaternary pump, degasser, autosampler, column oven, and a single-quadrupole MS (Agilent, Waldbronn, Germany). The LC-MS conditions were:

Column: 50*4 Nucleosil (Mancherey-Nagel)+250×4.6 Prevail C18 (Alltech), both at room temperature (RT)

Eluent: A=0.1(v/v) formic acid in ultrapure water

B=Acetonitrile (pa, Merck)

Flow: 1.0 ml/min, before entering the MS the flow was split 1:3

Gradient: The gradient was started at t=0 minutes with 100% (v/v) A, remaining for 15 minutes and changed within 15 minutes to 80% (v/v) B (t=30 minutes). From 30 to 31 minutes the gradient was kept at constant at 80% (v/v) B.

Injection volume: 5 μl

MS detection: ESI(+)-MS

The electrospray ionization (ESI) was run in the positive scan mode with the following conditions; m/z 50-500, 50 V fragmentor, 0.1 m/z step size, 350° C. drying gas temperature, 10 L N₂/min drying gas, 50 psig nebuliser pressure and 2.5 kV capillary voltage.

Cloning of Target Genes

Design of Expression Constructs attB sites were added to all genes upstream of the ribosomal binding site and start codon and downstream of the stop codon to facilitate cloning using the Gateway technology (Invitrogen, Carlsbad, Calif., USA).

Gene Synthesis and Construction of Plasmids

Synthetic genes were obtained from DNA2.0 and codon optimised for expression in *E. coli* according to standard procedures of DNA2.0. The aminotransferase genes from *Vibrio fluvialis* JS17 [SEQ ID No. 1] and *Bacillus weihenstephanensis* KBAB4 [SEQ ID No. 4] encoding the amino acid sequences of the *V. fluvialis* JS17 ω-aminotransferase [SEQ ID No. 2] and the *B. weihenstephanensis* KBAB4 aminotransferase (ZP_01186960) [SEQ ID No. 5], respectively, were codon optimised and the resulting sequences [SEQ ID No. 3] and [SEQ ID No. 6] were obtained by DNA synthesis.

The decarboxylase genes from *Escherichia coli* [SEQ ID No. 30], *Saccharomyces cerevisiae* [SEQ ID No. 33], *Zymomonas mobilis* [SEQ ID No. 36], *Lactococcus lactis* [SEQ ID No. 39], [SEQ ID No. 42] and *Mycobacterium tuberculosis* [SEQ ID No. 45], the *Escherichia coli* diaminopimelate decarboxylase LysA [SEQ ID No. 31], the *Saccharomyces cerevisiae* pyruvate decarboxylase Pdc [SEQ ID No. 34], the *Zymomonas mobilis* pyruvate decarboxylase Pdc1472A [SEQ ID No. 37], the *Lactococcus lactis* branched chain alpha-keto acid decarboxylase KdcA [SEQ ID No. 40] and alpha-ketoisovalerate decarboxylase KivD [SEQ ID No. 43], and the *Mycobacterium tuberculosis* alpha ketoglutarate decarboxylase Kgd [SEQ ID No. 46], respectively, were also codon optimised and the resulting sequences [SEQ ID No. 32], [SEQ ID No. 35], [SEQ ID No. 38], [SEQ ID No. 41], [SEQ ID No. 44], and [SEQ ID No. 47] were obtained by DNA synthesis, respectively.

The gene constructs were cloned into pBAD/Myc-His-DEST expression vectors using the Gateway technology (Invitrogen) via the introduced attB sites and pDONR201 (Invitrogen) as entry vector as described in the manufacturer's protocols (www[dot]invitrogen[dot]com). This way the expression vectors pBAD-Vfl_AT and pBAD-Bwe_AT were obtained, respectively. The corresponding expression strains were obtained by transformation of chemically competent *E. coli* TOP10 (Invitrogen) with the respective pBAD-expression vectors.

Cloning by PCR

Various genes encoding a biocatalyst were amplified from genomic DNA by PCR using PCR Supermix High Fidelity (Invitrogen) according to the manufacturer's specifications, using primers as listed in the following table.

TABLE 2

| origin of gene | gene Sequence ID | enzyme Sequence ID | primer Sequence ID's |
|---|---|---|---|
| *Pseudomonas aeruginosa* | 7 | 8 | 9&10 |
| *Pseudomonas aeruginosa* | 26 | 27 | 60&61 |
| *Pseudomonas aeruginosa* | 66 | 67 | 72&73 |
| *Pseudomonas aeruginosa* | 68 | 69 | 74&75 |
| *Bacillus subtilis* | 14 | 15 | 48&49 |
| *Bacillus subtilis* | 16 | 17 | 50&51 |
| *Bacillus subtilis* | 64 | 65 | 70&71 |

TABLE 2-continued

| origin of gene | gene Sequence ID | enzyme Sequence ID | primer Sequence ID's |
|---|---|---|---|
| *Rhodobacter sphaeroides* | 18 | 19 | 52&53 |
| *Legionella pneumophila* | 20 | 21 | 54&55 |
| *Nitrosomas europaea* | 22 | 23 | 56&57 |
| *Neisseria gonorrhoeae* | 24 | 25 | 58&59 |
| *Rhodopseudomonas palustris* | 28 | 29 | 62&63 |

PCR reactions were analysed by agarose gel electrophoresis and PCR products of the correct size were eluted from the gel using the QIAquick PCR purification kit (Qiagen, Hilden, Germany). Purified PCR products were cloned into pBAD/Myc-His-DEST expression vectors using the Gateway technology (Invitrogen) via the introduced attB sites and pDONR-zeo (Invitrogen) as entry vector as described in the manufacturer's protocols. The sequence of genes cloned by PCR was verified by DNA sequencing. This way the expression vectors pBAD-Pae-_gi9946143_AT, pBAD-Bsu_gi16078032_AT, pBAD-Bsu_gil 6080075_AT, pBAD-Bsu_gi16077991_AT, pBAD-Rsp_AT, pBAD-Lpn_AT, pBAD-Neu_AT, pBAD-Ngo_AT, pBAD-Pae_gi9951299_AT, pBAD-Pae_gi9951072_AT, pBAD-Pae_gi9951630_AT and pBAD-Rpa_AT were obtained. The corresponding expression strains were obtained by transformation of chemically competent *E. coli* TOP10 (Invitrogen) with the pBAD constructs.

Growth of *E. Coli* for Protein Expression

Small scale growth was carried out in 96-deep-well plates with 940 µl media containing 0.02% (w/v) L-arabinose. Inoculation was performed by transferring cells from frozen stock cultures with a 96-well stamp (Kühner, Birsfelden, Switzerland). Plates were incubated on an orbital shaker (300 rpm, 5 cm amplitude) at 25° C. for 48 h. Typically an $OD_{620nm}$ of 2-4 was reached.

Preparation of Cell Lysates

Preparation of Lysis Buffer

The lysis buffer contained the following ingredients:

TABLE 3

| 1M MOPS pH 7.5 | 5 ml |
|---|---|
| DNAse I grade II (Roche) | 10 mg |
| Lysozyme | 200 mg |
| MgSO₄•7H₂O | 123.2 mg |
| dithiothreitol (DTT) | 154.2 mg |
| H₂O (MilliQ) | Balance to 100 ml |

The solution was freshly prepared directly before use.

Preparation of Cell Free Extract by Lysis

Cells from small scales growth (see previous paragraph) were harvested by centrifugation and the supernatant was discarded. The cell pellets formed during centrifugation were frozen at −20° C. for at least 16 h and then thawed on ice. 500 µl of freshly prepared lysis buffer were added to each well and cells were resuspended by vigorously vortexing the plate for 2-5 min. To achieve lysis, the plate was incubated at room temperature for 30 min. To remove cell debris, the plate was centrifuged at 4° C. and 6000 g for 20 min. The supernatant was transferred to a fresh plate and kept on ice until further use.

Preparation of Cell Free Extract by Sonification

Cells from medium scales growth (see previous paragraph) were harvested by centrifugation and the supernatant was discarded. 1 ml of potassium phosphate buffer pH7 was added to 0.5 g of wet cell pellet and cells were resuspended by vigorously vortexing. To achieve lysis, the cells were sonicated for 20 min. To remove cell debris, the lysates were centrifuged at 4° C. and 6000 g for 20 min. The supernatant was transferred to a fresh tube and frozen at −20° C. until further use.

Preparation of 5-Formylpentanoic Acid by Chemical Hydrolysis of Methyl 5-Formylpentanoate The substrate for the aminotransferase reaction i.e. 5-formylpentanoic acid was prepared by chemical hydrolysis of methyl 5-formylpentanoate as follows: a 10% (w/v) solution of methyl 5-formylpentanoate in water was set at pH 14.1 with NaOH. After 24 h of incubation at 20° C. the pH was set to 7.1 with HCl.

Enzymatic Reactions for Conversion of 5-Formylpentanoic Acid to 6-ACA

Unless specified otherwise, a reaction mixture was prepared comprising 10 mM 5-formylpentanoic acid, 20 mM racemic α-methylbenzylamine, and 200 µM pyridoxal 5'-phosphate in 50 mM potassium phosphate buffer, pH 7.0. 100 µl of the reaction mixture were dispensed into each well of the well plates. To start the reaction, 20 µl of the cell free extracts were added, to each of the wells. Reaction mixtures were incubated on a shaker at 37° C. for 24 h. Furthermore, a chemical blank mixture (without cell free extract) and a biological blank (*E. coli* TOP10 with pBAD/Myc-H is C) were incubated under the same conditions. Samples were analysed by HPLC-MS. The results are summarised in the following table.

TABLE 4

6-ACA formation from 5-FVA in the presence of aminotransferases

| Biocatalyst | 6-ACA concentration [mg/kg] |
|---|---|
| *E. coli* TOP10/pBAD-Vfl_AT | 43* |
| *E. coli* TOP10/pBAD-Pae_AT | 930 |
| *E. coli* TOP10/pBAD-Pae_AT | 25* |
| *E. coli* TOP10/pBAD-Bwe_AT | 24* |
| *E. coli* TOP10/pBAD-Bsu_gi16077991_AT | 288 |
| *E. coli* TOP10/pBAD-Pae_gi9951072_AT | 1087 |
| *E. coli* TOP10/pBAD-Pae_gi9951630_AT | 92 |
| *E. coli* TOP10 with pBAD/Myc-His C (biological blank) | 0.6 |
| None (chemical blank) | n.d. | n.d.: not detectable

*method differed in that 10 µl cell free extract was used instead of 20 µl, the pyridoxal-5'-phosphate concentration was 50 µM instead of 200 µM and the reaction mixture volume in the wells was 190 µl instead of 100 µl.

It is shown that 6-ACA is formed from 5-FVA in the presence of an aminotransferase.

Enzymatic Reactions for Conversion of AKP to 5-Formylpentanoic acid

A reaction mixture was prepared comprising 50 mM AKP, 5 mM magnesium chloride, 100 µM pyridoxal 5'-phosphate (for LysA) or 1 mM thiamine diphosphate (for all other enzymes) in 100 mM potassium phosphate buffer, pH 6.5. 4 ml of the reaction mixture were dispensed into a reaction vessel. To start the reaction, 1 ml of the cell free extracts obtained by sonification were added, to each of the wells. In case of the commercial oxaloacetate decarboxylase (Sigma-Aldrich product number 04878), 50 U were used. Reaction mixtures were incubated with a magnetic stirrer at 37° C. for 48 h. Furthermore, a chemical blank mixture (without cell free extract) and a biological blank (*E. coli* TOP10 with pBAD/Myc-His C) were incubated under the same conditions. Samples from different time points during the reaction were analysed by HPLC-MS. The results are summarised in the following table.

TABLE 5

5-FVA formation from AKP in the presence of decarboxylases

| | 5-FVA concentration [mg/kg] | | |
|---|---|---|---|
| Biocatalyst | 3 h | 18 h | 48 h |
| *E. coli* TOP10/pBAD-LysA | 150 | 590 | 720 |
| *E. coli* TOP10/pBAD-Pdc | 1600 | 1700 | 1300 |
| *E. coli* TOP10/pBAD-PdcI472A | 2000 | 2000 | 1600 |
| *E. coli* TOP10/pBAD-KdcA | 3300 | 2300 | 2200 |
| *E. coli* TOP10/pBAD-KivD | 820 | 1400 | 1500 |
| Oxaloacetate decarboxylase | n.d. | 6 | 10 |
| *E. coli* TOP10 with pBAD/Myc-His C (biological blank) | n.d. | n.d. | n.d. |
| None (chemical blank) | n.d. | n.d. | n.d. | n.d.: not detectable

It is shown that 5-FVA is formed from AKP in the presence of a decarboxylase.

Enzymatic Reactions for Conversion of AKP to 6-ACA in Presence of Recombinant Decarboxylase A reaction mixture was prepared comprising 50 mM AKP, 5 mM magnesium chloride, 100 µM pyridoxal 5'-phosphate (for LysA) or 1 mM thiamine diphosphate (for all other tested biocatalysts) in 100 mM potassium phosphate buffer, pH 6.5. 4 ml of the reaction mixture were dispensed into a reaction vessel. To start the reaction, 1 ml of the cell free extracts were added, to each of the wells. Reaction mixtures were incubated with a magnetic stirrer at 37° C. for 48 h. Furthermore, a chemical blank mixture (without cell free extract) and a biological blank (*E. coli* TOP10 with pBAD/Myc-His C) were incubated under the same conditions. Samples from different time points during the reaction were analysed by HPLC-MS. The results are summarised in the following table.

TABLE 6

6-ACA formation from AKP in the presence of decarboxylases

| | 6-ACA concentration [mg/kg] | | |
|---|---|---|---|
| Biocatalyst | 3 h | 18 h | 48 h |
| *E. coli* TOP10/pBAD-LysA | n.a. | 0.01 | 0 |
| *E. coli* TOP10/pBAD-Pdc | 0.1 | 0.3 | n.a. |
| *E. coli* TOP10/pBAD-PdcI472A | 0.03 | 0.1 | 0.2 |
| *E. coli* TOP10/pBAD-KdcA | 0.04 | 0.1 | 0.3 |
| *E. coli* TOP10/pBAD-KivD | n.a. | 0.3 | 0.6 |
| *E. coli* TOP10 with pBAD/Myc-His C (biological blank) | n.d. | n.d. | n.d. |
| None (chemical blank) | n.d. | n.d. | n.d. | n.a. = not analysed
n.d. = not detectable

It is shown that 6-ACA is formed from AKP in the presence of a decarboxylase. It is contemplated that the *E. coli* contained natural 5-FVA aminotransferase activity.

Enzymatic Reactions for Conversion of AKP to 6-ACA in Presence of Recombinant Decarboxylase and Recombinant Aminotransferase A reaction mixture was prepared comprising 50 mM AKP, 5 mM magnesium chloride, 100 µM pyridoxal 5'-phosphate, 1 mM thiamine diphosphate and 50 mM racemic α-methylbenzylamine in 100 mM potassium phosphate buffer, pH 6.5. 1.6 ml of the reaction mixture were dispensed into a reaction vessel. To start the reaction, 0.2 ml of the decarboxylase containing cell free extract and 0.2 ml of the aminotransferase containing cell free extract were added, to each of the reaction vessels. Reaction mixtures were incubated with a magnetic stirrer at 37° C. for 48 h. Furthermore, a chemical blank mixture (without cell free extract) and a biological blank (*E. coli* TOP10 with pBAD/Myc-His C) were incubated under the same conditions. Samples from different time points during the reaction were analysed by HPLC-MS. The results are summarised in the following table.

TABLE 7

6-ACA formation from AKP in the presence of a recombinant decarboxylase and a recombinant aminotransferase

| | 6-ACA concentration [mg/kg] after 48 hours AT | | |
|---|---|---|---|
| DC | *E. coli* TOP10/pBAD-Vfl-AT | *E. coli* TOP10/pBAD-Bwe-AT | *E. coli* TOP10/pBAD-PAE_gi9946143_AT |
| *E. coli* TOP10/pBAD-Pdc | 183.4 | 248.9 | 117.9 |
| *E. coli* TOP10/pBAD-PdcI472A | 458.5 | 471.6 | 170.3 |
| *E. coli* TOP10/pBAD-KdcA | 497.8 | 497.8 | 275.1 |
| *E. coli* TOP10/pBAD-KivD | 510.9 | 510.9 | 314.4 |

AT = aminotransferase
DC = decarboxylase

In the chemical blank and in the biological blank no 6-ACA was detectable.

Further, the results show that compared to the example wherein a host-cell with only recombinant decarboxylase (and no recombinant aminotransferase) the conversion to 6-ACA was improved.

Construction of Plasmids for Expression of Aminotransferases and Decarboxylases in *S. Cerevisiae*

The aminotransferase gene from *Vibrio fluvialis* JS17 encoding the amino acid sequence of the *V. fluvialis* JS17 ω-aminotransferase [SEQ ID No. 2] was amplified by PCR from pBAD-Vfl_AT [SEQ ID No. 3] using Phusion DNA polymerase (Finnzymes) according to the manufacturers specifications and using specific primers [SEQ ID No. 76 & 77].

The aminotransferase gene from *Pseudomonas aeruginosa* [SEQ ID No. 7] coding for *P. aeruginosa* aminotransferase [SEQ ID No. 8] was amplified from pBAD-Pae_AT by PCR using Phusion DNA polymerase (Finnzymes) according to the manufacturers specifications and using specific primers [SEQ ID No. 78 & 79].

The resulting PCR products were cloned into vector pAKP-41 using SpeI and BamHI restriction enzymes resulting in vectors pAKP-79 and pAKP-80 respectively, which now contain the aminotransferase gene under the *S. cerevisiae* gal10 promoter and the *S. cerevisiae* adh2 terminator.

The decarboxylase gene from *Saccharamyces cerevisiae* [SEQ ID No. 33] coding for *Saccharamyces cerevisiae* pyruvate decarboxylase Pdc [SEQ ID No. 34] was amplified from pBAD-Pdc by PCR using Phusion DNA polymerase (Finnzymes) according to the manufacturers specifications and using specific primers [SEQ ID No. 80 & 81].

The decarboxylase gene from *Lactococcus lactis* [SEQ ID No. 39] coding for *Lactococcus lactis* branched chain alpha-keto acid decarboxylase KdcA [SEQ ID No. 40] was amplified from pBAD-KdcA by PCR using Phusion DNA polymerase (Finnzymes) according to the manufacturers specifications and using specific primers [SEQ ID No 82 & 83].

The resulting PCR products were cloned into vector pAKP-44 using AscI and BamHI restriction enzymes resulting in vectors pAKP-81 and pAKP-82 respectively, which now contain the decarboxylase gene under the *S. cerevisiae* gal2 promoter and the *S. cerevisiae* pma1 terminator.

Plasmids pAKP-79 and pAKP-80 were restriction enzyme digested with SacI and XbaI and plasmids pAKP-81 and pAKP-82 were restriction enzyme digested with SalI and XbaI. A SacI/XbaI aminotransferase fragment was combined with a SalI/XbaI decarboxylase fragment into the *S. cerevisiae* low copy episomal vector pRS414, which was restriction enzyme digested with SalI and SacI.

The resulting plasmids were obtained:
pAKP-85: Pgal10-Pae_AT-Tadh2 Pgal2-Pdc_DC-Tpma1
pAKP-86: Pgal10-Pae_AT-Tadh2 Pgal2-KdcA_DC-Tpma1
pAKP-87: Pgal10-Vfl_AT-Tadh2 Pgal2-Pdc_DC-Tpma1
pAKP-88: Pgal10-Vfl_AT-Tadh2 Pgal2-KdcA_DC-Tpma1

Transformation and growth of *S. cerevisiae*

*S. cerevisiae* strain CEN.PK113-3C was transformed with 1 µg of plasmid DNA according to the method as described by Gietz and Woods (Gietz, R. D. and Woods, R. A. (2002). Transformation of yeast by the Liac/SS carrier DNA/PEG method. Methods in Enzymology 350: 87-96). Cells were plated on agar plates with 1× Yeast Nitrogen Base without amino acids and 2% glucose.

The resulting strains were grown aerobically at 30° C. for 48 hour in Verduyn minimal medium containing 0.05% glucose and 4% galactose.

Preparation of Cell Free Extract 1 ml of potassium phosphate buffer (pH 7) was added to 0.5 g of the cell pellet. This mixture was added to a 2 ml eppendorf tube which contained 0.5 g of glassbeads with a diameter of 0.4-0.5 mM. Samples were vigorously shaken with an eppendorf shaker (IKA VIBRAX-VXR) for 20 s. The resulting cell free extract was centrifuged for 5 minutes at 14000 rpm and 4° C. The supernatant was used for enzyme activity assays.

Enzymatic Reactions for Conversion of AKP to 6-ACA in Presence of Decarboxylase and Aminotransferase Co-Expressed in *S. Cerevisiae*

A reaction mixture was prepared comprising 50 mM AKP, 5 mM magnesium chloride, 100 µM pyridoxal 5'-phosphate, 1 mM thiamine diphosphate and 50 mM racemic α-methylbenzylamine in 100 mM potassium phosphate buffer, pH 6.5. 1.6 ml of the reaction mixture were dispensed into a reaction vessel. To start the reaction, 0.4 ml of the cell free extract from *S. cerevisiae* containing decarboxylase and aminotransferase were added, to each of the reaction vessels. Reaction mixtures were incubated with a magnetic stirrer at 37° C. Furthermore, a chemical blank mixture (without cell free extract) and a biological blank (*S. cerevisiae*) were incubated under the same conditions. Samples, taken after 19 hours of incubation, were analysed by HPLC-MS. The results are summarised in the following table.

TABLE 8

6-ACA formation from AKP using a micro-organism as a biocatalyst

| Biocatalyst | 6-ACA concentration [mg/kg] |
|---|---|
| *S. cerevisiae* pAKP-85 | 63 |
| *S. cerevisiae* pAKP-86 | 226 |

TABLE 8-continued

6-ACA formation from AKP using a micro-organism as a biocatalyst

| Biocatalyst | 6-ACA concentration [mg/kg] |
|---|---|
| S. cerevisiae pAKP-87 | 1072 |
| S. cerevisiae pAKP-88 | 4783 |
| S. cerevisiae (biological blank) | 3.9 |
| None (chemical blank) | 1.3 |

Enzymatic Reactions for Conversion of Alpha-Ketopimelic Acid to Alpha-Aminopimelic Acid A reaction mixture was prepared comprising 10 mM alpha-ketopimelic acid, 20 mM L-alanine, and 50 µM pyridoxal 5'-phosphate in 50 mM potassium phosphate buffer, pH 7.0. 800 µl of the reaction mixture were dispensed into each well of the well plates. To start the reaction, 200 µl of the cell lysates were added, to each of the wells. Reaction mixtures were incubated on a shaker at 37° C. for 24 h. Furthermore, a chemical blank mixture (without cell free extract) and a biological blank (E. coli TOP10 with pBAD/Myc-His C) were incubated under the same conditions. Samples were analysed by HPLC-MS. The results are summarised in the following table.

TABLE 9

AAP formation from AKP in the presence of aminotransferases

| Biocatalyst | AAP concentration [mg/kg] (after 24 hrs) |
|---|---|
| E. coli TOP10/pBAD-Vfl_AT | 3.7 |
| E. coli TOP10/pBAD-Psy_AT | 15.8 |
| E. coli TOP10/pBAD-Bsu_gi16078032_AT | 11.2 |
| E. coli TOP10/pBAD-Rsp_AT | 9.8 |
| E. coli TOP10/pBAD-Bsu_gi16080075_AT | 4.6 |
| E. coli TOP10/pBAD-Lpn_AT | 5.4 |
| E. coli TOP10/pBAD-Neu_AT | 7.7 |
| E. coli TOP10/pBAD-Ngo_AT | 5.1 |
| E. coli TOP10/pBAD-Pae_gi9951299_AT | 5.6 |
| E. coli TOP10/pBAD-Rpa_AT | 5.4 |
| E. coli TOP10 with pBAD/Myc-His C (biological blank) | 1.4 |
| None (chemical blank) | 0 |

It is shown that the formation of AAP from AKP is catalysed by the biocatalyst.

Chemical Conversion of AAP to Caprolactam

To a suspension of 1.5 grams of D,L-2-aminopimelic acid in 21 ml cyclohexanone, 0.5 ml of cyclohexenone was added. The mixture was heated on an oil bath for 20 h at reflux (approximately 160° C.). After cooling to room temperature the reaction mixture was decanted and the clear solution was evaporated under reduced pressure. The remaining 2 grams of brownish oil were analyzed by $^1$H-NMR and HPLC and contained 0.8 wt % caprolactam and 6 wt % of cyclic oligomers of caprolactam.

We claim:

1. Method for preparing 6-aminocaproic acid, wherein the 6-aminocaproic acid is prepared from α-ketopimelic acid, using at least one biocatalyst, wherein said biocatalyst comprises two enzymes, wherein said two enzymes are an amino acid dehydrogenase (E.C. 1.4.1) and a decarboxylase (E.C. 4.1.1), and wherein said decarboxylase converts α-ketopimelic acid to 5-formylpentanoate and said amino acid dehydrogenase converts 5-formylpentanoate to 6-aminocaproic acid, or said amino acid dehydrogenase converts α-ketopimelic acid to alpha-aminopimelic acid and said decarboxylase converts alpha-aminopimelic acid to 6-aminocaproic acid.

2. Method according to claim 1, wherein the amino acid dehydrogenase is selected from the group of glutamate dehydrogenases acting with NAD or NADP as acceptor (E.C. 1.4.1.3), glutamate dehydrogenases acting with NADP as acceptor (E.C. 1.4.1.4), leucine dehydrogenases (E.C. 1.4.1.9), diaminopimelate dehydrogenases (E.C. 1.4.1.16), and lysine-6-dehydrogenases (EC, 1.4.1.18).

3. Method according to claim 1, wherein said amino acid dehydrogenase is from an organism selected from the group of *Corynebacterium glutamicum, Proteus vulgaris, Agrobacterium tumefaciens, Geobacillus stearothermophilus, Acinetobacter* sp. ADP1, *Ralstonia solanacearum, Salmonella typhimurium, Saccharomyces cerevisiae, Brevibacterium flavum, Bacillus sphaericus, Bacillus cereus* and *Bacillus subtilis*.

4. Method according to claim 1, wherein the decarboxylase is selected from the group of glutamate decarboxylases (E.C. 4.1.1.15), diaminopimelate decarboxylases (E.C. 4.1.1.20) aspartate 1-decarboxylases (E.C. 4.1.1.11), branched chain α-keto acid decarboxylases, α-ketoisovalerate decarboxylases, α-ketoglutarate decarboxylases, pyruvate decarboxylases (E.C. 4.1.1.1), and oxaloacetate decarboxylases (E.C. 4.1.1.3).

5. Method according to claim 1, wherein the decarboxylase is from an organism selected from the group of *Saccharomyces cerevisiae, Candida flareri, Hansenula* sp., *Kluyveromyces marxianus, Rhizopus javanicus, Neurospora crassa*, mammals, *Escherichia coli, Lactococcus lactis, Mycobacterium tuberculosis, Pseudomonas* sp. and *Zymomonas mobilis*.

6. Method according to claim 1, wherein the decarboxylase comprises the amino acid sequence of SEQ ID NO: 31, SEQ ID NO: 34, SEQ ID NO: 37, SEQ ID NO: 40, SEQ ID NO: 43 or SEQ ID NO: 46.

7. Method according to claim 1, wherein said decarboxylase converts α-ketopimelic acid to 5-formylpentanoate and said amino acid dehydrogenase converts 5-formylpentanoate to 6-aminocaproic acid.

8. Method according to claim 1, wherein said amino acid dehydrogenase converts α-ketopimelic acid to alpha-aminopimelic acid and said decarboxylase converts alpha-aminopimelic acid to 6-aminocaproic acid.

9. Method according to claim 1, wherein the α-ketopimelic acid has been obtained from a natural source.

10. A recombinant host cell, comprising a heterologous nucleic acid sequence encoding an amino acid dehydrogenase selected from the group of glutamate dehydrogenases acting with NAD or NADP as acceptor (E.C. 1.4.1.3), glutamate dehydrogenases acting with NADP as acceptor (E.C.1.4.1.4), leucine dehydrogenases (E.C. 1.4.1.9), diaminopimelate dehydrogenases (E.C.1.4.1.16), and lysine-6-dehydrogenases (E.C. 1.4.1.18) and a heterologous nucleic acid sequence encoding a decarboxylase selected from the group of glutamate decarboxylases (E.C. 4.1.1.15), diaminopimelate decarboxylases (E.C. 4.1.1.20) aspartate 1-decarboxylases (E.C. 4.1.1.11), branched chain α-keto acid decarboxylases, α-ketoisovalerate decarboxylases, α-ketoglutarate decarboxylases, pyruvate decarboxylases (E.C. 4.1.1.1), and oxaloacetate decarboxylases (E.C. 4.1.1.3).

11. A recombinant host cell according to claim 10, wherein the host cell is selected from the group of *Aspergillus, Penicillium, Saccharomyces, Kluyveromyces, Pichia, Candida, Hansenula, Bacillus, Corynebacterium*, and *Escherichia*.

12. A recombinant host cell according to claim 10, comprising one or more heterologous nucleic acid sequences encoding one or more enzymes biocatalysts capable of catalyzing at least one reaction step in the preparation of alpha-ketopimelic acid from alpha-ketoglutaric acid.

13. A recombinant host cell according to claim 10, wherein said amino acid dehydrogenase is from an organism selected from the group of *Corynebacterium glutamicum, Proteus vulgaris, Agrobacterium tumefaciens, Geobacillus stearothermophilus, Acinetobacter* sp. ADP1, *Ralstonia solanacearum, Salmonella typhimurium, Saccharomyces cerevisiae, Brevibacterium flavum, Bacillus sphaericus, Bacillus cereus* and *Bacillus subtilis*.

14. A recombinant host cell according to claim 10, wherein the decarboxylase is from an organism selected from the group of *Saccharomyces cerevisiae, Candida flareri, Hansenula* sp., *Kluyveromyces marxianus, Rhizopus javanicus, Neurospora crassa*, mammals, *Escherichia coli, Lactococcus lactis, Mycobacterium tuberculosis, Pseudomonas* sp. and *Zymomonas mobilis*.

15. A recombinant host cell according to claim 10 wherein said decarboxylase comprises an amino acid sequence according to SEQ ID NO: 31, SEQ ID NO: 34, SEQ ID NO: 37, SEQ ID NO: 40, SEQ ID NO: 43 or SEQ ID NO: 46.

* * * * *